(12) United States Patent
Van Tuyl

(10) Patent No.: US 7,275,807 B2
(45) Date of Patent: Oct. 2, 2007

(54) WAVE GUIDE WITH ISOLATED COUPLING INTERFACE

(75) Inventor: Michael Van Tuyl, San Jose, CA (US)

(73) Assignee: EDC Biosystems, Inc., Milpitas, CA (US)

( * ) Notice: Subject to any disclaimer, the term of this patent is extended or adjusted under 35 U.S.C. 154(b) by 564 days.

(21) Appl. No.: 10/388,962

(22) Filed: Mar. 14, 2003

(65) Prior Publication Data

US 2004/0102742 A1   May 27, 2004

Related U.S. Application Data

(60) Provisional application No. 60/435,767, filed on Dec. 19, 2002, provisional application No. 60/434,756, filed on Dec. 18, 2002, provisional application No. 60/429,778, filed on Nov. 27, 2002.

(51) Int. Cl.
  *G01N 1/10* (2006.01)
  *B41J 2/135* (2006.01)
(52) U.S. Cl. .......................... 347/46; 422/100; 436/180
(58) Field of Classification Search ................ 422/100; 436/180; 347/46
  See application file for complete search history.

(56) References Cited

U.S. PATENT DOCUMENTS

| | | | |
|---|---|---|---|
| 3,903,990 A | 9/1975 | Tannaka | |
| 4,225,951 A | 9/1980 | Menin et al. | |
| 4,308,547 A | 12/1981 | Lovelady et al. | |
| 4,385,255 A | 5/1983 | Yamaguchi et al. | |
| 4,493,795 A | 1/1985 | Nestor, Jr. et al. | |
| 4,605,009 A | 8/1986 | Pourcelot et al. | |

(Continued)

FOREIGN PATENT DOCUMENTS

DE   41 28 590   3/1993

(Continued)

OTHER PUBLICATIONS

Avrameas, S. et al. (1978). "Coupling of Enzymes to Antibodies and Antigens," *Scandinavia Journal of Immunology* vol. 8(supp7):7-23.

(Continued)

*Primary Examiner*—Jill Warden
*Assistant Examiner*—Paul S Hyun
(74) *Attorney, Agent, or Firm*—Morrison & Foerster LLP

(57) ABSTRACT

A wave-guide having an isolated coupling interface. In one variation, a constant negative pressure is maintained around the area surrounding the wave-guide. Coupling liquid may be directed to the tip of the wave-guide to provide the coupling interface between the wave-guide and a source fluid container. The suction from the constant negative pressure may remove excess coupling liquid and isolating the coupling liquid to the area around the tip of the wave-guide. The wave-guide assembly may also include mechanisms for adjusting the volume of fluid at the tip of the wave-guide. When the position of the wave-guide is displaced, fluid compensation mechanism may increase or decrease the volume of fluids at the distal end of the wave-guide to maintain proper coupling between the wave-guide and the source fluid container. Methods for utilizing negative pressure around the distal end of the wave-guide to isolate the coupling liquid are also described.

12 Claims, 32 Drawing Sheets

U.S. PATENT DOCUMENTS

| | | |
|---|---|---|
| 4,697,195 A | 9/1987 | Quate et al. |
| 4,719,476 A | 1/1988 | Elrod et al. |
| 4,719,480 A | 1/1988 | Elrod et al. |
| 4,745,419 A | 5/1988 | Quate et al. |
| 4,748,461 A | 5/1988 | Elrod |
| 4,749,900 A | 6/1988 | Hadimioglu et al. |
| 4,751,529 A | 6/1988 | Elrod et al. |
| 4,751,530 A | 6/1988 | Elrod et al. |
| 4,751,534 A | 6/1988 | Elrod et al. |
| 4,782,350 A | 11/1988 | Smith et al. |
| 4,797,693 A | 1/1989 | Quate |
| 4,801,950 A | 1/1989 | Frehling |
| 4,801,953 A | 1/1989 | Quate |
| 4,867,517 A | 9/1989 | Rawson |
| 4,959,674 A | 9/1990 | Khuri-Yakub et al. |
| 5,028,937 A | 7/1991 | Khuri-Yakub et al. |
| 5,041,849 A | 8/1991 | Quate et al. |
| 5,070,488 A | 12/1991 | Fukushima et al. |
| 5,074,649 A | 12/1991 | Hamanaka |
| 5,087,931 A | 2/1992 | Rawson |
| 5,111,220 A | 5/1992 | Hadimioglu et al. |
| 5,115,809 A | 5/1992 | Saitoh et al. |
| 5,121,141 A | 6/1992 | Hadimoglu et al. |
| 5,122,818 A | 6/1992 | Elrod et al. |
| 5,142,307 A | 8/1992 | Elrod et al. |
| 5,163,436 A | 11/1992 | Saitoh et al. |
| 5,176,140 A | 1/1993 | Kami et al. |
| 5,191,354 A | 3/1993 | Quate |
| 5,194,880 A | 3/1993 | Elrod et al. |
| 5,216,451 A | 6/1993 | Rawson et al. |
| 5,229,793 A | 7/1993 | Hadimioglu et al. |
| 5,231,426 A | 7/1993 | Sweet |
| 5,268,610 A | 12/1993 | Hadimioglu et al. |
| 5,278,028 A | 1/1994 | Hadimioglu et al. |
| 5,287,126 A | 2/1994 | Quate |
| 5,299,578 A | 4/1994 | Rotteveel et al. |
| 5,305,016 A | 4/1994 | Quate |
| 5,339,101 A | 8/1994 | Rawson et al. |
| 5,379,865 A | 1/1995 | Berdich et al. |
| 5,389,956 A | 2/1995 | Hadimioglu et al. |
| 5,428,381 A | 6/1995 | Hadimioglu et al. |
| 5,450,107 A | 9/1995 | Rawson |
| 5,469,744 A * | 11/1995 | Patton et al. ............... 73/644 |
| 5,504,564 A | 4/1996 | Snelling et al. |
| 5,520,715 A | 5/1996 | Oeftering |
| 5,541,627 A | 7/1996 | Quate |
| 5,565,113 A | 10/1996 | Hadimioglu et al. |
| 5,589,864 A | 12/1996 | Hadimioglu |
| 5,591,490 A | 1/1997 | Quate |
| 5,608,433 A | 3/1997 | Quate |
| 5,612,723 A | 3/1997 | Shimura et al. |
| 5,629,724 A | 5/1997 | Elrod et al. |
| 5,631,678 A | 5/1997 | Hadimioglu et al. |
| 5,669,389 A | 9/1997 | Rotteveel et al. |
| 5,669,971 A | 9/1997 | Bok et al. |
| 5,686,945 A | 11/1997 | Quate et al. |
| 5,692,068 A | 11/1997 | Bryenton et al. |
| 5,709,737 A | 1/1998 | Malhotra et al. |
| 5,722,479 A | 3/1998 | Oeftering |
| 5,798,774 A | 8/1998 | Okada et al. |
| 5,798,779 A | 8/1998 | Nakayasu et al. |
| 5,808,636 A | 9/1998 | Stearns |
| 5,810,009 A | 9/1998 | Mine et al. |
| 5,821,958 A | 10/1998 | Lim |
| 5,877,800 A | 3/1999 | Robinson et al. |
| 5,912,679 A | 6/1999 | Takayama et al. |
| 6,003,388 A | 12/1999 | Oeftering |
| 6,007,183 A | 12/1999 | Horine |
| 6,015,880 A | 1/2000 | Baldeschwieler et al. |
| 6,019,814 A | 2/2000 | Horine |
| 6,029,518 A | 2/2000 | Oeftering |
| 6,038,752 A | 3/2000 | Finsterwald et al. |
| 6,048,050 A | 4/2000 | Gundlach et al. |
| 6,116,718 A | 9/2000 | Peeters et al. |
| 6,134,291 A | 10/2000 | Roy et al. |
| 6,136,210 A | 10/2000 | Biegelsen et al. |
| 6,142,618 A | 11/2000 | Smith et al. |
| 6,154,236 A | 11/2000 | Roy et al. |
| 6,159,013 A | 12/2000 | Parienti |
| 6,187,211 B1 | 2/2001 | Smith et al. |
| 6,200,491 B1 | 3/2001 | Zesch et al. |
| 6,299,272 B1 | 10/2001 | Baker et al. |
| 6,312,121 B1 | 11/2001 | Smith et al. |
| 6,336,696 B1 | 1/2002 | Ellson et al. |
| 6,368,482 B1 | 4/2002 | Oeftering et al. |
| 6,503,454 B1 | 1/2003 | Hadimioglu et al. |
| 6,514,704 B2 | 2/2003 | Bruce et al. |
| 6,596,239 B2 | 7/2003 | Williams et al. |
| 6,916,083 B2 | 7/2005 | Miller et al. |
| 2002/0001004 A1 | 1/2002 | Mantell et al. |
| 2002/0001005 A1 | 1/2002 | Kneezel et al. |
| 2002/0037359 A1 | 3/2002 | Mutz et al. |
| 2002/0037375 A1 | 3/2002 | Ellson et al. |
| 2002/0037527 A1 | 3/2002 | Ellson et al. |
| 2002/0037579 A1* | 3/2002 | Ellson et al. ............ 435/287.2 |
| 2002/0042077 A1 | 4/2002 | Ellson |
| 2002/0061258 A1 | 5/2002 | Mutz et al. |
| 2002/0061598 A1 | 5/2002 | Mutz et al. |
| 2002/0064808 A1 | 5/2002 | Mutz et al. |
| 2002/0064809 A1 | 5/2002 | Mutz et al. |
| 2002/0070993 A1 | 6/2002 | Mantell |
| 2002/0085063 A1 | 7/2002 | Mutz et al. |
| 2002/0086319 A1 | 7/2002 | Ellson et al. |
| 2002/0090720 A1 | 7/2002 | Mutz et al. |
| 2002/0102555 A1 | 8/2002 | Bruce et al. |
| 2002/0142286 A1 | 10/2002 | Mutz et al. |
| 2002/0155231 A1 | 10/2002 | Ellson et al. |
| 2002/0158144 A1 | 10/2002 | Anderson et al. |
| 2003/0080208 A1 | 5/2003 | Williams et al. |
| 2003/0116642 A1 | 6/2003 | Williams et al. |
| 2003/0133842 A1 | 7/2003 | Williams et al. |
| 2003/0161761 A1 | 8/2003 | Williams et al. |

FOREIGN PATENT DOCUMENTS

| | | |
|---|---|---|
| EP | 0 549 244 | 6/1993 |
| EP | 0 845 357 | 6/1998 |
| EP | 1 209 466 | 5/2002 |
| FR | 2 291 800 | 6/1976 |
| JP | 40-05479 | 1/1992 |
| WO | WO 02/24323 | 3/2002 |
| WO | WO 02/24324 | 3/2002 |
| WO | WO 02/24325 | 3/2002 |
| WO | WO 02/26394 | 4/2002 |
| WO | WO 02/26756 | 4/2002 |
| WO | WO 02/44319 | 6/2002 |
| WO | WO 02/47075 | 6/2002 |
| WO | WO 02/47820 | 6/2002 |
| WO | WO 02/066713 | 8/2002 |

OTHER PUBLICATIONS

DeLuca, D. (1982). "Immunofluorescence Analysis" Chapter 7 In *Antibody As A Tool* Marchalonis, J.J. and Warr, G.W. eds. John Wiley & Sons pp. 189-231.

Galfre, G. and Milstein, C. (1981). "Preparation of Monoclonal Antibodies: Strategies and Procedures" Chapter 1 In *Methods in Enzymology* Academic Press, Inc. 73:3-46.

Goldmann, T. and Gonzalez, J. S. (Mar. 2000). "DNA-Printing: Utilization of a Standard Inkjet Printer for the Transfer of Nucleic Acids to Solid Supports," *J. Biochem. Biophys. Methods* 42(3):105-110.

Lemieux, B. et al. (1998). "Overview of DNA Chip Technology," *Molecular Breeding* 4:277-289.

Lemmo, A.V. et al. (Feb. 1997). "Characterization of an Inkjet Chemical Microdispenser for Combinatorial Library Synthesis," *Analytical Chemistry* 69(4):543-551.

Mandenius, C.F. et al. (1986). "Reversible and Specific Interaction of Dehydrogenases with a Coenzyme-Coated Surface Continuously Monitored with a Reflectometer," *Analytical Biochemistry* 157:283-288.

NASA, Glenn Research Center, (Oct. 2001). "Technology Opportunity: Acoustic Micro-Dispensing," Combustion & Fluids TOP3-00130 located at: <http://technology.nasa.gov/scripts/nls> last visited on Sep. 4, 2002, two pages.

NASA, Glenn Research Center, "Acoustic Liquid Manipulation Improves Selective Plating Process," located at: <http://technology.nasa.gov/scripts/nls> last visited on Sep. 4, 2002, one page.

NASA, Glenn Research Center, "Acoustically Enhanced Electroplating Process," Alchemitron Corporation, located at: <http://technology.nasa.gov/scripts/nls> last visited on Sep. 4, 2002, one page.

NASA, Lewis Research Center, (Aug. 1998). "Technology Opportunity: The Directional Electrostatic Accretion Process," Materials & Structures MS-200-1, located at: <http://technology.nasa.gov/scripts/nls> last visited on Sep. 4, 2002, two pages.

NASA, Lewis Research Center, (Aug. 1998). "Technology Opportunity: Liquid Manipulation by Acoustic Radiation Pressure," Combustion & Fluids CF-070-1, located at: <http://technology.nasa.gov/scripts/nls> last visited on Sep. 4, 2002, two pages.

Rodwell, J.D. and McKearn, T.J. (1985). "Linker Technology: Anitbody-Mediated Delivery Systems," *Biotechnology* 3:889-894.

Southern, E.M. and Maskos, U. (1990). "Support-Bound Oligonucleotides," *Chemical Abstracts* 113(17):835 Abstract No. 152979r.

US 5,828,388, 10/1998, Cleary et al. (withdrawn)

\* cited by examiner

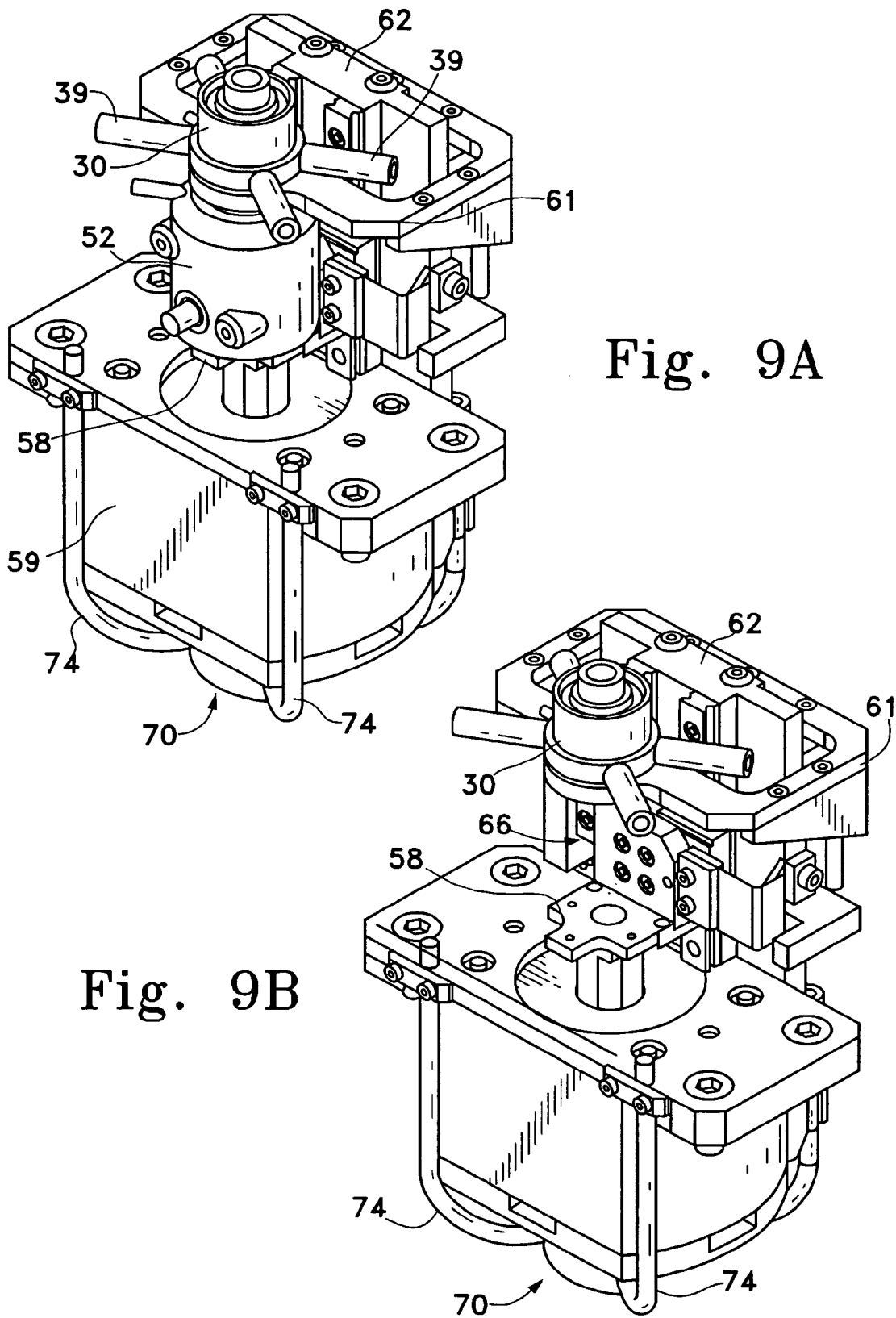

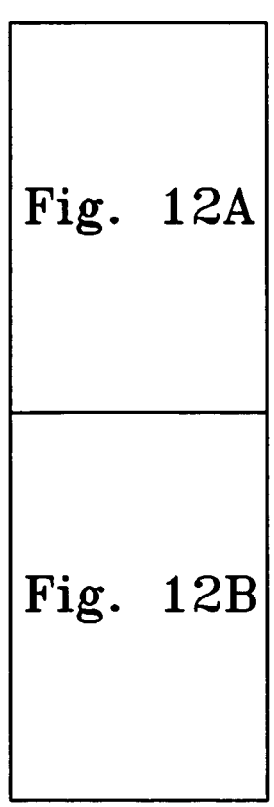

Supplying a coupling fluid to a distal end of the wave-guide (this step may also take place after or simultaneously with the maintaining a negative pressure step; furthermore this may be a continuous process where coupling fluid is continuously supplied to the distal end of the wave-guide)

Maintaining a suction in the area surrounding the distal end of the wave-guide to remove at least a portion of the coupling fluid at the distal end of the wave-guide (this step may further comprise maintaining a constant suction; alternatively, this step may comprise maintaining a constant suction in the immediate area surrounding the the coupling fluid inlet)

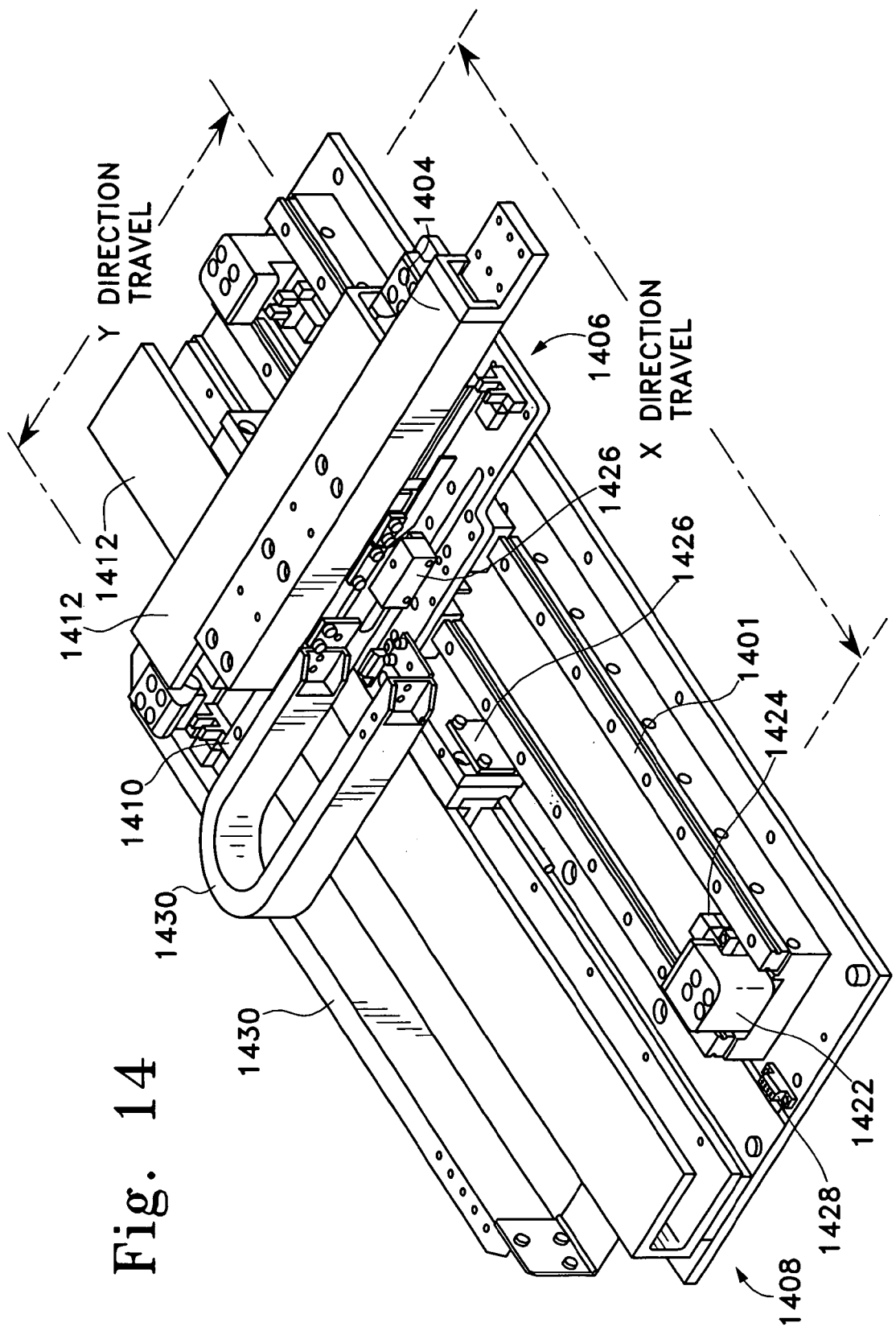

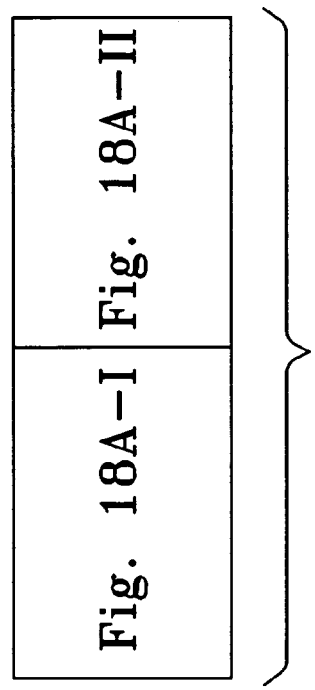
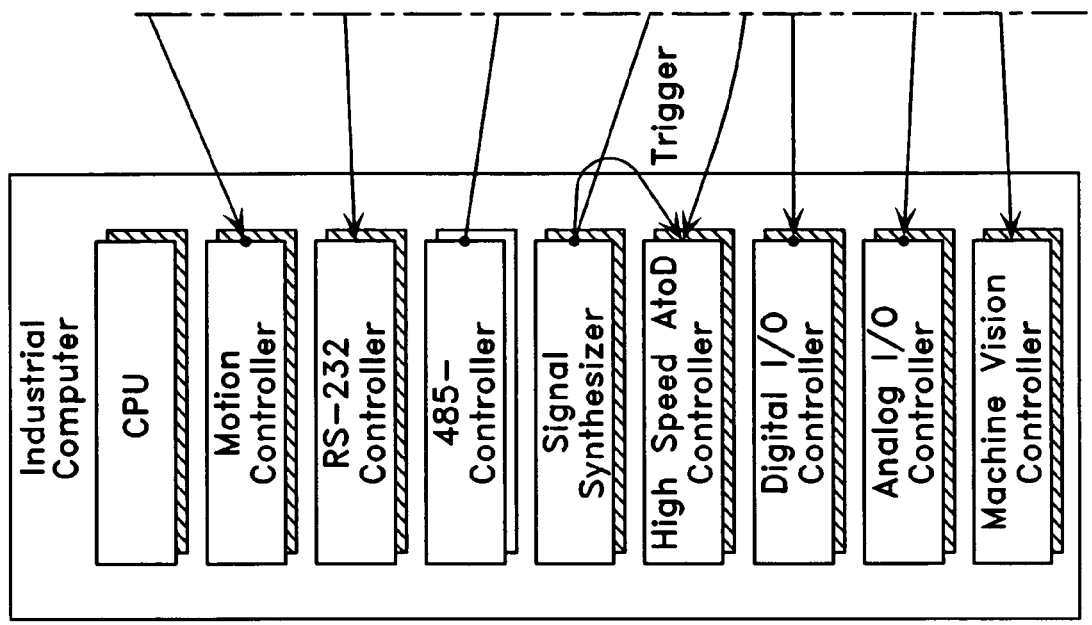
Fig. 18A-I

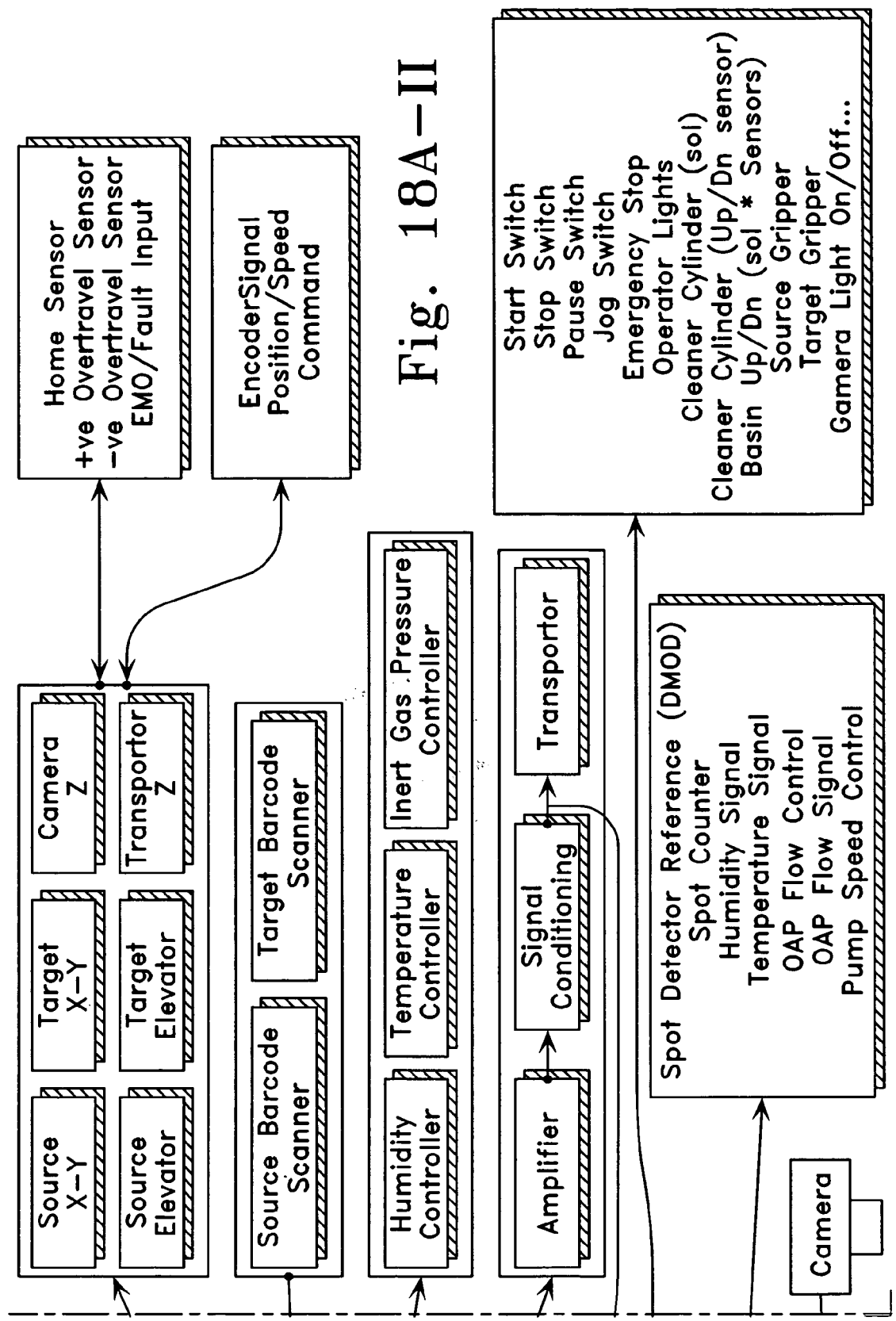
Fig. 18A-II

Fig. 18B-I

| Fig. 18B-I | Fig. 18B-II |

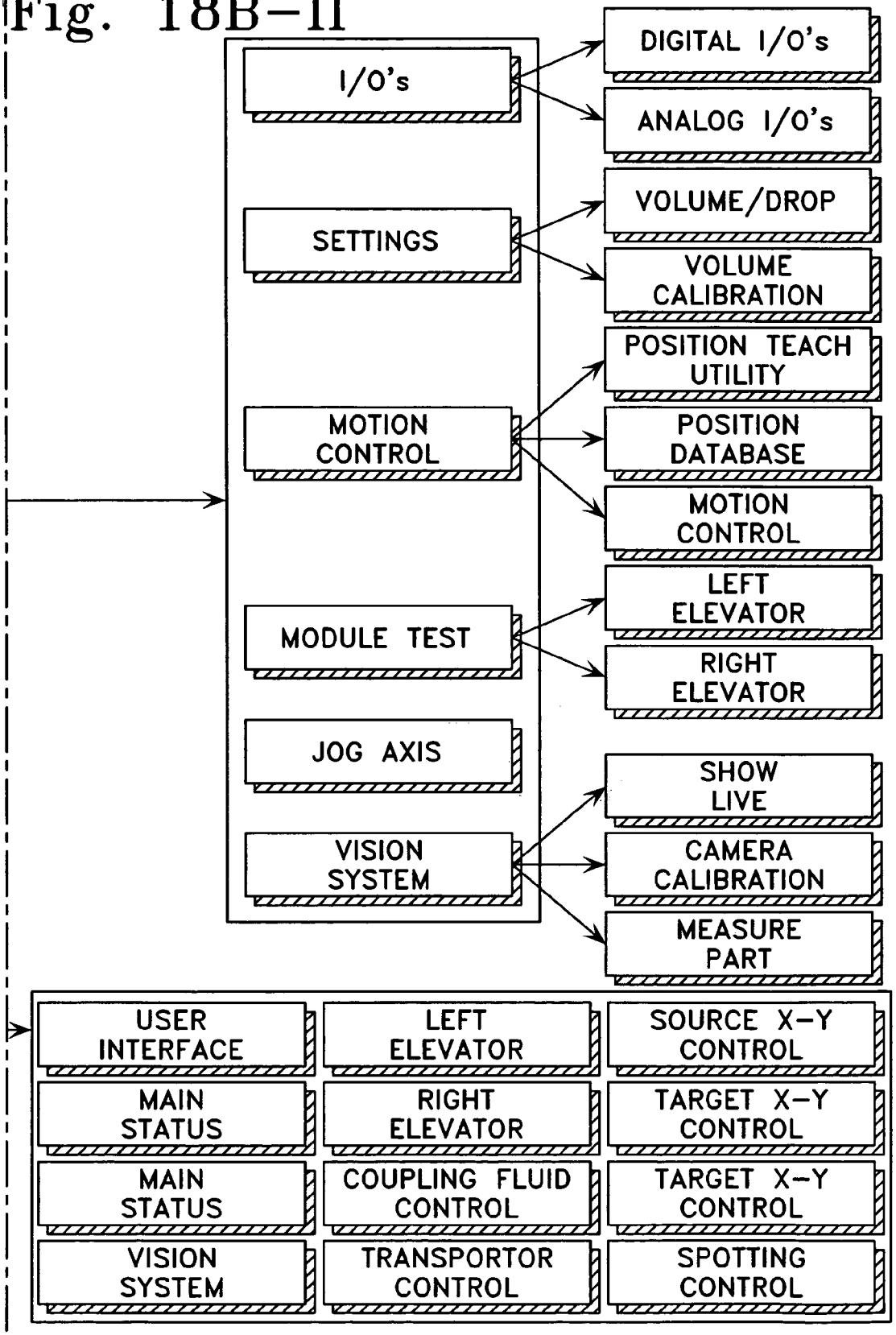
Fig. 18B-II

WAVE GUIDE WITH ISOLATED COUPLING INTERFACE

CROSS-REFERENCE TO RELATED APPLICATIONS

This application is claiming the benefit of priority to U.S. provisional application Ser. No. 60/429,778 entitled "WAVE GUIDE WITH ISOLATED COUPLING INTERFACE" filed on Nov. 27, 2002, U.S. provisional application Ser. No. 60/434,756 entitled "WAVE GUIDE WITH ISOLATED COUPLING INTERFACE" filed on Dec. 18, 2002, and U.S. provisional application Ser. No. 60/435,767 entitled "APPARATUS FOR HIGH-THROUGHPUT NON-CONTACT LIQUID TRANSFER AND USES THEREOF" filed on Dec. 19, 2002, each of which is incorporated herein by reference in its entirety.

FIELD OF THE INVENTION

The present invention generally relates to acoustic droplet ejection systems and in particular to an improved coupling interface design for use in an acoustic droplet ejection system.

DESCRIPTION OF RELATED ART

Many methods for the precision transfer and handling of fluids are known and used in a variety of commercial and industrial applications. However, most of these methods require the direct contact of transfer device with the source fluid, thus increasing the risk of cross contamination between various fluid sources. The presently burgeoning industries of biotechnology and biopharmaceuticals are particularly relevant examples of industries requiring ultra-pure fluid handling and transfer techniques. Not only is purity a concern, current biotechnological screening and manufacturing methods also require high throughput to efficiently conduct screening of compound libraries, synthesis of screening components, and the like.

Fluid transfer methods that require contacting the fluid with a transfer device, e.g., a pipette, a pin, or the like, dramatically increase the likelihood of contamination. Many biotechnology procedures, e.g., polymerase chain reaction (PCR), have a sensitivity that results in essentially a zero tolerance for contamination. Accordingly, a non-contact method for fluid transfer would result in a drastic reduction in opportunities for sample contamination.

Furthermore, fluid transfer methods that require physical contact with source fluids also require elaborate mechanical controls and cleaning mechanisms, and do not conveniently and reliably produce the high efficiency, high-density arrays.

Biotechnology screening techniques may involve many thousands of separate screening operations, with the concomitant need for many thousands of fluid transfer operations in which small volumes of fluid are transferred from a fluid source (e.g., a multi-well plate comprising, for example, a library of test compounds) to a target (e.g., a site where a test compound is contacted with a defined set of components). Thus, not only the source, but also the target may comprise thousands of loci that need to be accessed in a rapid, contamination-free manner.

Similarly, biotechnology synthesis methods for the generation of tools useful for conducting molecular biology research often require many iterations of a procedure that must be conducted without contamination and with precision. For example, oligonucleotides of varying lengths are tools that are commonly employed in molecular biology research applications, as, for example, probes, primers, anti-sense strands, and the like. Traditional synthesis techniques comprise the stepwise addition of a single nucleotide at a time to a growing oligomer strand. Contamination of the strand with an erroneously placed nucleotide renders the oligonucleotide useless. Accordingly, a non-contact method for transferring nucleotides to the reaction site of a growing oligomer would reduce the opportunity for erroneous transfer of an unwanted nucleotide that might otherwise contaminate a pipette or other traditional contact-based transfer device.

In order to meet these needs, methods have been developed utilizing acoustic waves to eject fluids out of source reservoirs. The acoustic droplet ejection systems allow for a non-contact method for the precision-transfer of small amounts of fluid in a rapid manner that is easily automated to meet industry needs. An exemplary non contact system for ejecting liquid droplets to a target location is described in U.S. patent application, Publication Ser. No. 2002/0,094,582 A1, published Jul. 18, 2002, entitled "Acoustically Mediated Fluid Transfer Methods And Uses Thereof" and it is incorporated herein by reference in its entirety.

However, a major obstacle in developing a reliable and cost-effective fluid ejection system lies in the development of an appropriate coupling interface for the wave-guide. As seen in FIG. 2 of the U.S. patent application Publication Ser. No. 2002/0,094,582, coupling medium 20 is distributed across the entire bottom surface of fluid containment structure 30. This may increase the difficulty in changing fluid containment structure and changing alignment of the acoustic liquid deposition emitter. Dispersion or wicking of coupling fluid from the edge of the source fluid containment structure may also be a problem in this design.

Another example of non contact system for ejecting liquid droplets to a target location is described in U.S. patent application, Publication Ser. No. 2002/0,037,359 A1, published Mar. 28, 2002, entitled "Focused Acoustic Energy In The Preparation of Peptide Arrays." As seen in FIG. 1 of the Ser. No. 2002/0,037,359 publication, the coupling medium 41 extends beyond the edges of the reservoir or fluid containment structure. The structure described in this application makes it difficult to replace or change source fluid containment structure without inadvertently spilling or splattering the coupling liquid since the coupling medium is not isolated. In addition, since the coupling medium 41 expands across the base 25 of the reservoir, it is also difficult reposition the acoustic radiation generator 35 while maintaining the coupling interface provide by the coupling medium 41.

Yet another example of the droplet ejection systems which utilize acoustic energy is U.S. Pat. No. 4,751,530 issued Jun. 14, 1988 to Elrod et al. The '530 patent describes an acoustic print head 11 having an array of spherical lenses 12$a$-12$i$. The print head 11 is submerged in a pool of ink 16, as shown in FIG. 2. The lenses 12$a$-12$i$ may be acoustically isolated from each other "such as by providing narrow slots 66 between them which are filled with air or some other medium having an acoustic impedance which differs significantly from the acoustic impedance of the substrate 22 such that an acoustic mismatch is created." See col. 5, line 62 to col. 6, line 8 and FIGS. 7-8 of U.S. Pat. No. 4,751,530. The slots 66 however do not extend the full thickness of substrate 22 nor do the slots surround each side of the substrate 22. Thus, there is no full isolation of the waveguide or acoustic propagation path. Because this design requires that the acoustic wave generation units be immersed in the source fluid, different fluids would require separate wave generation and propagation paths positioned in each pool of fluid. Another associated consequence of immersing the acoustic wave generation unit in the source fluid is that the same wave generation and propagation unit can not be used with separate fluid containment structures without the risk of cross contamination. In addition, since this particular design requires the source fluid to be distributed over an array of emitters, it does not need nor suggest the use of a coupling interface.

Existing non-contact liquid transfer systems are limited and do not provide for high-throughput transfer of liquids and their ability to generate high-density arrays in an efficient and reliable manner are also limited. A system that is capable of transferring a large number of liquids from their receptive locations in a high density array to target locations comprise of another high density array in a predetermined pattern with precision, not only may be used for generating high-density arrays for screening or synthesis of chemical compound, the system itself may be implemented as the platform for synthesis and/or screening.

Accordingly, there exists a need in the art for a non-contact method for the precision transfer of small amounts of fluid in a rapid manner that is easily automated to meet industry needs. A system that is capable of efficient transfer of liquids from any location in a first set of well plates to a second set of well plates in any order and pattern, may provide significant advantages in high-throughput liquid transfer, high-throughput biological/chemical/biochemical synthesis and/or high-throughput screening of biological/chemicals/biochemical compounds.

SUMMARY OF THE INVENTION

Accordingly, the invention in one embodiment provides an acoustic wave source, which is capable of ejecting liquid from a pool of source liquid onto a target location. Another embodiment of the present invention provides for a mechanism to align any location in an array or arrays of source fluid pools with any location in an array or arrays of target locations, such that liquid may be transferred from any location in the source liquid array or arrays to any location in the target location array or arrays. Yet another embodiment of the present invention provides an image detection system for controlling and/or monitoring the fluid transfer between the source liquid array and the target location array. The image detection system may be implemented for aligning a source liquid array with a target location array, monitoring the transfer of liquid, or monitoring/recording reactions/condition within the target location after the completion of liquid transfer. Various other embodiments and advantages of the present invention will become apparent to those skilled in the art as more detailed description is set forth below.

In one aspect of the present invention, an integrated system is provided for non-contact transfer of small amounts of liquid materials from source vessels (or source fluid containment structures) to target vessels (or target devices, plates or surfaces). "Non-contact," as used herein, means that a source liquid is transferred or removed from a source pool of liquid without contacting the source liquid with a transfer device. Because energy waves, such as acoustic waves, are used to force one or more drops of liquid out of the source pool and into a target region, no physical device needs to come into contact with the source pool to effectuate the transfer of the liquid.

In another aspect of the invention, an apparatus is provided for random-access liquid transfer. The random-access liquid transfer capability may allow transfer of a liquid from any location within a matrix of source fluid vessels to any location within a matrix of targets. For example, the source vessels may comprise a series of well plates, and the target vessels may comprise a separate series of well plates. Liquids from different wells (which may be from the same plate or a different plate) may be transferred to different or same target wells (which may be from the same plate or different plate) one after another in any sequence or pattern that is prescribed by the user. Unlike most system on the market, which require linear sequential access of source materials and has a predefined pattern of delivery to the target locations, this apparatus may allow non-linear and/or random access of both source liquid pools and target locations. That is to say, the user may eject fluid from any source liquid location in the source vessels into any target location in the target vessels, and the next source fluid location and target location may also be any source liquid location and any target location in their receptive arrays of vessels. The selection of the source liquid location and target location is completely independent of the previous source/target location selections.

In yet another aspect of the invention, the fluid transfer apparatus may allow transfer of predefined volume of liquids from a source vessel to a target vessel. The apparatus may be designed such that in a series of ejections, different volumes of liquid are transferred in each ejection. The user may also program the apparatus to deliver a series of liquid droplets of various sizes that are predefined by the user. As it will be apparent to one skilled in the art, various variations of the apparatus may be utilized for drug discovery or chemical synthesis.

In one variation, the non-contact, random-access liquid transfer apparatus is comprised of a) an acoustic emitter device, b) two X/Y linear stage assemblies, c) two handling devices, one each attached to the X/Y stage assemblies, d) two storage queues, one for source vessels and the other for target devices, e) a image detection system, f) machine controls, electronics and software, g) frame and support structure, and h) environment and safety enclosure. All of the system's sub-assemblies and components may be built upon an internal skeleton-like framework. Alternatively, the deferent sub-assemblies and components may be positioned by separate frame or supporting structure.

The acoustic emitter may provide the energy waves for ejecting liquid out of a source vessel and onto a target device. The X/Y linear stage assemblies along with their corresponding handling device may retrieve source vessel and target device from the storage queues and align the source vessel and the target device above the acoustic emitter. The storage queues may hold multiple source vessels and target device, and may be capable of delivery any of the source vessels or target devices to a predefined location where specific source vessel or target device may be accessed by the handling device attached to its X/Y linear stages. The image detection system may provide signal feedback to the machine controls so that appropriate alignment of source vessel and target vessel with the acoustic emitter may take place. The image system may be used for pre-ejection calibration, and it also may be implemented to monitor the ejection process. Furthermore, the image system may also be used for post ejection verification/measurements of physical and/or chemical parameters within each individual target location. Machine controls, electronic and software, may provide overall control of the various components within the liquid transfer apparatus. The machine controls may provide feedback control so that appropriate source vessel and target device are retrieved from the storage queue and positioned above the acoustic emitter appropriately. The machine controls may further define the amount of energy delivered by the acoustic emitter and the location of the focus of the acoustic wave been emitted. A software algorithm may be implemented along with machine controls such that specific source/target alignment and ejection sequence is followed in a high-throughput liquid transfer process. A frame and support structure may be provided for integrating the various components in the liquid transfer apparatus. Various moving mechanisms may be connected to a primary frame such that alignments and/or calibration may be easily carried out between various moving parts. An environment and safety enclosure may be provide to control/monitor various environment parameters and prevent unintended user intervention during system operation. Various design variations may be implemented in the liquid transfer apparatus.

[a] Acoustic Emitter Device

An acoustic emitter device is provided for generating and propagating an acoustic wave in a direction defined by a wave-guide. The wave-guide may comprise of a continuous piece of wave conducting medium for transferring an energy wave from the wave generation source to the coupling liquid. Alternatively, the wave-guide may comprise a plurality of interconnecting parts. The wave-guide may further comprise a focusing device (e.g. lens) at one end for focusing the energy wave as it exits the wave-guide. Materials may be selected for optimizing the transfer of a particular kind of wave. In one variation, the wave-guide is fabricated with materials for facilitating transfer of an acoustic wave. For example, the acoustic wave-guide may be constructed of aluminum, silicon, silicon nitride, silicon carbide, sapphire, fused quartz, glass, a combination there of, or the like. In one variation, a separate lens may be placed on the distal end of the wave-guide for forming a focused acoustic beam. Alternatively, the distal end of the wave-conducting medium may have a concave surface or other structural features for facilitating the focus of the wave as it exits the wave-conducting medium. Other wave conducting channels or medium that are well known to one skilled in the art may also be adapted for constructing the wave-guide.

A fluid basin may be provided for supplying coupling liquid to the distal end of the wave-guide and/or removing excess coupling liquid from the area surrounding the wave-guide. The fluid basin may comprise a structure that surrounds the wave-guide and has a channel for supplying coupling liquid and a separate channel for providing suction to remove excess coupling liquid. The "suction channel" is a channel through which liquid can be removed or withdrawn. A pressure gradient may be maintained across the two ends of the suction channel to facilitate removal of the liquid. A vacuum generator or a suction source may be connected to one end of the suction channel. In another variation, a suction generator, for generating a pressure pocket having a pressure lower than the pressure in the ambient or surrounding environment, may be attached to one end of the suction channel to facilitate the removal of the liquid from the other end of the suction channel.

In another variation, the wave-guide may be supported within a housing. The wave-guide housing and the wave-guide may move as a unit, independent of a fluid basin that provides the coupling liquid and fluid suction.

In yet another variation, a coupling liquid outlet surrounds the wave-guide, and a constant negative pressure is maintained around the immediate area surrounding the coupling liquid outlet. This may be achieved with a vacuum generator to create the negative pressure and routing the negative pressure source to a cavity that surrounds the coupling liquid outlet. The negative pressure area surrounding the wave-guide may create a suction, which facilitates removal of excess coupling liquid from the area surrounding the wave-guide.

Alternatively, the wave-guide may be positioned within a lumen. The lumen may be flooded with coupling liquid so that the tip of the wave-guide is covered with coupling liquid. A constant negative pressure may then be maintained around the lumen. The constant negative pressure may also be delivered through a channel surrounding the lumen or through a cavity surrounding the lumen. The channel or lumen may be connected to a negative pressure source. In another variation, two coaxial channels are implemented for providing the coupling liquid and the suction. The wave-guide may be positioned within the inner lumen and enough space may be provided between the walls of the inner lumen and the wave-guide for coupling liquid to flow. The outer lumen may be connected to a negative pressure source. In the above variations, the wave-guide may be fixedly positioned within the inner lumen or moveably positioned within the inner lumen.

A fluid pump may be used to supply fluid to the inner lumen or the coupling liquid outlet. A fluid reservoir may be connected to a fluid pump for supplying the coupling liquid. The fluid pump may be a peristaltic pump, a diaphragm pump, a centrifugal pump, a piston pump, a positive displacement pump or other active fluid transfer mechanisms well known to one skilled in the art. Alternatively, other fluid supply sources, including passive fluid supply sources, may also be implemented to supply fluid to the inner lumen. For example, the coupling liquid may be provided through gravitational force by displacement of a fluid container at an appropriate height. Connections may be provided for the fluid to flow from the liquid container to the inner lumen or the coupling liquid outlet. In this variation, the fluid container may be a separate container from the container for capturing returning coupling liquid from the negative pressure suction.

The negative pressure source may comprise a mechanical fluid pump, a diaphragm pump, a centrifugal pump, a vacuum generator or other flow generator well known to one skilled in the art. The negative pressure source may also be created by a siphon, which compresses air through a venturi whose throat has an opening to create a low-pressure source at the throat without the use of any moving mechanical parts.

It is understood that in this disclosure and related amendments the term "connect" and "connecting," when used in the context of establishing a connection with a fluid source, a vacuum source or a pump, may include providing additional medium such as a tubing or a channel to achieve the connection between one element and another element. For example, a fluid pump connected to a channel may include a fluid pump that is connected to the channel through tubing to allow fluid transfer between the fluid pump and the channel, or the fluid pump may be directly connected to the channel.

In another variation, the coupling liquid may be supplied to the tip of the wave-guide through one or more channels positioned next to the wave-guide, and the negative pressure may be provided through one or more channels positioned next to the coupling liquid supply channels. For example, a coupling liquid outlet may surround the wave-guide, and a plurality of channels may surround the coupling liquid outlet for removing excess fluid from the distal end of the wave-guide assembly.

The wave-guide may have a cross-sectional area of 1 square mm to 10000 square mm. Preferably, the cross sectional area of the wave-guide is between 2 square mm to 800 square mm. More preferably, the cross sectional area of the wave-guide is between 3 square mm to 150 square mm. Most preferably, the cross sectional area of the wave-guide is between 20 square mm to 25 square mm.

The coupling liquid cross sectional area above the wave guide is preferably isolated to an area less than twenty times the cross-sectional area of the wave-guide, more preferably less than ten times the cross-sectional area of the wave-guide, even more preferably less than 3 time the cross-sectional area of the wave-guide. The coupling liquid area above the wave-guide may be isolated to an area about the same as the cross-sectional area of the wave-guide.

In the variation where a negative pressure surrounds the wave-guide, the area surrounded by the negative pressure region (including the wave guide and negative pressure region itself) is preferably between 3 square mm to 30000 square mm, more preferably between 3 square mm to 150 square mm, even more preferably between 60 square mm to 70 square mm. In one variation, the area surrounded by the negative pressure region is design to be about three times the cross-sectional area of the wave-guide. For example, the wave-guide may have a cross-sectional area of 21 square mm and the corresponding area surrounded by the negative pressure region (including the wave-guide and the negative pressure region itself) may be 64 square mm. In another variation, the area surrounded by the negative pressure region is 1.62 times the cross-sectional area of the wave-guide.

In another aspect of the invention, the wave-guide may be moveably disposed within the wave-guide assembly such that the wave-guide focus may be adjusted along a linear axis. The wave-guide assembly may comprise of a wave-guide positioned within a fluid basin, and the fluid basin may be configured to supply coupling liquid to the distal end of the wave-guide. In one variation, a fluid basin surrounding the wave-guide may be isolated from the wave-guide such that the wave-guide may move on a linear path independent of the fluid basin. This may allow the source fluid containment structure to maintain a constant gap from the fluid basin while the wave-guide focus is being adjusted. This constant gap may aid in maintaining the fluid coupling while the focus of the wave-guide is being adjusted. In addition, this design may also allow higher speed of movements of the source fluid containment structure in the X-Y plane, while allowing the source fluid containment structure to maintain contact with the coupling liquid.

The fluid basin surrounding the wave-guide may additionally include a trough for collection of excess coupling liquid that is not captured by the outer lumen or suction channel. The trough may be a formed by a lip surrounding the fluid basin. Alternatively, the trough may comprise a groove surrounding the negative pressure area. A channel for draining fluids from the trough may be provided. In addition, this draining channel may be connected to a negative pressure source for facilitating removal of fluids in the trough.

In another aspect of the invention, a fluid compensation mechanism is provided to offset the displacement of the wave-guide during focus adjustment so that fluid coupling between the tip of the wave-guide and the bottom of the source fluid containment structure may be maintained. In one variation, the coupling liquid is transferred back and forth through a flow line to a fluid displacement device (e.g., piston pump). The fluid displacement device may be coupled to the displacement mechanism moving the wave-guide to achieve synchronization. For example, the same motor that positions the wave-guide may actuate the fluid displacement device, so that coupling liquid displacement may be synchronized with the movement of the wave-guide. In another variation, a mechanically separate mechanism may provide the coupling liquid displacement. In addition, an electronic control mechanism may be provided to control the coupling liquid displacement and the wave-guide displacement. For example, a computer may be used to provide control and synchronization.

The source fluid containment structures may be well plates or microtiter plates that are commonly used in the biotech field, for example well plates having 384 wells or 1536 wells may be utilized. Other fluid containers such as capillaries (e.g., capillary arrays), a flat plate with isolated regions of liquids, and the like may also be used. Furthermore, the source fluid containment structure may also have channels or micro-channels embedded in the structure for supplying the wells with source fluids as needed. In addition, gates or valves may be integrated with these fluid supply paths for controlling the flow and/or the level of fluids in the wells. Sensors and electronic control mechanisms may also be implemented for managing the source fluid and maintaining the fluid levels in the wells.

A moveable stage may be provided for positioning the source fluid containment structure. Actuators, motors, or other displacement devices may be implemented with electronic control mechanisms (e.g. a computer or a feed back control circuitry) for positioning and aligning the desirable well in the source fluid containment structure over the wave-guide after each ejection.

A frame may be provided for positioning the fluid basin around the wave-guide. The frame may be connected to an independent stage or an existing structure (e.g., a skeleton framework built into the fluid ejection system) in the fluid ejection system. The fluid basin may be coupled to the frame in such a way as to allow some degree of X-Y movement but no movement in the Z direction. In one variation, bearings are provided to remove any side loads that could be imparted on the wave-guide due to the fluid basin and wave-guide misalignment, as one skilled in the art would appreciate.

A computer or electronic controller may be adapted for synchronizing different mechanisms in the fluid ejection system and/or controlling the size and direction of the ejection. The computer may be programmed to eject fluids out of selected wells on the source fluid containment structure in a particular sequence. Feedback mechanisms, such as sensors or other detectors, may be implemented in the computer controlled fluid ejection system to improve the performance and capability of the system.

A method for utilizing a negative pressure area or suction surrounding a wave-guide for isolating the coupling liquid is also contemplated in this disclosure. In one variation, the method includes the process of providing a wave-guide, supplying a coupling liquid to the distal end of the wave-guide, maintaining a negative pressure in an area surrounding the wave-guide to remove excess coupling liquid, directing an acoustic wave through the wave-guide toward the distal end of the wave-guide, and allowing the acoustic wave to pass through the coupling liquid, the source containment structure and into the source fluid. In another variation, the method further includes repositioning of a source fluid containment structure (e.g., a well plate) above the wave-guide to allow ejection of a different source fluid from a different reservoir in the source fluid containment structure. In yet, another variation, the position of the wave-guide may be adjusted to reposition the focus point of the acoustic wave, and may further include fluid displacement device for making appropriate compensation to the volume of the coupling liquid on top of the wave-guide in order to maintain the coupling between the wave-guide and the source fluid containment structure. The method may also include the step of maintaining a constant distance between the fluid basin and the bottom surface of the source fluid containment structure as the source fluid containment structure is re-positioned between individual reservoirs containing source fluids.

[b] Droplet Steering Mechanism

In another aspect of the invention, a droplet steering mechanism may be integrated within the non-contact liquid transfer apparatus to maintain, correct or adjust the trajectory of liquid ejected out of the source liquid container. The steering mechanism may be placed between the source liquid container and the target device to assist the ejected liquid to reach its intended target. The steering mechanism may also be aligned with the acoustic ejector to maintain or adjust the flight path of the ejected droplet so that the ejected droplet may stay on the Z-axis of the system.

In one variation, gas or air flow is directed through a throated structure to steer the trajectory of the ejected liquid droplet. For example, the throated structure may comprise a nozzle defining a throat, which may have an inlet or entrance port and a preferably smaller outlet or exit port. A venturi structure may also be used, in which case the inlet or entrance port may open into a nozzle which converges to a narrower throat and reopens or diverges into a larger outlet or exit port.

In the case of a nozzle defining a throat having an inlet or entrance port and a smaller outlet or exit port, the throat preferably converges from a larger diameter inlet to a smaller diameter outlet. Through this throat, a vectored or directed gas or air stream may be directed into the inlet to be drawn through the structure. The gas or air stream is preferably driven through the system via a pump, either a positive or negative displacement pump, such as a vacuum pump. The gas or air stream may also pass through a heat exchanger that is connected to the nozzle. The heat exchanger may be used to maintain or change the temperature of the gas or air stream. This in turn may be used to control the temperature of the droplets through convective heating or cooling as the droplets traverse through the nozzle. As the gas or air stream approaches the outlet, the gas or air may increase in velocity and is preferably drawn away from the centerline of the nozzle through a connecting deviated air flow channel. The gas or air stream may be drawn away from the throat at a right angle from the centerline of the nozzle or at an acute angle relative to the nozzle centerline. The gas or air stream may then continue to be drawn away from the throat and either vented or recycled through or near the inlet again. The gas used may comprise of various gases well known to on skilled in the art that are suitable for displacing liquids (e.g. nitrogen, carbon-dioxide, helium, etc. or a combination thereof). The gas may comprise any number of preferably inert gases, i.e., gases that will not react with the droplet or with the liquid from which the droplet is ejected. The gas may also comprised of several gases, a single gas, or a mixture of gas or air with other micro-particles or liquid mist. However, a gas that is highly reactive with the ejected liquid droplet may also be used. This reactive gas may comprise of several compounds, a single compound, or a mixture of gas or air with other micro-particles or fine liquid mist.

A droplet ejected from the surface of a liquid will typically have a first trajectory or path. The liquid is preferably contained in a well or reservoir disposed below the nozzle. To prevent overheating of the liquid within the reservoir during droplet ejection, the temperature of the well plate may be controlled actively, e.g., through conductive thermal heating or cooling, or the droplet generator may be used indirectly to control the temperature of each of the wells during droplet ejection. If the trajectory angle of the droplet relative to a centerline of the inlet nozzle is relatively small, i.e., less than a few tenths of a degree off normal, the droplet may pass through the outlet and on towards a target with an acceptable degree of accuracy. If the trajectory angle of the droplet is relatively large, i.e., greater than a few degrees and up to about ±22.5°, the droplet may be considered as being off target.

As the droplet enters the inlet off-angle and as it advances further up into the structure, the droplet is introduced to the high velocity gas or air stream at the perimeter of the interior walls of the nozzle. The gas or air stream accordingly steers or redirects the momentum of the droplet such that it obtains a second or corrected trajectory which is closer to about 0° off-axis. The gas or air stream at the connecting deviated air flow channel is preferably drawn away from the centerline of the nozzle and although the droplet may be subjected to the gas or air flow from the connecting deviated air flow channel, the droplet has mass and velocity properties that constrain its ability to turn at right or acute angles when traveling at a velocity, thus the droplet is allowed to emerge cleanly from the outlet with high positional accuracy. Throated structure may correct for droplet angles of up to about ±22.5°, but more accurate trajectory or correction results may be obtained when the droplet angles are between about 0°-15° off-axis.

To facilitate efficient gas or air flow through the throated structure, the throat is preferably surrounded by a wall having a cross-sectional elliptical shape. That is, the cross-sectional profile of the wall taken in a plane that is parallel to or includes the axis of the nozzle preferably follows a partial elliptical shape. The exit channels which draw the gas or air away from the centerline of the throat may also have elliptically shaped paths to help maintain smooth laminar flow throughout the structure. It also helps to bring the gas or air flow parallel to the centerline as well as maintaining a smooth transition for the exit flow as well as maintaining an equal exit flow on the throat diameter. This in turn may help to efficiently and effectively eject droplets through the structure.

In addition to the throated structure, alternative variations of the device may include a variety of additional methods and/or components to aid in the gas/air flow or droplet steering. For instance, the nozzle may be mounted or attached to a platform which is translatable in a plane independent from the well plate over which the nozzle is located. As the well plate translates from well to well and settles into position, the nozzle may be independently translated such that as the well plate settles into position, the nozzle tracks the position of a well from which droplets are to be ejected and aligns itself accordingly. The nozzle may be tracked against the well plate and aligned by use of a tracking system such as an optical system, e.g., a video camera or digital camera, which may track the wells by a tracking algorithm on a computer.

Additionally, an electrically chargeable member, e.g., a pin, may be positioned in apposition to the outlet to polarize the droplets during their travel towards the target. Polarizing the droplets helps to influence the droplet trajectory as the droplets are drawn towards the chargeable member for more accurate droplet deposition. Additionally, well inserts for controlling the ejection surface of the pool of source liquid from which the droplets are ejected may also be used in conjunction with the throated structure. Furthermore, various manifold devices may be used to efficiently channel the gas or air through the mechanism.

[c] X/Y Linear Stage Assemblies

The X/Y linear stages may be used to manipulate the source vessels and the target device above the acoustic emitter device. This may allow the liquid transfer apparatus to transport a liquid from any source location to any target location. In one variation, the X/Y linear stages, along with the elevator storage queue, provide the mechanism to position any well on any source vessel or target device above the acoustic emitter.

The X/Y linear stages may be sized accordingly to various stroke/travel specifications, as one skilled in the art would appreciate. The X/Y stage may be designed to complement the storage queues, the source vessels and/or the target device.

In one variation, the acoustic emitter device is in a fixed location, and with the assistance of the X/Y linear stage the source vessel and the target device are movable in the X/Y plane to selectively align a source well on the source vessel with the target well on a target device with the acoustic emitter. However, one skilled in the art would appreciate that other variations are also possible. For example, the position of the target device may be fixed, and the source vessel and the acoustic emitter device are allowed to move in the X/Y plane. Alternatively, the source vessel may be in a fixed position and the target device and the acoustic emitter are given freedom of movement in the X/Y plane. It is also within the contemplation of this invention that all three elements (the source vessel, the target device and the acoustic emitter) may move in the X/Y plan independent of each other. The X/Y plane movements may allow any source location to be aligned with any target location and the acoustic emitter. Only two of the three elements need to move to allow this dynamic alignment to take place.

In another variation, mechanisms may be provided to allow vertical movement of the source vessel, the target device and/or the acoustic emitter. An actuator may be provided to physically move the acoustic emitter. However, mechanisms may also be provided for adjusting the location of the focus for the acoustic beam without physically moving the position of the complete acoustic emitter unit.

The X/Y linear stage provides the mechanism to retrieve source vessels and target devices from their receptive storage queue and position them over the acoustic emitter. Other mechanisms for transferring objects (e.g. robotic arms) which can serve similar purpose may also be adapted in the liquid transfer apparatus. Although the object transfer mechanism describe herein only has two-dimensional degrees of freedom, one skilled in the art would appreciate that the object transfer mechanism may be modified to have additional degrees of freedom. For example, the linear stage may be adapted on an elevator to provide motion in the Z direction.

In another variation, two X/Y linear stages are provided, one for handling the source vessel and the other for handling the target device. The two linear stages may be arranged in a stacked configuration, one positioned above the other. The linear stages may be located behind the acoustic emitter device. In another variation, the X/Y stages may be arrange opposite to one another, one on each side of the transporter device. In this configuration, the X/Y linear stage may be able to transport the well plates from the front of the system to the back of the system. The X/Y linear stages may be positioned in various configurations, including implementing them as an interface with other external devices to facilitate automation. For example, the X/Y linear stages may extend beyond the main compartment holding the acoustic emitter, so that well plates may be retrieved from a separate storage system holding various well plates.

In addition to the two X/Y linear stages described above, additional X/Y linear stages may be added along with other transport assemblies such that multiple source and target well plates or substrate may be processed simultaneously. In one variation, separate sets of X/Y linear stage assemblies may be implemented to retrieve well plates from different storage queues containing different sets of chemical libraries. For example, the liquid transfer apparatus may be supported by three sets of X/Y linear stages interacting with three sets of elevator storage queues, each holding a different set of chemical library. Alternatively, one main storage queue may support multiple liquid transfer apparatus. For example, one storage queue containing a large chemical library may support three liquid transfer units that surround it. Each liquid transfer unit may have a X/Y linear stage that extends to the main storage queue for retrieving source well plates contain the chemical library. In addition, each liquid transfer unit may have its own target storage queue for storing its own sets of target wells, which may hold a predefined set of chemicals to be tested against the main chemical library. A system configured in this fashion may allow three sets of chemicals to be tested against one primary chemical library simultaneously. Various other configuration that are well known to one skilled in the art may be implemented to design scalable systems for large scale, high throughput production lines for chemical synthesis and/or lead compound screening.

[d] Handling Device—Attached to the X/Y Stage Assembly

The handling device may be an integral part of the X/Y linear stage assembly or it may be separate mechanisms that may be easily detached from the X/Y linear stage, depending on the design need of the overall system as one skilled in the art would appreciate. For example, the handling device may be a gripper assembly that may be easily detached from its X/Y linear stages. Single and/or dual axis mechanism may be utilized to manipulate a wide variety of well plates, substrates (e.g. glass plate, glass slides, polymeric plate), or liquid containment devices for holding source liquids or serving as target devices. Automated grippers that are commonly used in the industry to move well plates tend to lack precision repeatability in their ability to hold the well plates within the grippers in the same position every time. In applications where the handling devices are used to hold and align well plates in a precise manner, a device capable of holding and securing well plates in a consistent manner may provide significant advantages.

In one variation, the system aligns (or calibrate the amount of misalignment with a reference axis defined by the system) the well plate each time a well plate is picked up. This alignment process may be achieved through detecting and measuring two or more fiduciary points on a well plate to determine the amount of misalignment of the well plate. Base on this misalignment determination the system may then compensate with appropriate amount of displacement when moving the well plate so specific location, such as a well, may be lined up with a reference point on the system. With this approach, the system may also compensate for variation in well plate size since each well plate is aligned each time it is picked up by a handling device. In another variation, the alignment of each handling device is aligned once when it picks up the first well plate. This variation may be feasible if al the well plate are the same size and variation between well plate is minimal relative to the amount of precision of alignment required. In this approach, the ability for the gripper assembly to hold the well plates in a repeatable and consistent manner may be important to overall system performance.

In another variation, the handling device may apply forces in three separate axes such that an object held by the handling device may be forced into the same corner (or wedge) in a consistent manner. Other force/pressure distribution systems well known to one skilled in the art may also be implemented to ensure that when the same well plate is held by the handling device the well plate is held at the same position relative to the gripping mechanisms of the handling device.

The handling device may also be designed in such a way that pressure is applied to the object being held in the default position. Thus, in order for the controller to release the object (e.g. a well plate) being held by the handling device, power or energy must be delivered to active mechanisms (e.g. motor or piston) to force the gripping mechanism to release pressure on the object being held. Such a design may prevent accidental dropping of well plate during power failure or emergency shutdown of the system.

The handling device may have removable/replaceable finger attachments or extensions, which have costume shapes adapted to handle a particular kind of well plate or fluid container. This design feature may allow the system to be quickly customized to handle well plates or microtiter plates of various dimensions.

[e] Storage Queues

The storage queue may be a rack or other holding structures for storing a plurality of well plates, liquid containment structures, or target devices. In one variation, the storage queue comprises of one or more elevator assemblies. In each elevator assembly, there may be multiple source vessels and/or target devices. In one variation, two elevators are provided with one elevator storing all the source vessels and the other stores all the target devices. The elevator may move vertically to position the appropriate source vessel or target device for retrieval by the handling device.

The source vessel and target device may be well plates that are commonly used in the biotechnology industry. The source vessels and target device may also be any liquid containment structures, which is capable of holding a plurality of isolated pools of liquids, well known to one skilled in the art. The source vessels and target vessels may also be flat surfaces, which is capable of holding individual pools of liquids on its surface. Chemical coatings, such as hydrophobic or hydrophilic materials, may be implemented to improve liquid isolation on or in the vessels. The source vessel and target device may comprise of the same material. For example both the source vessels and the target devices may be well plates. Alternatively, the source and target vessels may be different materials. For example, the source vessels may be well plates and the target devices may be glass plates with coatings. It is also within the contemplation of this invention that source vessels may comprise of different liquid containment structures. For example, within the elevator holding the source vessels, some source vessels may be well plates and some vessels may be glass plates. The target vessels may also comprise of different liquid containment structures. Barcode or other markers may be provide on the source vessels and/or the target device so the liquid transfer system may track the well plates that are being handled by the system. By detecting the barcodes, the system may track the well plate in the storage queues. Sensors or other detectors may be positioned within the liquid transfer apparatus to read the markers or barcodes on the well plates and track the well plates while they are being handling by the liquid transfer system. The barcode or markers may also be used to track other source fluid containment structures or fluid receiving surface or containment structures that are implemented in the liquid transfer apparatus.

The storage queues (e.g. elevators) may be sized accordingly to meet various source vessel storage requirement. For example, the elevator may be sized to hold well plates of particular height/width/depth. The storage queues may also have a built-in mechanism for adjusting the vessel holder or slot for securing well plates of various sizes within the storage queues. Depending upon the type of source vessels used, an entire library of biological compounds may be stored in the storage queues. For example, an elevator with ten slots, each slot holding a well plate with 1536 wells, may hold a biochemical library with 15360 compounds.

In another variation, the storage queue may be a device with fixed drop-off locations for individual well plates. In this design, individual well plates may be fed to the liquid transfer apparatus by placing the well plate at the drop-off location. A transfer device, such as a robotic arm or a mechanical gripper may transfer the well plate from the drop off location to the fluid ejection location or the target location on top of the acoustic emitter. Well plates may be loaded onto the drop-off location by manual transfer or via robotic automation. In another variation, a separate storage/sorting device holding well plates may interface with the liquid transfer apparatus through the drop-off location by feeding and retrieving well plates from the drop-off location.

In yet another variation, the storage queue may comprise of rotating carousel type mechanisms. The carousel may provide rapid interchange of well plates. For example, the carousel may hold 1 to 8, or more, well plates and may be loaded/unloaded manually or with automation. In another design variation, the carousel may have multiple stack or levels. The carousel may also incorporate elevator mechanisms for facilitating access of well plates within the various levels in the carousel.

In one variation, when the storage queue are not being accessed by the gripper assembly, the storage queue may be lowered into a cavity or climate chamber, where environmental parameters (e.g., temperature, humidity) may be controlled. This climate chamber may also be filled a with specific gas to facilitate cell growth or initiate chemical reactions. The chamber may also be heated to increase the rate of chemical reactions taking place within the well plates.

[f] Image Detection System

The image detection system may comprise a vision system with variable focus capability. For example, in one variation, the image detection system may focus on three separate planes (e.g., the plane where the tip of the acoustic emitter is located, the plane where the source vessel is positioned, and the plane where the target device is located.).

The image detection system may have various focal depths depending on the particular design need, as one skilled in the art would appreciate. In one variation, the image detection system may comprise of a CCD camera, lenses for focusing images on the CCD and motorized mechanisms for adjusting the focus. In another variation, the image detection system comprises a fixed-focus vision system. The fixed focused system may be adjusted vertically by an actuator so that the focus location of the camera may be adjusted by shifting the position of the camera/lens unit. Other electronic hardware and/or software may be implemented to enhance image detection and/or provide automatic focus adjustments, as one skilled in the art would appreciate.

The image detection system may provide the input signal for the control mechanism of the overall system to align the source vessels and the target device. The image detection system may also be used to monitor and verify the fluid transfer process. For example, the image detection system may be used for quality control. One of the limitations in most of the gene array fabrication devices in the market is the inability to verify the quality of each printed DNA spot after it is printed. The image detection system may allow the fluid transfer apparatus disclosed herein to verify whether a drop of liquid was successfully transfer on to the target device in real time. For this application, the target device may comprise of transparent or translucent materials. Furthermore, the image detection system may further allow size of the delivered droplet to be measured. The volume of the liquid delivered may be calculated based on the diameter of the droplet.

The image system may also be used to monitor post delivery changes within the target device. For example, a well on the target device may contain chemical compound A. A liquid containing chemical compound B may be ejected out of a well in the source vessel, into the well on the target device which contain chemical compound A. Chemical compound A may react with chemical compound B and give off a fluorescent light. This fluorescent light may be detected and measured by the image detection system. A computer may determine the chemical reaction base on the color of the fluorescent or the intensity of the fluorescent detected. Other chemical/biochemical reactions and associated method for detecting and measuring the reactions, which are well known to one skilled in the art, may also be implemented in this liquid transfer apparatus.

Target device may also be pulled from the storage queue for the sole purpose of monitoring and/or tracking chemical reactions or biological/biochemical indicators with the image detection system. For example, proteins placed in various wells in a target well plate may be treated with different chemicals from a chemical library by ejecting different chemicals into each well on the target well plate. The target well plate may be incubated within the storage cue for a period of time before it is pulled from the storage queue and examined under image detection system.

[g] Machine Controls, Electronics and Software

A computer with associated electronics may be implemented to provide overall control of the liquid transfer system. Various computation device, processors, controller, etc., which are well known to one skilled in the art, may be configured to provide processing control to various components in the liquid transfer apparatus. Software and/or graphic user interface may also be implemented to provide control and/or monitoring functions to the system.

For example, system software may be programmed to define selective amounts of liquid to be transferred in each individual ejection. A graphic user interface may provide a user-friendly environment where the user can easily enter the desired liquid amount to be transferred in each ejection. When the program executes, it may control the amount of acoustic wave energy and/or the location of the wave-guide focus of the acoustic emitter, thus defining the amount of liquid being ejected.

The system controller may also be programmed by the user with instructions defining where, when and/or what volume of liquid to transfer during each ejection. Specific sequence of liquid transfer protocol may be fed into the computer and executed by the liquid transfer system. The user may also define the selective location of source liquid to be transferred into each well in the target well plates, and allow the computer to determine the optimum sequence of transfer. Because of the random-access liquid transfer capability described above, the liquid transfer system described herein does not have to transfer/eject fluid in a linear fashion (one well after another on the same row or column). Since the system may allow the user to select any source location from any well plate in the storage queue, and transfer it to any target location on any target well plate/substrate in the storage queue, software may be provide to calculate the optimal transfer sequence based on the pattern of the target well plate to be created (the end product) and calculate the most efficient transfer sequence.

Software may also be implement in the control system to allow efficient reformatting of well plate type (e.g., 384, 1536, etc.) to the same or different type of plates. In one variation, four 384 type well plates may be reformatted into one 1536 type well plate. For example, a 1536 well plate man be divided into four (4) equal quadrants of 384 wells. Liquids from each well of the 384 well plates would be transferred directly into a corresponding well of the target 1536 well plate. For instance, well plate #1 may be transfer to quadrant #1 of the 1536 target and keep all of the source wells in the same row/column order. In other words, take the four plates and combined them into one. In another variation, the liquids in the wells of well plate #1 may be scattered in any fashion to any 384 wells of the target 1536 plate. The wells of plate #2 would go to any of the remaining 1,152 wells, and so on. Again, four plates go into one, but now they are not in an ordered sequence that corresponds to the sequences on the original 384 well plates.

In addition, the system may also be implemented to reformat array density. For example, liquid may be extracted from a 1536 well plate to create an array of liquid spots within a 1 square cm area that corresponds to the array in the 1536 well plate.

In yet another variation, the system may randomly select source wells in a non-sequential fashion and dispense them into an array of target locations in a sequential or non-sequential format. For example, it may be used for "cherry picking" source well liquids and dispensing them in precise sequential locations within other assay well plates. In another example, it may be used for selecting source well liquids and dispensing them in precise sequential locations on porous or non-porous substrates.

[h] Database

In one aspect of the invention, a database is provided to manage user inputs and or instruction sets for transferring liquid from any source locations within a collection of source fluid containment structures to any target locations within a collection of target devices. "Database" as used herein means "a collection of data organized especially for search and retrieval by a computer. " The computer may collect and store data in the database during real time operation of the machine to facilitate resource distribution tracking and/or for further analysis. The database may contain information such as user defined liquid transfer map or sequence information, well plate IDs, well plate configurations, source liquid volumes, depth of liquids in each source well, source liquid type, source liquid surface tension, source liquid viscosity, source liquid location on the well plate, age of source liquid (e.g., when it was created), how often the source liquid has been accessed, first/last time source liquid was accessed, time-stamp and other information related to each liquid ejection (e.g., volume or size of liquid droplet transferred, amount of acoustic energy used for the transfer). Information in the database may be updated to track changes in the system. Furthermore, information may also be added to the database as needed.

In one variation, each source library, which is comprised of a series of well plates holding a library of chemicals or biochemical, has a corresponding database file describing the content of each source, its location and corresponding volume and/or fluid height. The user may provide information defining specific locations on the target plates and corresponding source liquid and the volume to be transferred onto each target location. Base on the information in these databases, the liquid transfer platform may generate a new liquid library on a series of target well plates (by selectively transferring liquids from the source well plates to the target well plates), and an output database containing corresponding information regarding liquids at each of the target locations (e.g., liquid source (identifying or destination information) and/or volume of liquid at each location). The output database may be stored on a removable data storage medium (e.g. floppy disk, removable hard disk, miniature USB disk, compact flash card, memory stick, etc.) so it may be transferred to a remote facility along with the new liquid library. Alternatively, the output database may be transferred to the remote facility through a computer network.

In another variation, an input data set or mapping profile is provided with information regarding specific source locations, volume of liquid to transfer from each location and corresponding target location where each defined volume of fluid is to be transferred. The data may be provided on a memory device or transferred onto the liquid transfer platform through network connections. Base on the information provided, the liquid transfer platform generates a set of target plates with the desired liquids in the predefined locations. An output database containing information regarding the liquids on the target plates and/or information tracking the transfer process (e.g. time-stamp, successfulness of the transfer, volume transferred, and/or volume remained in the source wells) may be provide for each set of output target plates.

The ability to track the volume of liquids transferred out of the source wells may allow the system to track the height of the liquid in each source well and thus allow efficient positioning of acoustic wave's focus. Furthermore, tracking the remaining volume of the liquid in the source wells as fluids are ejected from the source well may also allow more efficient utilization of resources.

The data base may also be utilized to track alignment and associated coordinate information. In addition, information regarding optimal focus location(s) for the acoustic waves and/or fluid depth (fluid height, fluid surface location, fluid volume) in each of the source fluid wells may also be maintained in the database. The information maintained in the database may be used to speed the process of well plate alignments and facilitate the positioning of the wave-guide during each fluid ejection cycle.

The database may also be implemented to provide feedback and/or verification of the transferred liquids, which may also include volume information. Error recovery algorithm or protocols may be implemented along with the database to improve or manage the output liquid arrays' quality. For example, error recovery mechanisms may be applied to verify the detection of source liquid level and/or droplet ejection. The error recovery mechanisms may implement necessary correction measures when liquid level detection failed or when droplet ejection did not reach its intended target.

As described earlier, the non-contact liquid transfer apparatus may be configured to function with multiple database. For example, the apparatus may utilize a source library database and a mapping database, and generates an output library database. However, it is also possible to configure the apparatus to retrieve and store all the information from a single database.

In addition, when multiple liquid transfer apparatuses are being operated at the same time. All the liquid transfer apparatuses may be linked to a central computer with a centralized database through a computer network. The network of liquid transfer apparatuses may be configured such that all the source and target information are managed by the central computer and information are passed to the local database, which reside on the computer in each liquid transfer apparatus, when it is needed. The local database on each apparatus may maintain additional information that are unique to that particular apparatus (e.g., calibration information, operation or functional parameters for the various mechanisms in the apparatus, data regarding specific well plates that are being stored in the storage queues in that particular apparatus, etc.). The local computer operating on each apparatus may also retrieve additional data from the central computer to facilitate the operation of the liquid transfer apparatus.

[i] Frame and Support Structure

The frame and support structure may be provide for integrating the liquid transfer apparatus and its related supporting devices into one stand alone unit. Various mechanical sub units may be attached to a primary frame so that the different moving parts may be aligned and/or calibrated for precision interactions. Various compartments may be provided within the frame and supporting structure for housing supporting electronics and peripheral support devices. For example, a compartment may be provided for housing the system control computer. A separate compartment may house an environmental temperature control unit. Another compartment may be provided for housing a carbon dioxide supply source for supplying the primary enclosure or chamber with carbon dioxide gas.

[j] Environment and Safety Enclosure

An enclosure or chamber may be provide to house the liquid transfer apparatus. Various devices and mechanisms, which are well known to one skilled in the art, may be implemented to control specific parameters within the enclosure. Some of the environmental factors that may be monitored and/or controlled include, but are not limited to, temperature, humidity, air pressure, air flow, air cleanliness, destiny of particles inside the chamber (e.g. air filtration), light exposure levels (e.g., ambient light to complete blackout), lighting environment (e.g., constant UV light), and gas atmosphere compositions (nitrogen, argon, carbon dioxide, etc.). One or more of the above parameters may be monitored and/or controlled at the same time.

The enclosure or chamber may also prevent unintended user access during system operation. The access doors to the enclosure may be automatically locked, while various mechanisms in the liquid transfer apparatus are moving to prevent accidental injury to users. This may also prevent the user from prematurely accessing the source vessels or target devices before the completion of a programmed fluid transfer protocol. Emergency shutdown interface (e.g., a button or valve) may also be provided for terminating system operation.

BRIEF DESCRIPTION OF THE DRAWING

In the accompanying drawings, reference characters refer to the same parts throughout the different views. The drawings are intended for illustrating some of the principles of the wave-guide assembly and are not intended to limit the description in any way. The drawings are not necessarily to scale, emphasis instead being placed upon illustrating the depicted principles in a clear manner.

FIG. 9A illustrates a variation of a linear servomechanism for positioning the acoustic wave emitter module along a vertical axis. The mechanism includes a fluid compensation system for adjusting the volume of the coupling liquid at the distal end of the wave-guide to offset any changes caused by the movement of the wave-guide.

FIG. 9B illustrates the same linear servomechanism of FIG. 9A without the acoustic wave emitter module.

FIG. 14 illustrates one variation of an X-Y linear stage.

FIG. 18A shows one variation of a control systems block diagram.

DESCRIPTION OF THE INVENTION

Before describing the present invention, it is to be understood that unless otherwise indicated this invention is not limited to specific type of well plate, acoustic emitter, image detection system, or the like, as such may vary.

Liquid transfer is used herein as an example application to illustrate the functionality of the different aspects of the invention disclosed herein. It will be understood that embodiments of the present invention may be applied in a variety of processes and are not limited to providing liquid transfer. For example, variations of the present invention may be adapted for high throughput chemical synthesis or for screening lead compounds in a pharmaceutical discovery process. It will also be understood that embodiments of the present invention may be applied for ejecting various fluids, liquids, mixtures of liquids, liquid/compound mixture, biochemical, proteins, cells, etc., into various medium or space, and it is not limited to applications for distribution of liquids into a well plate.

Well plates are used in various examples herein to illustrate the functionality of different aspects of the innovation disclosed herein. It will be understood that embodiments of the present invention may be implemented with various other fluid containment structures, fluid receiving structures, vessels, porous surfaces, non porous surfaces, etc., and are not limited to well plates.

Acoustic wave is used herein to include all acoustic waves which are well known to one skilled in the art, whether they are continuous or intermittent waves. Various simple waveforms, complex waveforms, and wave-pulse are within the contemplation of this invention. Acoustic wave as used herein also includes a wave propagating as a result of concentration of energy in the vicinity of the surface of a piezoelectric substrate. The acoustic wave implemented in this invention is preferably has a frequency between 100 kHz and 1 GHz; more preferably, between 0.5 MHz and 200 MHz; and most preferably between 15 MHz to 50 MHz. The wavelength or frequency is preferably one that allows a droplet of about 10 micro-liter or less to be ejected from a pool of liquid.

It must also be noted that, as used in this specification and the appended claims, the singular forms "a," "an" and "the" include plural referents unless the context clearly dictates otherwise. Thus, for example, the term "a handling device" is intended to mean a single handling device or a combination of handling devices, "a chemical compound" is intended to mean one or more chemical compound, or a mixture there of.

To aid in understanding the invention, one variation of a liquid transfer apparatus is first described, followed by description of details on various components within the liquid transfer apparatus.

The System Platform

Figure 1A:
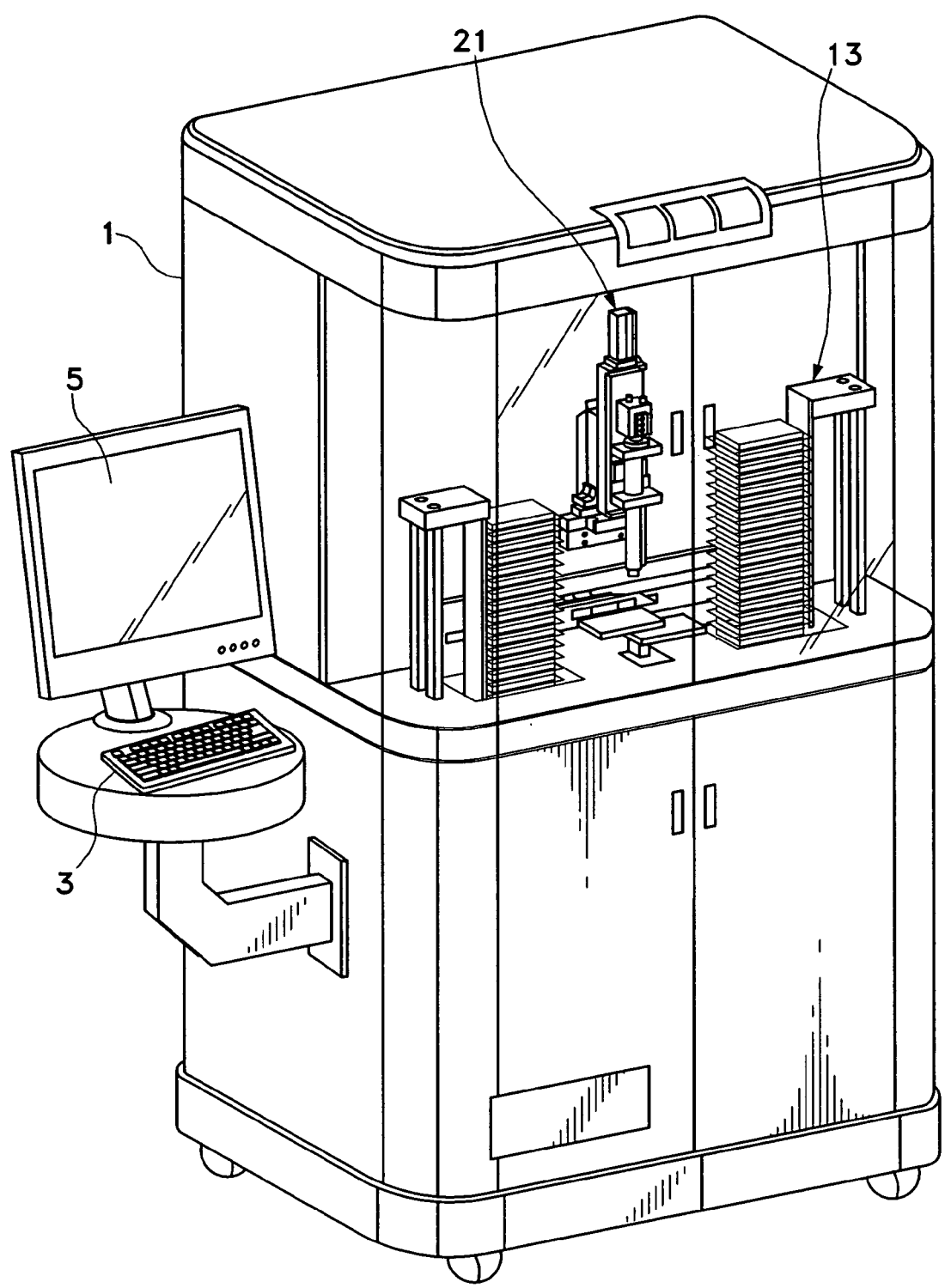
FIG. 1A illustrates one variation of an high-throughput non-contact liquid transfer apparatus with an integrated enclosure.
Figure 1B:
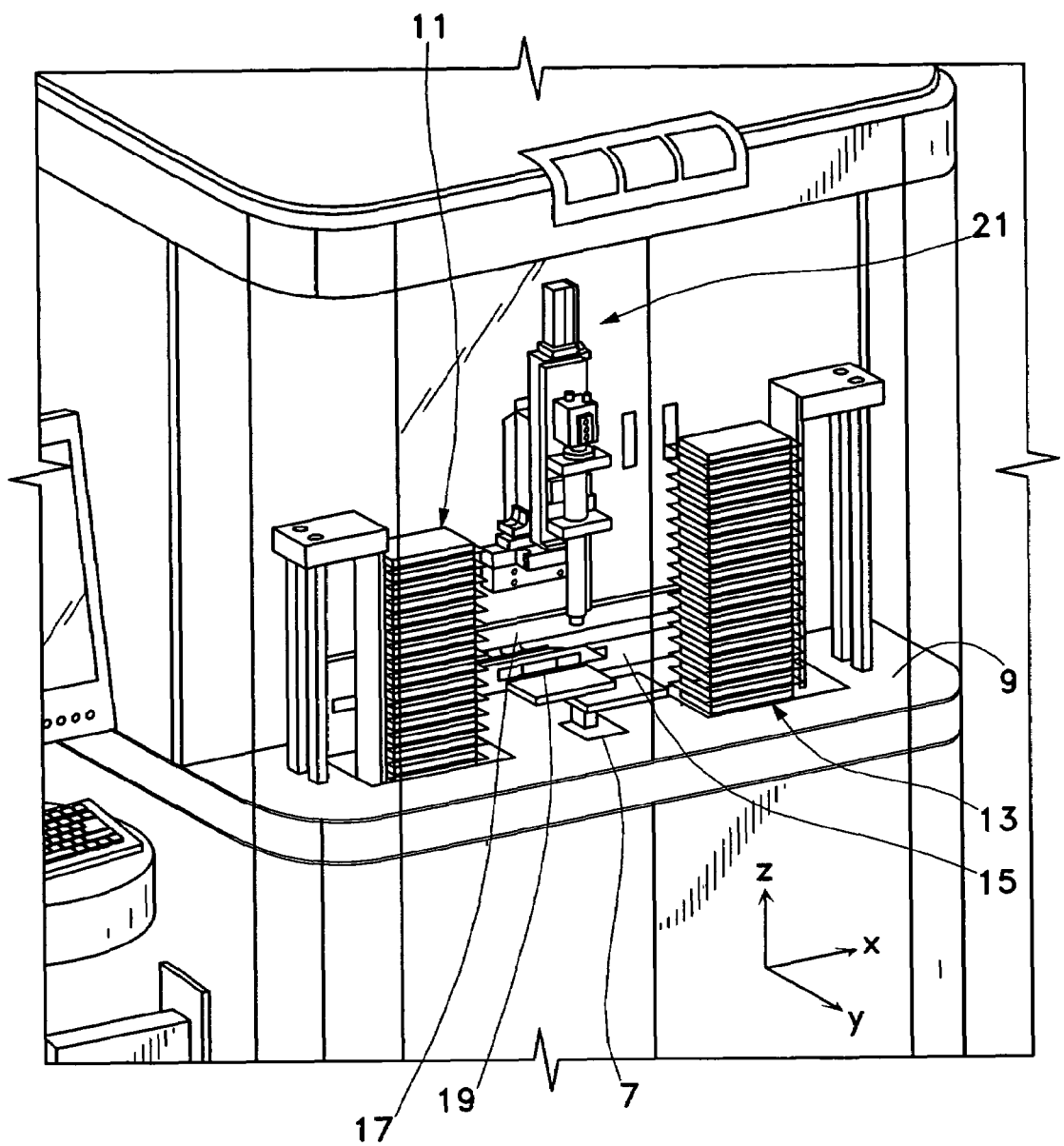
FIG. 1B illustrates an expanded view of the liquid transfer processing area of the high-throughput non-contact liquid transfer apparatus shown in FIG. 1A.

Referring to FIG. 1A, one particular design variation of a liquid transfer apparatus is shown. The primary liquid transfer mechanisms are housed within an enclosure 1. A user interface comprised of a keyboard 3 and a LCD monitor 5 is provided on the side of the enclosure. In this variation, other supporting electronics and mechanisms (e.g., computer system, power supply, etc.) are also housed within in the overall enclosure. The liquid transfer device is located within the main chamber. FIG. 1B is a close-up view showing some of the mechanisms in more detail. An acoustic emitter device 7 is positioned below floor of the main chamber (or processing deck) with the distal end protruding above the floor of the main chamber or processing area. A storage queue 11 comprise of an elevator assembly is provide on the left side of the acoustic emitter device for holding source liquid well plates. The source well plates are positioned within the elevator assembly with their well openings facing up, and contain source liquid to be transferred. A second storage queue 13, also comprise of an elevator assembly is provide on the right side of the acoustic emitter device for holding target well plates. The target well plates are positioned within the elevator assembly with their well openings facing down and may contain liquids or other compounds. Two X/Y linear stage assemblies 15, 17 positioned behind the main chamber have arms extending in to the main chamber. On the distal end of each arm is a handling device 19 secured to the arm. The two X/Y linear stages are stack one above the other. The X/Y linear stages allow their corresponding handling device to move on an X/Y plane. The handling device, comprise of a gripper assembly, has clamps that can open up and grip on to well plates in the storage queues. The lower X/Y linear stage 15 and its handling device is primary responsible for retrieving source liquid well plates and positioning them above the acoustic emitter device. The upper X/Y linear stage 17 and its handling device is responsible for retrieving target well plates and positioning them above the acoustic emitter device and the source liquid well plate. Because the elevator system 11, 13 provides vertical movement to the stack of well plates in the queue, the handling device may retrieve any of the well plates within the elevator queue. An image detection system 21 comprised of a vision system is positioned above the acoustic emitter system 7 and secured to a frame on the back of the main chamber. The image detection system 21 is aligned with the acoustic emitter device 7. A computer controller, along with its associated electronic and software, provides overall control of the complete unit. The main chamber is within an environmental and safety enclosure 1.

For illustration purpose, one variation of a liquid transfer sequence is described below. Under the control of a computer (not shown) the source elevator assembly position the desired source well plate at the level accessible by the lower gripper assembly. The lower X/Y linear stage positions its gripper assembly around the source well plate. The gripper assembly locks on to the source well plate and transfer the source well plate to the top of the acoustic emitter device. The image system detects the presence of the source well plate. The image system, along with multiple fiduciary markers on the well plate, allows the computer controller to calculate the position of the well plate and make any necessary alignment adjustment. Following a similar procedure, the upper X/Y linear stage retrieves a target well plate from the target elevator assembly and makes alignment adjustments. Once the position of the well plates are calibrated, the computer controller can align a specific well in the source well plate and a specific well on the target well plate on the vertical axis defined by the acoustic emitter. An acoustic wave is then propagated into the pool of liquid in the source well plate, forcing a drop of liquid to eject out of the pool and into the well on the target well plate that is aligned above it. If the target well plate is transparent or translucent the vision system may monitor the ejection process and verify that liquid has been successfully transferred. After the completion of the ejection, the computer controller can realign a different set of wells for the next ejection. Because the computer controller may access any of the wells in the source storage queue and any of the wells in the target storage queue, the selection of the second set of wells for fluid transfer may be completely independent of what was selected during the first ejection.

Acoustic Ejection

Figure 2A:
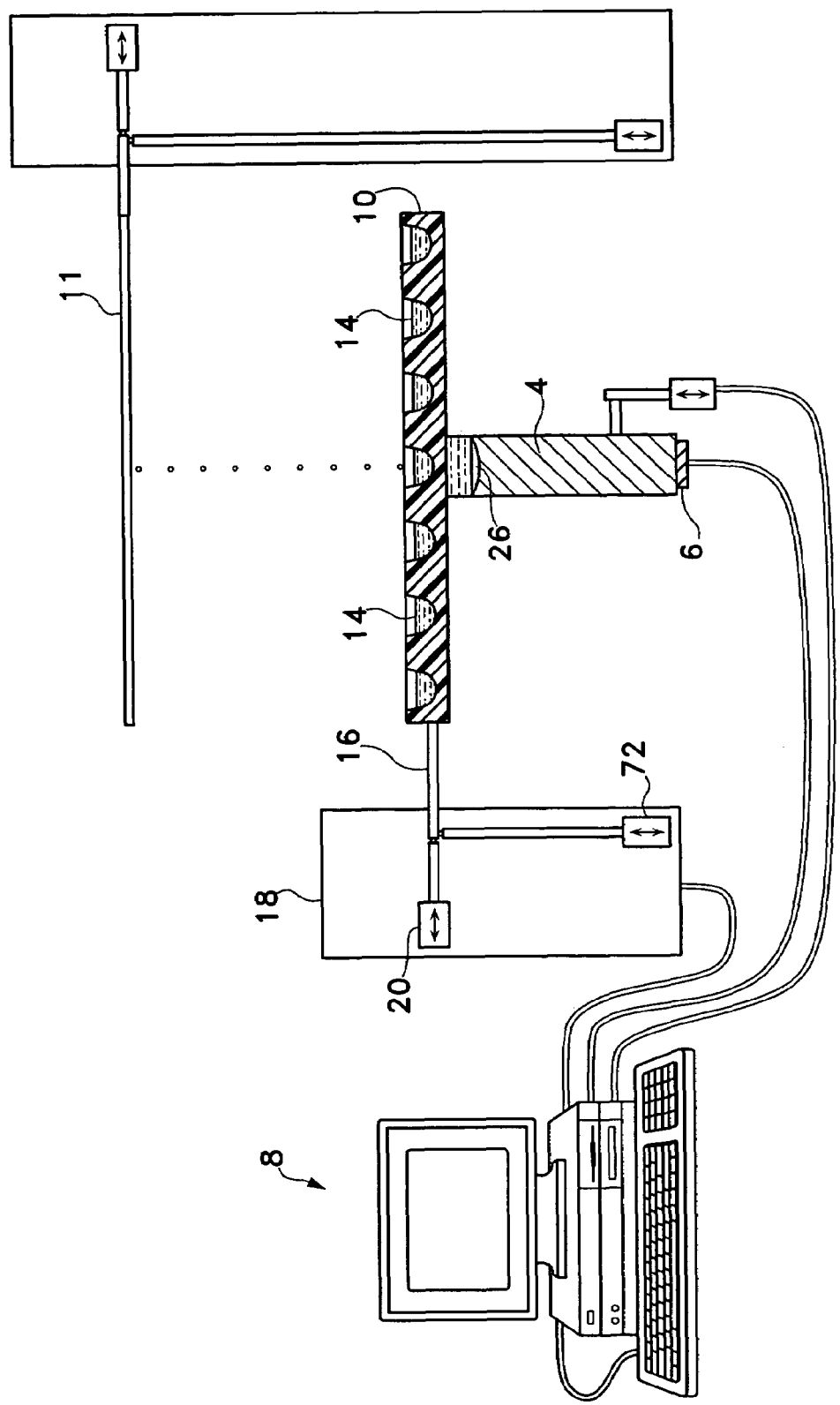
FIG. 2A illustrates one variation of a non-contact fluid transfer apparatus.

To aid in understanding the invention, the basic functionality of an acoustic ejection system is described below. An exemplary acoustic liquid ejection system 2, which incorporates a wave-guide 4, is shown in FIG. 2A. This particular variation of a non-contact liquid transfer apparatus has one acoustic wave emitter 6 in electrical communication with a computer 8. During operation the acoustic wave emitter 6 generates an acoustic wave that is propagated through a wave-guide 4. The acoustic wave may then be focused by a lens 26 prior to propagating through a coupling liquid 12. The acoustic wave is propagated through the coupling liquid after which the wave is transmitted through a source fluid containment structure 10 where the wave enters a pool of source fluid 14 thereby causing ejection of a droplet, mist or stream of source fluid from the surface of the pool. A target 11 may be positioned above the source fluid containment structure to capture the ejected liquid. The source fluid containment structure 10 may be held on a movable stage 16. The movable stage may reposition the source containment structure in the horizontal X/Y directions and/or the vertical Z. The moveable stage may be in communication with the computer 8, which allows the computer to select specific well on the fluid containment structure for ejection by aligning the selected well on top of the wave-guide. The target 11 may also be connected to a moveable stage, which may also be controlled by the computer to select specific location on the target for receiving the ejected liquid. This arrangement may allow the user to selectively eject liquids out of a plurality of wells on the fluid containment structure one after the other, and at the same time selectively prescribe specific location on the target to receive liquid from each ejection. The wave-guide may also be coupled to an actuator such that the user may adjust the focus location of the acoustic wave, to position it in the vertical direction within, above, or below the surface of the source fluid as desired. The computer may have implemented therein various algorithms to adjust the energy and/or the focal length of the acoustic wave emitter unit, as well as control and manage the focus location of the acoustic wave relative to a surface of a particular pool of source fluid present in or on a source fluid containment structure.

A similar system is described in U.S. application Ser. No. 09/735,709 filed Dec. 12, 2000 entitled "Acoustically Mediated Fluid Transfer Methods And Uses Thereof," hereby incorporated by reference in its entirety.

Various aspects of the exemplary system will now be described in more detail. Referring to FIG. 1, the system 2 includes at least one acoustic wave emitter 6 in electrical communication with a computer 8. The computer 8 may be a stand alone computing machine, a dedicated electronic control box with its own processor, or an electronic processing unit integrated with the fluid ejection system 2. For instance, the computer may be a control card integrated within the fluid ejection system. The computer 8 may provide feedback control of the acoustic wave emitter, the positioning of the wave-guide 4, and the moveable stage holding the source fluid container 10 to achieve synchronization and efficient fluid ejection. During operation, the acoustic wave emitter 6 generates an acoustic wave, beam, or pulse that may be propagated through a wave-guide 4. The acoustic wave may be focused by a lens 26 prior to propagating through coupling medium 12 (e.g. coupling liquid) to focus the energy of the acoustic wave into liquid 14 within a well of a microtiter plate. The acoustic wave is propagated through a coupling medium 12 after which the wave is transmitted through source fluid containment structure 10 where the wave may come into focus in a pool of source fluid 14 thereby causing a portion of the liquid to be ejected as a droplet, mist, or fountain of liquid. In one variation, 20 MHz acoustic waves are generated by the acoustic ejection system. In another variation, 40 MHz acoustic waves are implemented. Depending on the particular acoustic wave emitter implemented in the system, the acoustic wave emitter may be able to generate acoustic waves in a plurality of frequencies. The computer may also be used to control the specific frequency of acoustic wave being generated by the acoustic ejection system.

Examples of source liquid containment structures 10 include, but are not limited to, single and multi-well plates commonly used in molecular biology applications, capillaries (e.g., capillary arrays), a flat plate with isolated regions of fluids, and the like. However, other containers or structures may also be used to hold a liquid to be ejected. Notably, the source fluid containment structure 10 may be detachably affixed to a movable stage 16. The movable stage 16 may be controlled by actuator mechanism 18 which contains a horizontal actuator 20 or a vertical actuator 22 or a combination of the two actuators to control the movement of the stage 16 in both the vertical and horizontal directions. One or more horizontal actuator may also be implemented to allow the movable sate to move in both X and Y direction. The target 11 may also be attached to a movable stage and able to move in the X/Y direction and/or the Z direction. The actuator 18 may be in communication with a computer 8 which controls the movement of the stage to select a source fluid 14 or to adjust focusing of the acoustic wave or beam upon the source fluid 14.

The computer 8 may have implemented therein various algorithms to adjust the focal length and energy of the acoustic wave emitter as well as control and manage the location of the acoustic wave emitter relative to a particular source fluid present in or on a source fluid containment structure. The position of the focus, relative to the surface of the source fluid, may be adjusted by changing the position of the source fluid container and/or by adjusting the vertical height of the wave-guide/emitter unit. Accordingly, the system may be used to provide acoustic stimuli to optimally eject a droplet of the source liquid.

Figure 2B:
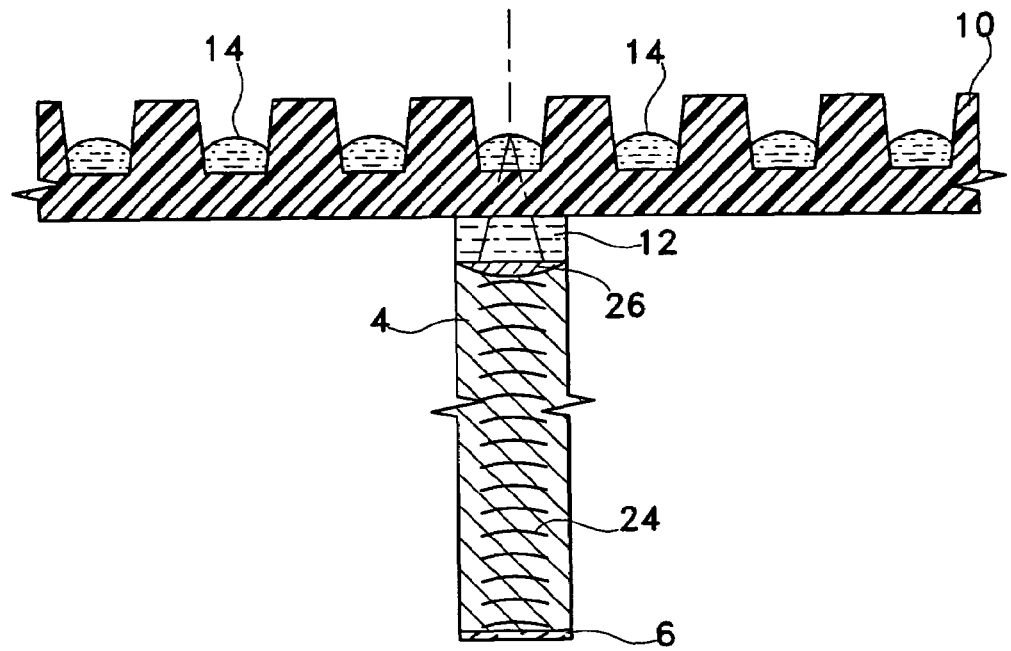
FIG. 2B is a schematic diagram illustrating another variation of the non-contact fluid transfer apparatus, where an acoustic wave generated by a piezoelectric element is propagated though a wave guide, a coupling medium, and a source fluid containment structure to a pool of source fluid, causing ejection of a droplet of source fluid from the surface of the pool.

The acoustic waves may be channeled from the acoustic wave emitter 6 (e.g., piezoelectric element) to the source fluid 14 via an acoustic wave channel or a wave-guide 4. Reference is made to FIG. 2B which shows an acoustic wave 24 being generated by a piezoelectric element 6 and propagated through acoustic wave channel (e.g., a wave-guide) 4. The rapid oscillation of the piezoelectric element 6 generates an acoustic wave 24, which propagates through the acoustic wave-guide 4 until it strikes the focusing lens 26. The wave then emerges into a coupling medium 12 (e.g., the coupling liquid) having a lower acoustic velocity. The spherical shape of the lens 26 imparts a focusing effect on the acoustic waves, thereby focusing the acoustic energy into the liquid 14. The acoustic wave-guide 4 may be constructed of aluminum, silicon, silicon nitride, silicon carbide, sapphire, fused quartz, certain glasses, or the like. In one variation, the acoustic wave-guide 4 is constructed of aluminum. Suitable materials for the fabrication of the acoustic wave-guide may have an acoustic velocity that is higher than the acoustic velocity of the source fluid. The piezoelectric element 6 may be deposited on, or otherwise intimately mechanically coupled to a surface of the acoustic wave-guide 4.

In one particular design, a liquid transition interface is provided to facilitate the propagation of an acoustic wave or beam from the wave-guide to a source fluid containment structure. The focusing lens may be implemented to direct the acoustic beam into an essentially diffraction limited focus within the source fluid pool. The focus may be placed at or near the fluid/air interface at the surface of the source fluid pool.

One or more heat exchangers, heaters and/or coolers may also be provided to adjust or maintain the coupling liquid at a desirable temperature. Controlling the temperature of the coupling medium may minimize any effect of temperature on the source fluid.

The coupling medium may have an acoustic impedance that is close to the acoustic impedance of the source fluid containment structure. The coupling medium may be in contact with the wave-guide 4 and the bottom surface of the fluid containment structure 10, thereby providing for efficient energy transfer from the acoustic wave-guide 4 to the fluid containment structure 10, and subsequently through the source fluid 14. In another variation, the acoustic wave emitter is directly coupled to the source fluid containment structure 10 through the coupling medium 12. As an example, a polystyrene multi-well plate has an acoustic impedance of about 2.3. Water has an acoustic impedance of about 1.7. Accordingly, water may be a good coupling medium when the source fluid containment structure is a polystyrene device (e.g., a multi-well plate) due the close match in impedance values between water and the plate. By adding other fluids (e.g., glycerol, or the like) to the water, an even closer match may be achieved. Other fluids may also be employed in the practice of the present invention.

Thus, by providing a coupling medium 12 between the acoustic wave emitter 6, or preferably the acoustic wave-guide 4, and the fluid containment structure 10, an efficient transfer of energy may be achieved.

The acoustic wave emitter 6 may be any of various acoustic wave generators that are well known to one skilled in the art. In one variation, a piezoelectric transducer is employed as an acoustic wave emitter 6. The piezoelectric transducer may comprise a flat thin piezoelectric element, which is constructed between a pair of thin film electrode plates. As is understood by those of skilled in the art, when a high frequency and appropriate magnitude voltage is applied across the thin film electrode plates of a piezoelectric transducer, radio frequency energy will cause the piezoelectric element to be excited into a thickness mode oscillation. The resultant oscillation of the piezoelectric element may generate a slightly diverging acoustic beam of acoustic waves. By directing the wave or beam onto an appropriate lens 26 having a defined radius of curvature (e.g., a spherical lens, or the like), the acoustic beam can be brought to focus at a desired point. Acoustic energy may be modulated to deliver energy for a short period of time or in short pulses to form an energy wave.

The piezoelectric transducer may have various forms including a flat crystal disk, or other crystal designs, e.g., square, perforated disk, and the like. In one variation, the piezoelectric transducer may be a flat disk. Because many electronic circuits are designed for a 50Ω (ohm) load, it may be desirable to employ a 50Ω transducer. Various piezoelectric materials, which are well known to one skilled in the art, may be suitable for fabricating the piezoelectric transducer. Examples of materials which may be suitable for making the piezoelectric transducer include Lithium Niobate, Lead Niobate and Quartz. Various shapes of piezoelectric crystals are also contemplated for use in the implementation of the present invention.

A computer may send an analog voltage pulse to the piezoelectric transducer by an electrical wire. The voltage pulse may be controlled, for example, by a MD-E-201 Drive Electronics manufactured by Microdrop, GmbH, Muhlenweg 143, D-22844 Norderstedt, Germany. The electronics may control the magnitude and duration of the analog voltage pulses, and also the frequency at which the pulses are sent to the piezoelectric transducer. Each voltage pulse may cause the generation of an acoustic wave from the piezoelectric transducer, which in turn is propagated through a coupling medium and into or through the source fluid thereby impinging on the surface of the source fluid. Such acoustic waves may be generated to eject a droplet, mist or stream, from the source fluid into an excited oscillating state.

[a] Acoustic Emitter Device

Figures 3A, 3B:
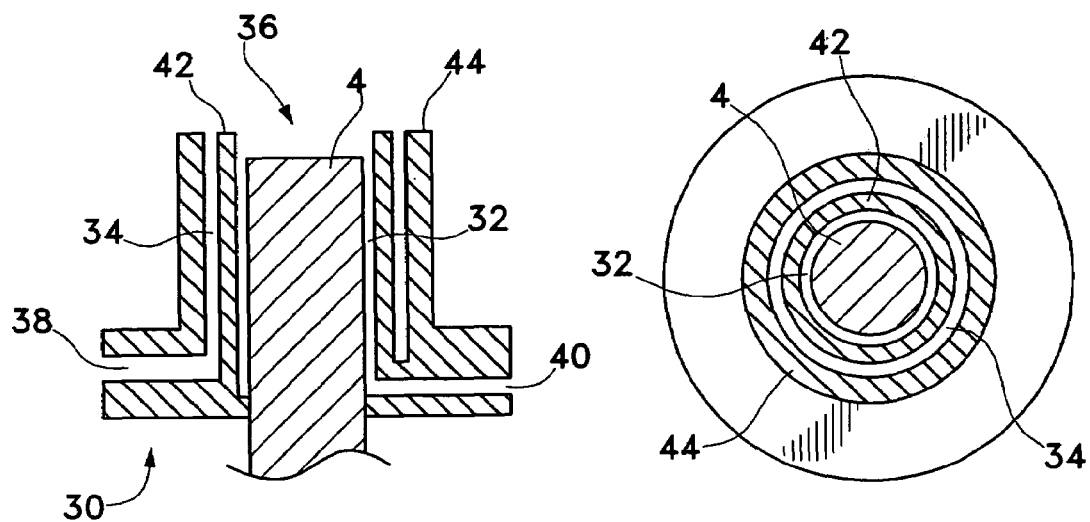
FIG. 3A illustrates a cross sectional view of one variation of a wave-guide assembly where the wave-guide is moveably deposed in the inner lumen of a fluid basin.
FIG. 3B is the top view of the wave-guide assembly shown in FIG. 3A.

Referring to FIG. 3A, one variation of a wave-guide assembly for isolating a liquid coupling medium at the tip of wave-guide 4 is shown. In this variation the fluid basin surrounding the wave-guide 4 comprises a structure with two coaxial lumens, formed by an inner wall 42, and an outer wall 44, as shown in FIG. 3B. The inner lumen 32 forms a container for supplying coupling liquid to the distal end of the wave-guide. A wave-guide 4 may be positioned within the inner lumen 32 such that the wave-guide may be moved relative to the inner wall 42. The outer lumen 34 formed between the inner wall and the outer wall may be a channel for applying a negative pressure near the wave-guide 4 at the distal end 36 of the assembly. The inner lumen 32 is the channel for providing coupling liquid to the distal end 36 of the wave-guide 4.

A port 38 may be provided for accessing the outer lumen, as seen in FIG. 3A. A negative pressure generator may be connected to this port 38 to generate a negative pressure area at the distal end of the outer lumen 34. The negative pressure generator may be connected directly to the port, or alternatively, the negative pressure generator may be connected to the port through tubing or other connectors or channels, which are able to provide a path from the port to the vacuum generator. The negative pressure generator may provide constant suction at the distal end of the wave-guide assembly. Alternatively, the negative pressure generator may provide suction intermittently or on an as needed basis.

A second port 40 may be provided for accessing the inner lumen 32. A fluid source may be connected to the second port 40 to provide the coupling liquid to the inner lumen 32.

The fluid source may be connected to the second port 40 through tubing or other connectors or channels, which are able to provide a path from the port to the vacuum generator. Additional ports may be provided for accessing the inner and/or the outer lumen.

In one variation, a fluid pump is connected to the second port 40. The pump may also be connected to a fluid source or reservoir. The pump may provide continuous flow of fluid into the inner lumen 32 of the assembly. Alternatively, the pump may provide fluid intermittently or on an as needed basis.

Figure 10:
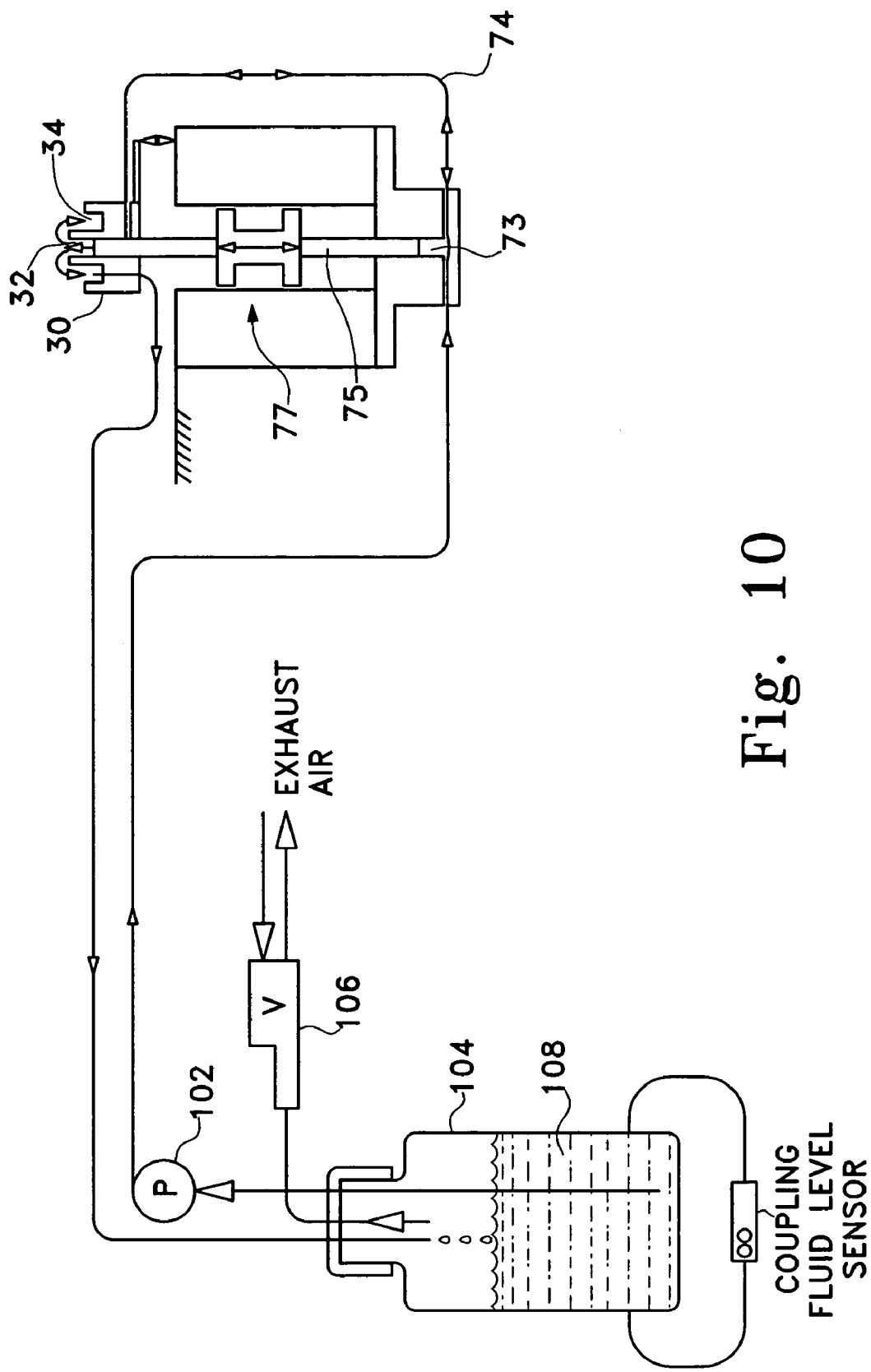
FIG. 10 illustrates one variation of an overall system layout for supplying coupling liquid to the fluid basin.

In another variation, shown in FIG. 10, the inner lumen 32 is connected to a peristaltic pump 102, which is further connected to a fluid supply bottle 104. The peristaltic pump draws coupling liquid 108 from the fluid supply bottle 104 and pumps the coupling liquid into the inner lumen 32. A vacuum generator 106 is connected to the fluid supply bottle 104 for generating a negative pressure inside the bottle. The outer lumen 34 is connected to the fluid supply bottle 104, and due to the negative pressure inside the fluid supply bottle 104, coupling liquid is drawn from the outer lumen into the bottle 104. This particular configuration allows the coupling liquid to flow from the fluid supply bottle 104 into the inner lumen, and exit at the outlet surrounding the wave-guide. Excess coupling liquid at the distal end of the wave-guide is drawn into the outer lumen and flows back into the fluid supply bottle 104.

In one variation of the invention, the pump supplies a constant flow of coupling liquid to the end of the wave-guide through the inner lumen and suction in the outer lumen constantly draws liquid away. The rate at which the coupling liquid is supplied to the end of the wave-guide and the rate of removal of coupling liquid by the suction may be about the same, so that coupling liquid is supplied to maintain a "bubble" of liquid of constant volume at the end of the wave-guide.

In yet another variation, a computer may modulate the amount of coupling liquid supplied to the inner lumen 32 and/or the amount of suction applied to remove excess fluid, in order to control the amounts of fluids at the distal end of the wave-guide.

Figure 4A:
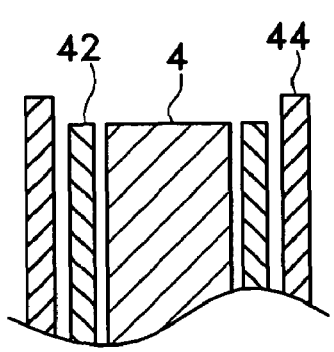
FIG. 4A illustrates one variation of the fluid basin that surrounds the wave-guide, where the outer wall is higher than the inner wall, which separates the suction channel and the coupling liquid supply channel.
Figure 4B:
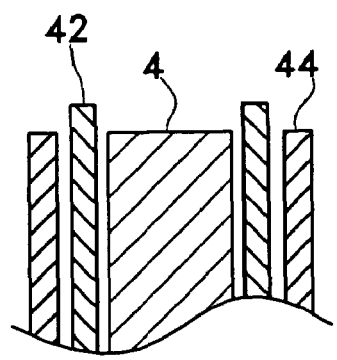
FIG. 4B illustrate another variation of the fluid basin where the outer wall is lower than the inner wall, which separates the suction channel and the coupling liquid supply channel.

In one variation of the fluid basin 30 which surrounds the wave-guide 4, the inner wall 42, which defines the inner lumen and the outer lumen, is at the same level as the outer wall 44 of the assembly, as shown in FIG. 3A. In an alternative design, the inner wall 42 is lower than the outer wall 44, as shown in FIG. 4A. In another variation, the inner wall 42 is higher than the outer wall 44, as shown in FIG. 4B.

Figure 5:
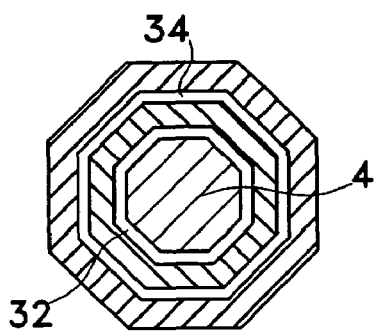
FIG. 5 shows another variation of the wave-guide assembly where the wave-guide unit and the surrounding channels are octagonally shaped.

The channel providing the coupling liquid and the channel supplying the suction may surround the wave-guide cylindrically. Alternatively, the channels and supporting walls may form triangular shapes, rectangular shapes, pentagonal shapes, or other shapes that one skilled in the art would consider suitable for the mechanical function of the structure. The wave-guide 4 itself may also be adapted to other cross-sectional shapes that are functionally feasible. The shape of the wave-guide 4 may match the shape of the surrounding structure. However, this is not a necessary requirement. FIG. 5 illustrates one variation of the wave-guide assembly where an octagonal shape has been adapted.

Figure 6A:
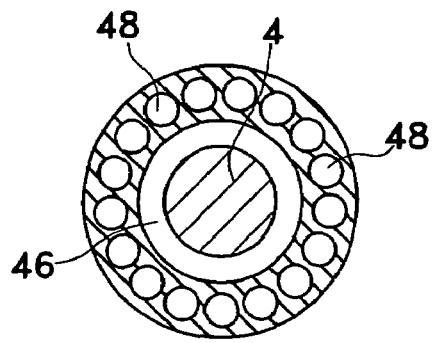
FIG. 6A shows another variation of the wave-guide assembly where a coupling liquid supply channel surrounds the wave-guide, and the vacuum suction channel comprises a plurality of channels surrounding the coupling liquid supply channel.
Figure 6B:
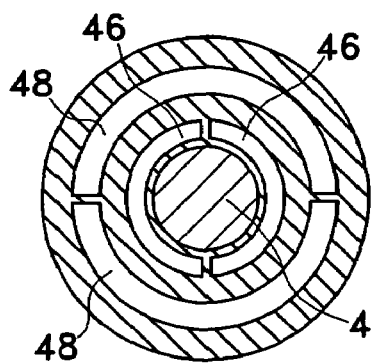
FIG. 6B shows yet another variation of the wave-guide assembly where both the coupling liquid supply channel and the vacuum suction channel are each comprised of two separate channels.

The coupling liquid supply path 46 and the suction path 48 may each be comprised of individual channels. However, other combinations are also possible. Both the coupling liquid path 46 and the suction path 48 may be comprised of a plurality of channels or paths. The channels may have a cylindrical shape, but this is not required. For example, the channels may have a triangular cross section. In FIG. 6A, one variation of the fluid/air channels is illustrated, where the fluid channel 46 is comprised of a single cylindrical channel surrounding the wave-guide 4, and the suction channel 48 is comprised of a plurality of channels surrounding the fluid channel 46. The suction channels 48 may be connected to a single negative pressure source or a plurality of negative pressure sources. In another variation, both the coupling liquid supply channels 46 and the suction channels 48 are comprised of dual channels positioned around the wave-guide 4, as seen in FIG. 6B.

Figure 7:
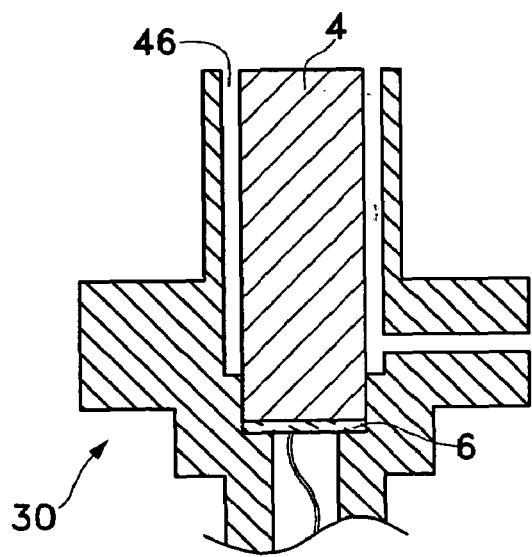
FIG. 7 shows another variation of the wave-guide assembly where the wave-guide and the fluid basin are connected to each other.

In another variation, the wave-guide 4 may be connected to the fluid basin 30 surrounding the wave-guide, forming an integrated unit, as seen in FIG. 7. An optional suction channel (not shown) may surround the fluid channel 46 for removing excess coupling liquid. The integrated wave-guide/fluid basin unit may be coupled to a displacement device (e.g., an actuator), and may move in the vertical direction as a complete unit.

In another aspect of the invention, the wave-guide and its fluid basin may be integrated with a high-speed linear servo axis mechanism. In one variation, the device is designed to move the focus of the wave-guide to a desired position within a 12 mm vertical range within 50 milliseconds, and appropriate compensation mechanisms as described herein are provided to maintain the fluid coupling between the wave-guide 4 and the source fluid containment structure 10. The wave-guide 4 may comprise an acoustic wave-conducting medium with a lens adapted at the distal end for focusing the acoustic wave. The fluid ejection system may have additional constraints such that the linear axis of the wave-guide unit is to maintain a 0.02 mm centerline across the full stroke of the 12 mm displacement.

Figure 8A:
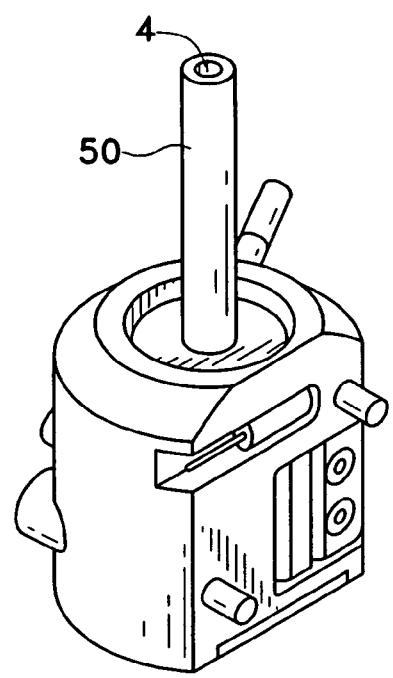
FIG. 8A shows one variation of an acoustic wave emitter module where a wave-guide is integrated within a sealed housing along with, a transformer, a inductor, and other electrical and mechanical parts.
Figure 8B:
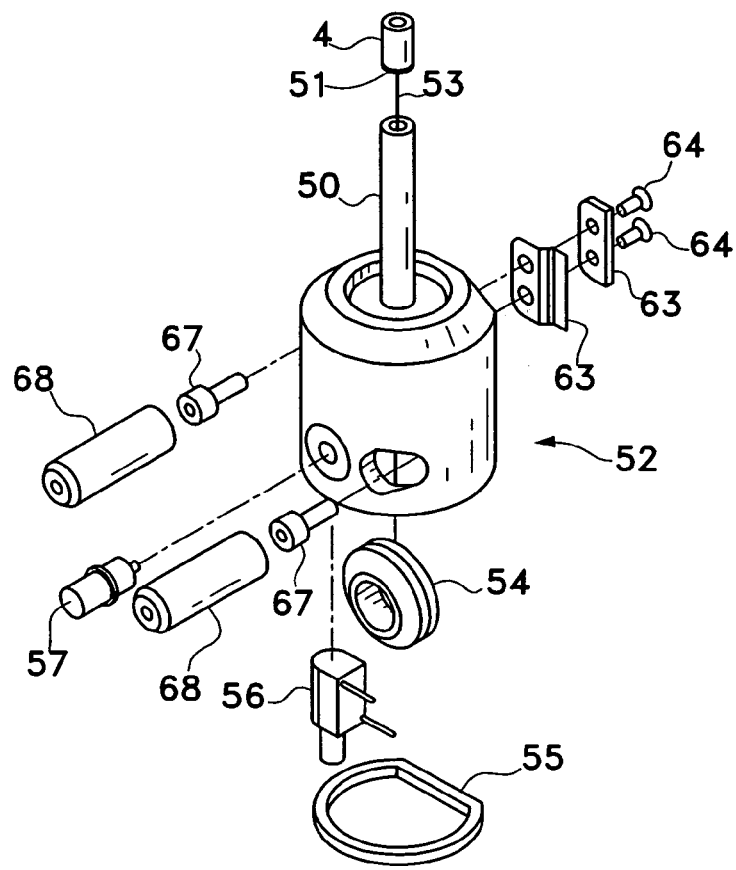
FIG. 8B shows the same acoustic wave emitter module of FIG. 8A in a disassembled condition for illustration purpose.
Figure 9C:
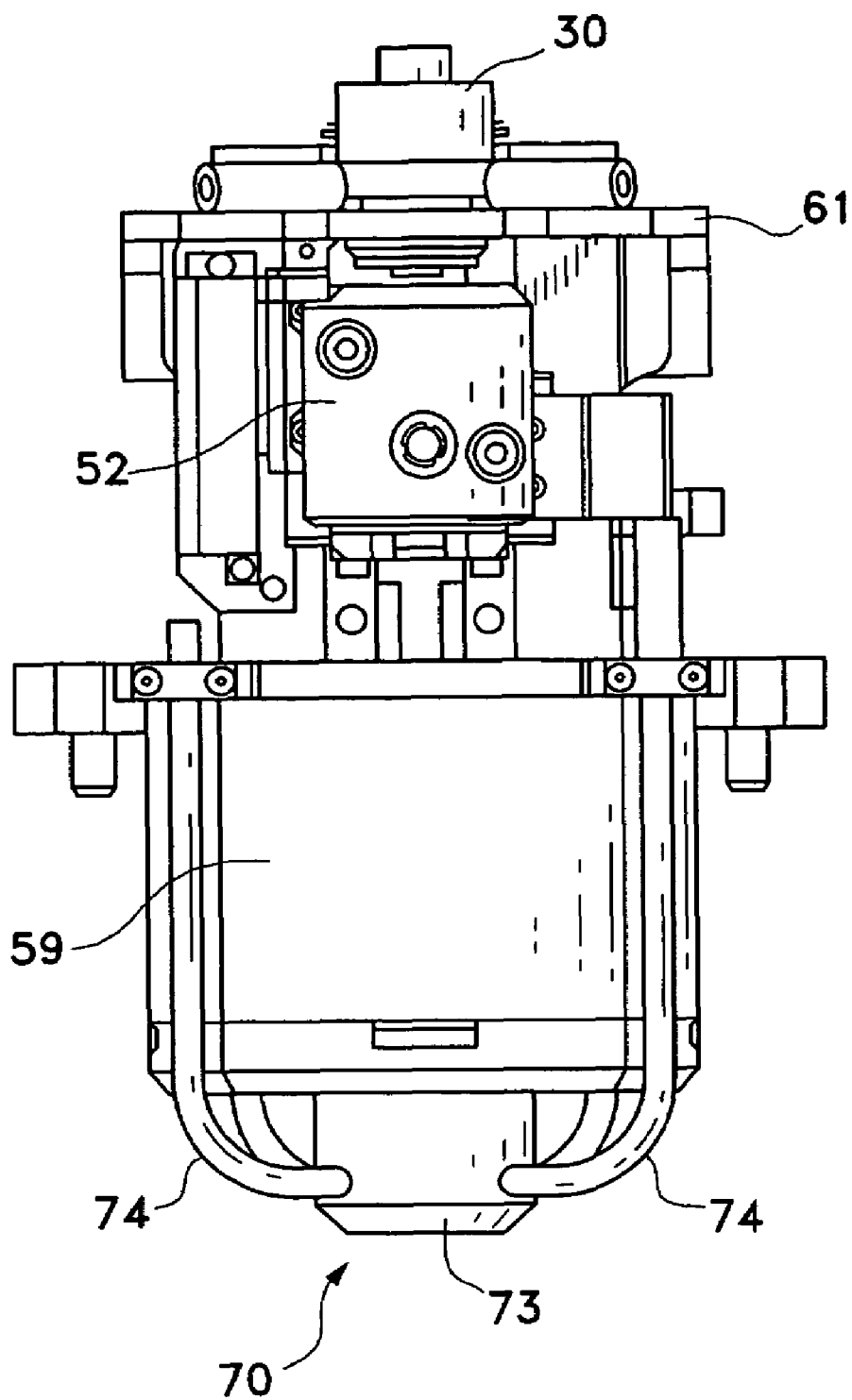
FIG. 9C illustrates the frontal view of the linear servomechanism shown in FIG. 9A.

In one variation, the wave-guide 4 may be integrated within a housing 50 as shown in FIG. 8A. The housing 50 may be part of a sealed unit, which forms the acoustic wave emitter module 52. FIG. 8B shows the acoustic wave emitter module in a disassembled condition. The acoustic wave emitter module 52 comprises a wave-guide 4, a piezo-electric transducer 51, connection wiring 53, location brackets 63 and screws 64, a transformer 54, an inductor 56, a sub-miniature electric connector 57, mounting screws 67 and covers 68, a data storage chip, and a base cover 55. The transformer and the inductor may be utilized to provide impedance matching between the acoustic wave emitter module and the input power supply or the electric signal source supplying the current to the piezo-electric transducer. The acoustic wave emitter module 52 may be adapted to move on a vertical path as a unit. The movement of the acoustic emitter module 52 may be driven by a linear servomechanism comprising a stage 58 coupled to a voice coil motor located within a housing 59, as illustrated in FIG. 9A. The mechanical parts within FIG. 9A is shown without tubing connecting the various ports 39 on fluid basin 30 and the flow lines 74 to illustrate the main components of the system in a clear manner. The wave-guide housing 50 extends into a fluid basin 30, and moves in the vertical direction within the basin 30. The fluid basin 30 is positioned by a frame 61. The frame is couple to a support panel 62. The voice coil motor may comprise fixed coils and moving magnets located inside of the housing 59. Furthermore, a 0.5 micron resolution linear encoder, a positive limit sensor, and a home sensor may also be built into a linear glass scale 66, which is connected to the stage 58, to complete the closed loop system for controlling the position of the wave-guide 4, as seen in FIG. 9B. The home sensor refers to a sensor use to detect a reference location for the moveable device.

In another aspect of the invention, a fluid compensation system may be provided to prevent pressure build up in the fluid basin 30 and maintain adequate fluid coupling between the wave-guide 4 and the source fluid containment structure. In one variation, illustrated in FIG. 9C, the fluid compensation system comprises a built-in piston pump 70, and flow lines 74 to the fluid basin 30. The piston pump is comprised of a piston 75 acting upon liquid in a chamber 73 formed as part of the housing 59. The voice coil motor may actuate a piston 75, which extends into a piston chamber 73 to displaces fluids from the piston chamber 73 as the piston is forced downward by the voice coil motor 77, as illustrated in FIG. 10. The displaced fluid is force into the flow lines 74, which are connected to the piston chamber 73. The flow lines direct the flow of fluid to the fluid basin 30. Thus, as the wave-guide is lowered, coupling liquid displaced by the piston may compensate for the extra volume on top of the wave-guide due to the displacement. As the wave-guide is raised, the piston also rises to draw coupling liquid out of the basin via the flow line 74. The flow lines 74 may be sized to transfer a set volume of fluid with minimal pressure. The design minimizes pressure build up in the fluid basin 30 and minimizes ejection of fluid from the basin during the quick linear movement of the wave-guide 4.

Figure 11A:
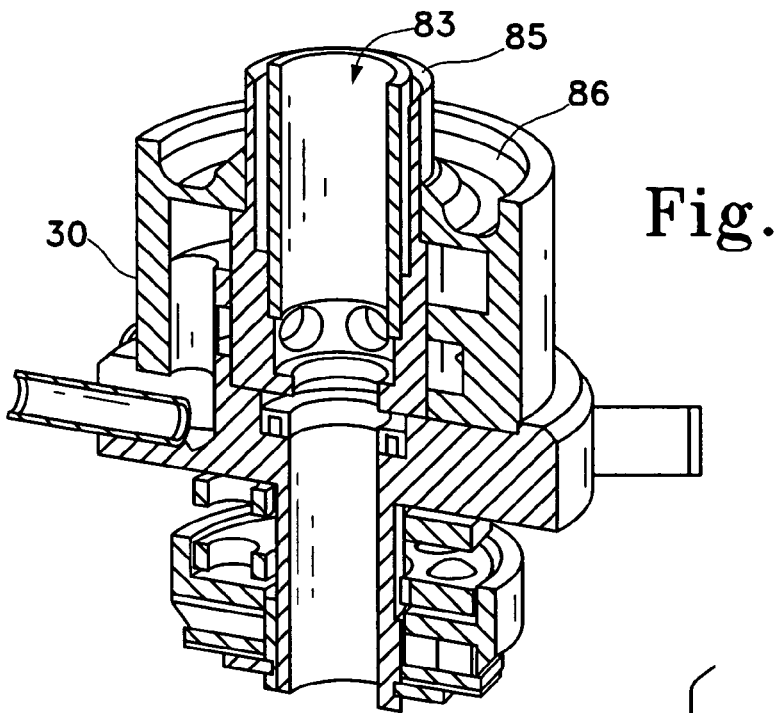
FIG. 11A shows one particular design of a fluid basin, where the wave-guide positioned at the distal end of an acoustic wave emitter module, shown in FIG. 8A, may extend into the inner lumen of the fluid basin, which is designed to provide a negative pressure in the immediate area surrounding the inner lumen that forms the coupling liquid inlet.

The distal end of the wave-guide unit described above may extend into a fluid basin 30, which is shown in detail in FIG. 11A. In this variation, the fluid basin 30 has a fluid port for supplying fluids to the inner lumen 83 surrounding the wave-guide. An air port is provided for connection to a vacuum source for generating negative pressure in the outer lumen 85. A trough 86 is provided for capturing excess liquids that spill over or splatter outside the suction area. A drain or channel may be provided to remove fluids captured by the trough. The drain may be connected to a negative pressure source to assist the removal of fluids.

Figure 11B:
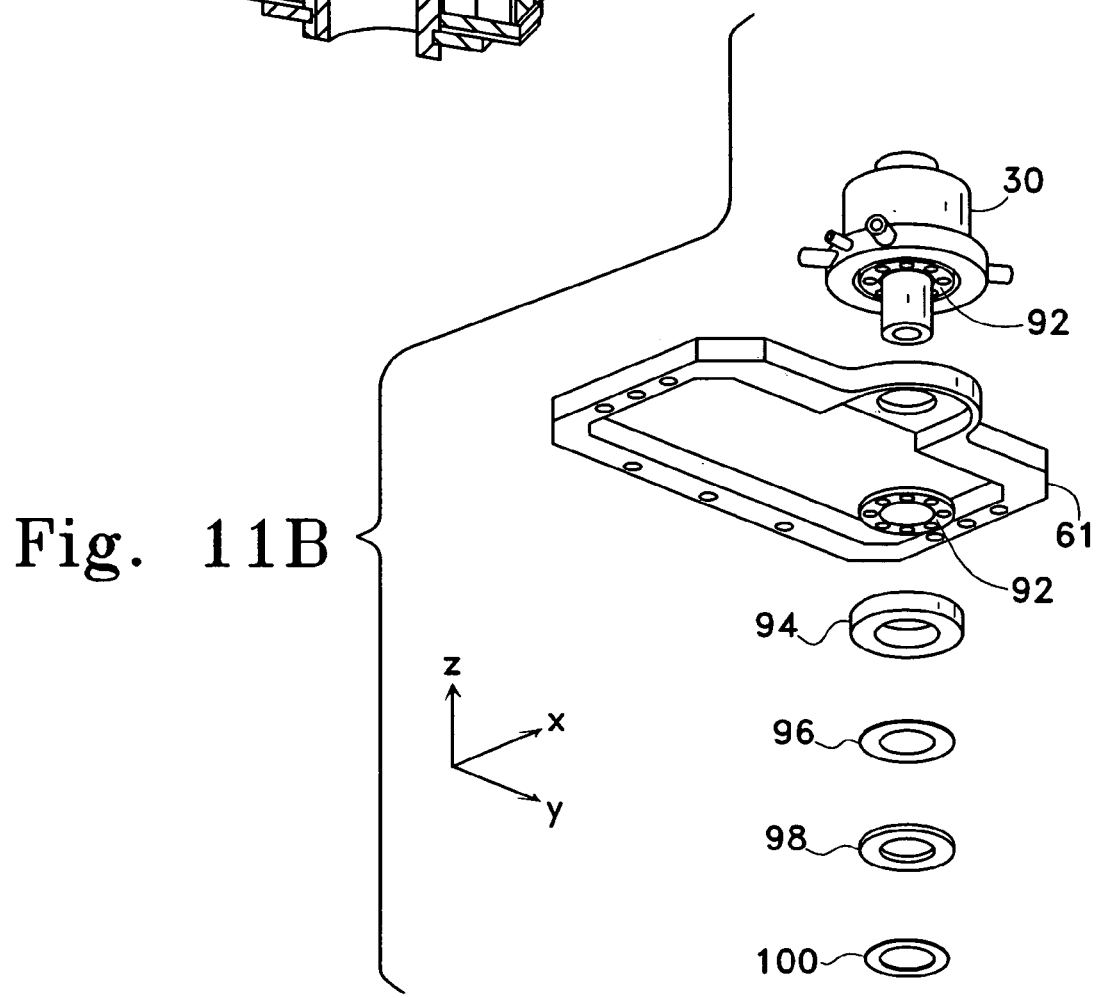
FIG. 11B illustrates one variation of a thrust bearing assembly for positioning the fluid basin of the wave-guide assembly. The bearings, spring and washer, are shown in the dissembled condition for illustration purpose.
Figure 12B:
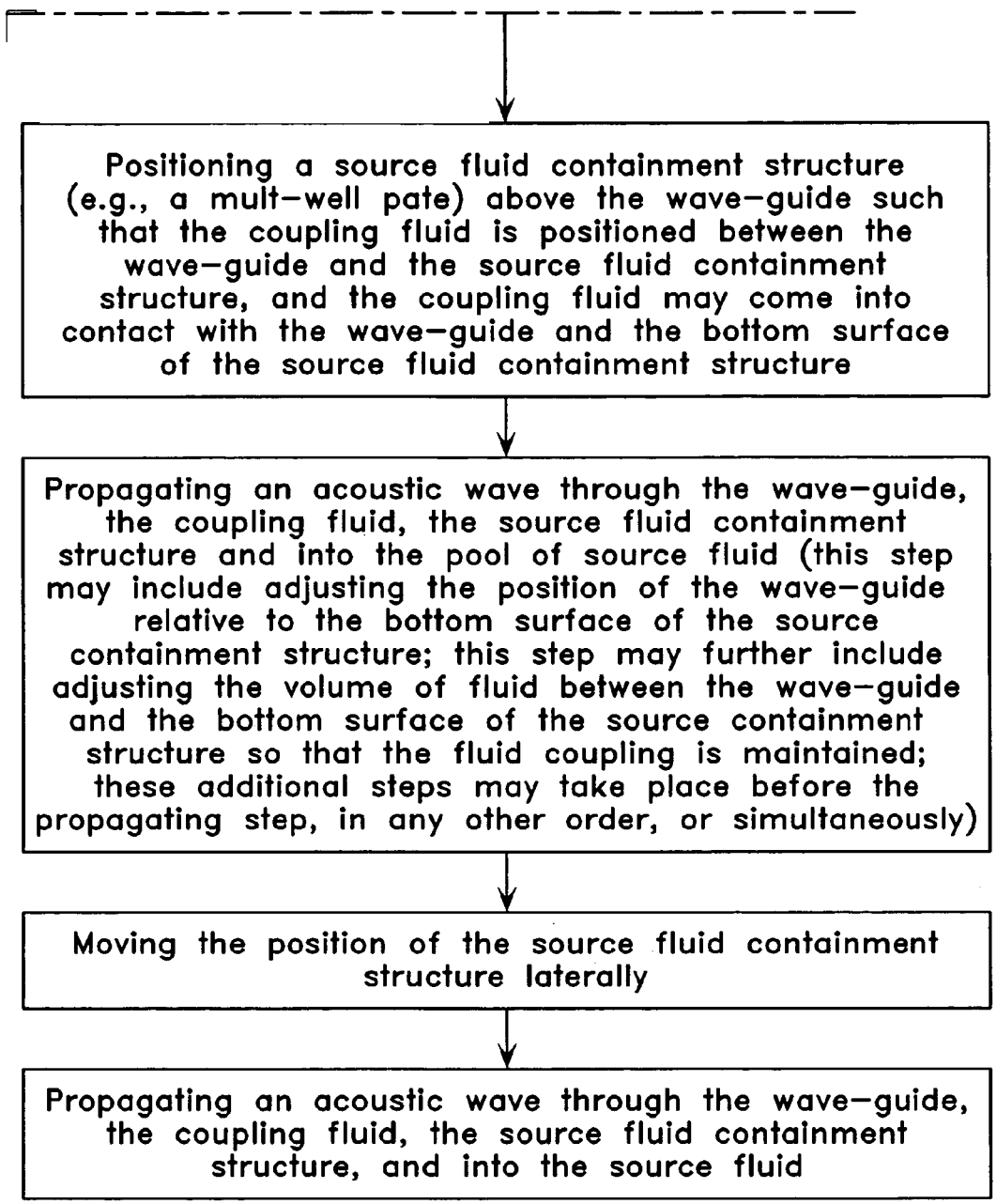
FIG. 12 shows a schematic diagram of variations of the method for utilizing a negative pressure to isolate a coupling liquid at the distal end of a wave-guide.

In yet another aspect of the invention, locking mechanisms are provided to secure the fluid basin 30 in such a way as not to bias the centerline of the wave-guide 4. A frame 61 may be provided to secure the fluid basin 30 and prevent movement of the fluid basin 30 in the vertical axis (Z-axis) direction. The frame 61 may be positioned with an independent stage or it may be attached to another structure or stage in the fluid ejection system. In one variation, shown in FIG. 11B, a thrust bearing assembly comprises of thrust bearings 92, a bearing cup 94, a preloaded spring 96, a washer 98, and a snap ring 100, is provide to secure the fluid basin 30 on the frame 61 such that the fluid basin 30 may have some degree of freedom in the X-Y plane (e.g., 1 mm X and 1 mm in the Y axis movement) but at the same time prevent any Z-axis movement of the basin. The freedom of movement in the X-Y plane minimizes side loads that could be imparted to the wave-guide by the fluid basin due to misalignment between the fluid basin and the wave-guide, and this may prevent bias of the wave-guide centerline.

As shown in FIG. 9A, the frame 61 supporting the fluid basin 30 may be couple to the support panel 62 of the system. In one variation, the frame 61 is attached to a carriage system, which is connected to the support panel 62. Linear motor may be incorporated to move the frame 61 in the vertical directions and consequently moving the fluid basin 30, which surrounds the wave-guide. The linear motor may be controlled by the system computer, thus allowing the vertical position of the fluid basin 30 be adjusted as needed. For example, the vertical height of the fluid basin may be adjusted to control the amount of coupling liquid at the distal end of the wave-guide.

In addition, the wave-guide and the fluid basin may be raised or lower concurrently so that appropriate space is maintained between the tip of the wave-guide and the bottom of the source fluid container that is positioned above the wave-guide. The fluid basin may be lowered during operation of the system to provide sufficient clearance above the acoustic wave emitter module for placement of source fluid container.

In this variation, the vertical position of the wave-guide and the fluid basin may be adjusted independently. For example, well plates with a skirt or edges that extends downward may be used along with the liquid ejection apparatus described herein. In order for the well plate handler to position the well plate above the acoustic emitter without being block by the distal ends of the wave-guide or the distal end of the fluid basin, it may be necessary to lower the wave-guide and the fluid basin in the vertical direction to provide sufficient clearance for the skirt or the extended edges of the well plate. Once the source well plate is in-place, the fluid basin and the wave-guide may then be raised.

Other coupling mechanisms and linear displacement devices or motors may also be implemented to provide vertical displacement of the frame and the fluid basin that is coupled to the frame. In an alternative design, linear displacement mechanisms are connected directly to the fluid basin to allow the fluid basin to move on the Z-axis of the system.

In another aspect of the invention, detection of the fluid level (volume and/or height) of source fluid in the source fluid containment structure may be performed by observing the acoustic reflection properties of the pool of source fluid. For example, by detecting the reflection of the acoustic beam employed to eject the droplet from the surface, the volume can be computed based on empirically determined acoustic reflection characteristics. Since the acoustic wave emitter (e.g., a piezoelectric transducer) design may be similar to acoustic measuring devices the droplet generator's transducer may also be used for acoustic depth sensing as a means of pool level or volume feedback measurement. The signal may be processed and the system may then be adjusted to further move the focus of the acoustic wave or beam as the level or volume changes. Alternatively, the system may send a weaker acoustic wave, which does not cause fluid ejection, for the sole purpose of measuring fluid level. In another variation, a secondary piezoelectric transducer can be employed to generate and/or detect the acoustic wave employed to detect the fluid level. The secondary piezoelectric transducer may be toroidal and disposed around the perimeter of the piezoelectric transducer used to eject the droplet of fluid (i.e., the primary transducer).

This invention further includes various methods of utilizing negative pressure areas to isolate coupling liquid on a wave-guide. In one variation, a wave-guide is provided for directing an acoustic wave. The wave-guide may be surrounded by a fluid channel for supplying a coupling liquid. The fluid channel may further be surrounded by an outer channel for applying negative pressure. Coupling liquid may be directed to the distal end of the wave-guide followed by the generation of a negative pressure around the distal end of the wave-guide. The negative pressure area may remove any excess coupling liquid around the distal end of the wave-guide. A well plate may then be positioned above the distal end of the wave-guide. The coupling liquid at the distal end of the wave-guide may come into contact with both the wave-guide and the bottom surface of the well plate. The well plate may be aligned with the wave-guide such that the well containing the desired source fluid is directly above the wave-guide. The position of the wave-guide may then be adjusted so that the focus of the wave-guide output is at a position that provides good ejection of droplets, mist or streams. An acoustic wave with sufficient intensity and strength is then generated and propagates through the wave-guide, the coupling liquid, and the source fluid containment structure, into the source fluid and forcing a drop of fluid to eject from the surface of the source fluid pool. Other variations of the method are illustrated in the schematic block diagram of FIG. 12.

In another variation of the method, a liquid is supplied to a distal end of a wave-guide and a constant negative pressure is provided in the area surrounding the distal end of said wave-guide. Excess liquid is captured and removed by said negative pressure. This variation may further include providing a fluid containment structure having a bottom surface and position the fluid containment structure on top of the wave-guide so that the liquid at the distal end of the wave-guide comes into contact with the bottom surface of said fluid containment structure.

In another variation, coupling liquid is constantly supplied to the end of the wave-guide. As the wave-guide is move vertically, the volume of coupling fluid on top of the wave-guide is adjusted to compensate for change in overall volume between the wave-guide and the source fluid containment structure.

In yet another variation, a constant negative pressure is maintained in the area surrounding the distal end of the wave-guide, and coupling liquid is then supplied to the distal end of the wave-guide. A fluid containment structure is then placed over the waive-guide so that the coupling liquid comes into contact with a bottom surface of the fluid containment structure. The fluid containment structure may have multiple wells and may contain source fluids in one or more of the wells. An acoustic wave is then propagated through the wave-guide, the coupling liquid, the source fluid containment structure, and into the source fluid in the well. The acoustic energy then ejects a portion of the source fluid from the well. The vertical position of the wave-guide may be adjusted prior to each fluid ejection. The volume of the coupling liquid above the wave-guide may also be adjusted so that the coupling between the fluid containment structure and the wave-guide is not compromised. After each ejection, the position of the source fluid containment structure and/or the target may be adjusted by sliding or moving them laterally in the X/Y plane. After realignment of a source fluid well and a target location with the wave-guide, additional droplet, mist, or stream of fluid may be ejected from the source fluid well on to the target.

In addition, a procedure for determining the focus as well as preferred locations for positioning the wave-guide relative to the surface of the source liquid pool within a source vessel to achieve ejection in a controlled and consistent manner will be described below. The wave-guide may be adjusted in a vertical direction to position the focus of the output acoustic wave on a vertical axis as described above. In one variation, the optimum location to place the focal point may be empirically determined by moving the position of the wave-guide vertically in an incremental displacement relative to the surface of a pool of source fluid placed above the wave-guide. This increment, for example, may be as small as 1 micron or as large as 1 cm. A constant amount of energy is introduced into the wave-guide at each incremental displacement. The condition/size/volume/quality of the droplet morphology of the ejected liquid, if any, may be recorded by the user or a computer. Through this iterative process, a profile of the amount fluid ejection relative to the position of the wave-guide may be plotted. Such profile may also reveal the actual focus (or focal distance) of the wave-guide. One would expect the source liquid ejection at the two extreme ends of the spectrum to be poor, and a region or regions in between to have quality amounts of fluid ejection. This region or regions may then be used to define a preferred range(s) of functional locations for the wave-guide.

The user may repeat the above process at the same power input level to acquire more data points for the ejection profile at this power level. Once the user determine the ejection profile at a particular input power level, the input power may be stepped up or down, and the ejection profile at a different level may be determined. During this ejection profile mapping process, the user may supply fluid to the source fluid pool to keep the source fluid at the same level. Alternatively, the user may prepare multiple source wells, with each source well filled to the same level, and after each ejection an unused well is positioned above the wave-guide for ejection. In another variation, the user may keep the wave-guide in one position and either drain the liquid or add liquid in the source vessel or else raise or lower the source vessel to achieve incremental distances between the wave-guide and the liquid surface. In yet another variation, the system may also track the surface level of the source fluid through a fluid level detection device, and adjust the wave-guide accordingly in a predefined incremental step relative to the surface of the source fluid to plot the ejection profile.

Through the ejection profile mapped out in the above iterative process, the user or the computer system, with the assistance of software, may determine a range or ranges of positions (position of the wave guide relative to the surface of the source fluid) that may be used for each fixed amount of energy input.

The surface level or location of the source liquid may be determined through various methods. In one approach, the reflected acoustic wave after each ejection may be used to calculate the location of the source liquid surface. A separate acoustic wave may also be sent to provide the "ping" for measuring the location/level of the fluid surface base on the reflected acoustic wave. Alternatively, if the volume of the source liquid is known and the dimension of the vessel is also known, then the location of the source liquid surface may be calculated and tracked during the ejection process. If the size/volume of the ejected droplet at a particular power level is known, the amount of fluid being removed may be calculated based upon the number of ejections. Displacement of the source fluid surface level may then be calculated based on the amount of fluid that has be removed. A further refinement of the said method may also take into consideration other factors that may affect the liquid level contained within the source vessel. Examples of such factors include, but are not limited to, evaporation and moisture absorption by the source liquid.

The control system may tract the source fluid surface level, and adjust the location of the wave-guide when the source fluid surface level is going out of the preferred range defined by the ejection profile. Having pre-determined a preferred range for liquid ejection, the system does not have to adjust the position of the wave-guide as long as the position falls within the preferred range. However, the system may also adjust the position of the wave-guide after each and every ejection.

[b] Droplet Steering Mechanism

Figure 13A:
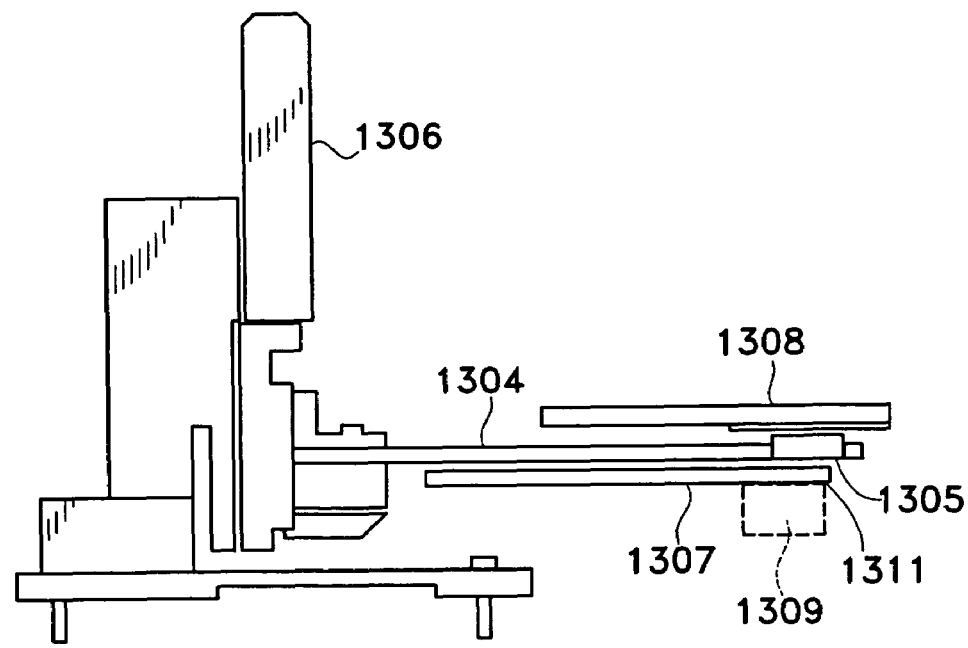
FIG. 13A shows a representative schematic diagram of a droplet steering mechanism attached to a position adjustment assembly, which may be integrated into a non-contact liquid transfer apparatus.

A representative schematic diagram of a droplet steering mechanism attached to a position adjustment assembly is shown in FIG. 13A. As seen, support arm 1304 extends from a platform, which may be manipulated via, e.g., z-axis adjustment assembly 1306, over a source liquid containment structure 1307. A droplet steering mechanism 1305, which operates according to the principles disclosed herein, is preferably located near the end of support arm 1304 and over the acoustic emitter device 1309. Steering mechanism 1305 is also preferably disposed beneath or adjacent to a target device 1308. As applied throughout, any number of structures may be movable along their x-, y-, or z-axis relative to one another, e.g., droplet steering mechanism 5, liquid containment structure 1307, target device 1308, acoustic emitter device 1309, may all be separately movable relative to one another or only certain structures may be movable depending upon the desired application. A detailed description of a droplet steering mechanism 1305 is disclosed in U.S. patent application Ser. No. 10/282,790 entitled "Apparatus and Method For Droplet Steering" filed Oct. 28, 2002, which is incorporated herein by reference in its entirety.

Figure 13B:
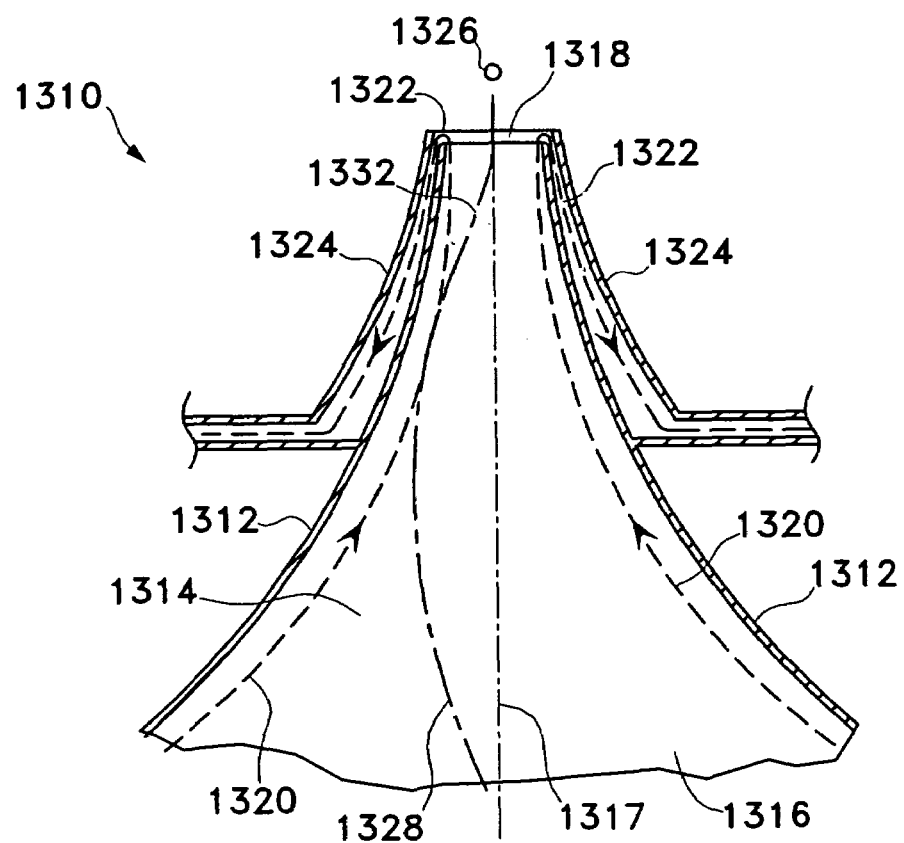
FIG. 13B shows a representative schematic diagram of a throated structure, which illustrates, in part, the general operation of the droplet steering mechanism.
Figure 13C:
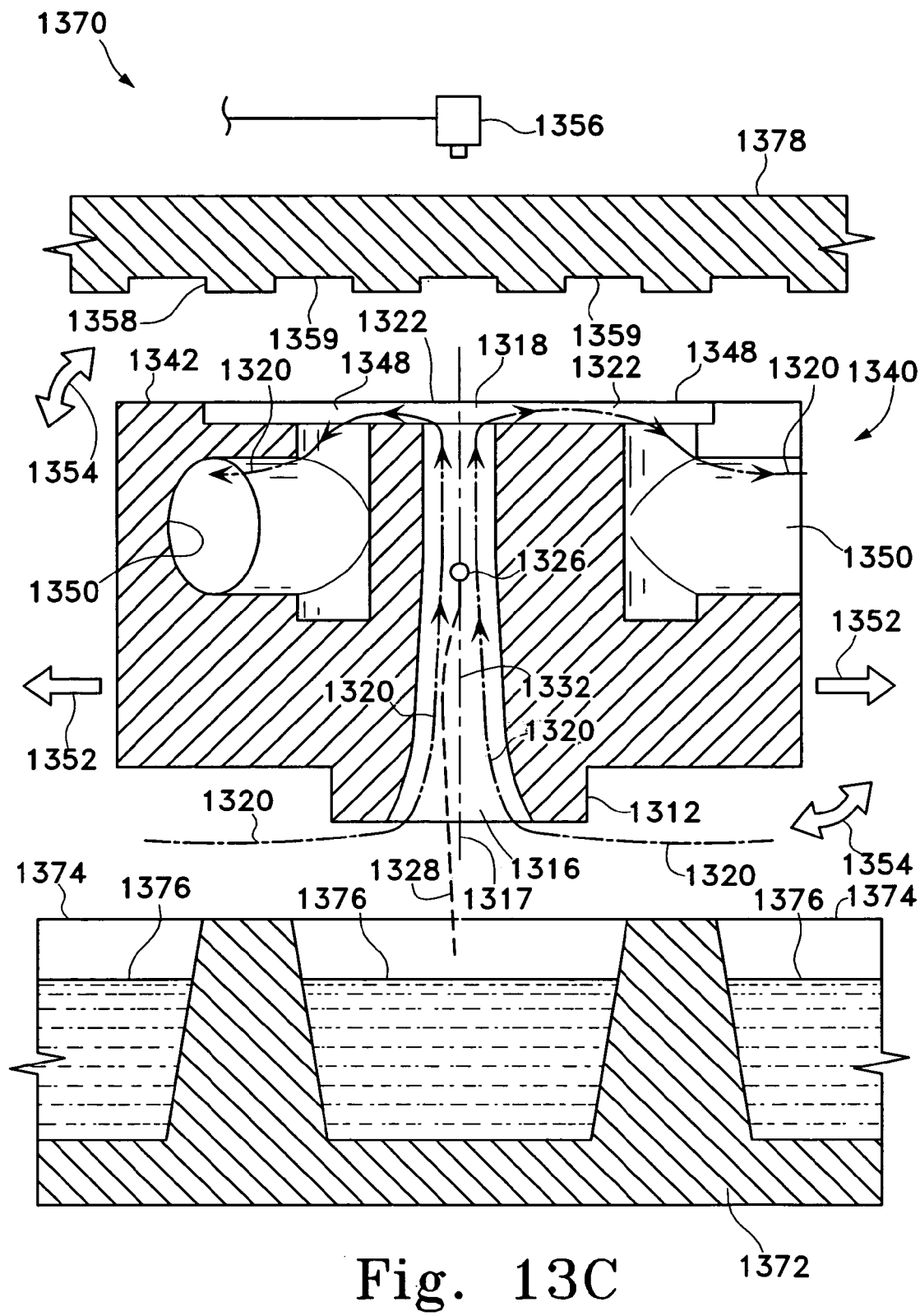
FIG. 13C shows an example of a droplet steering mechanism with a well plate and a target device.
Figure 13D:
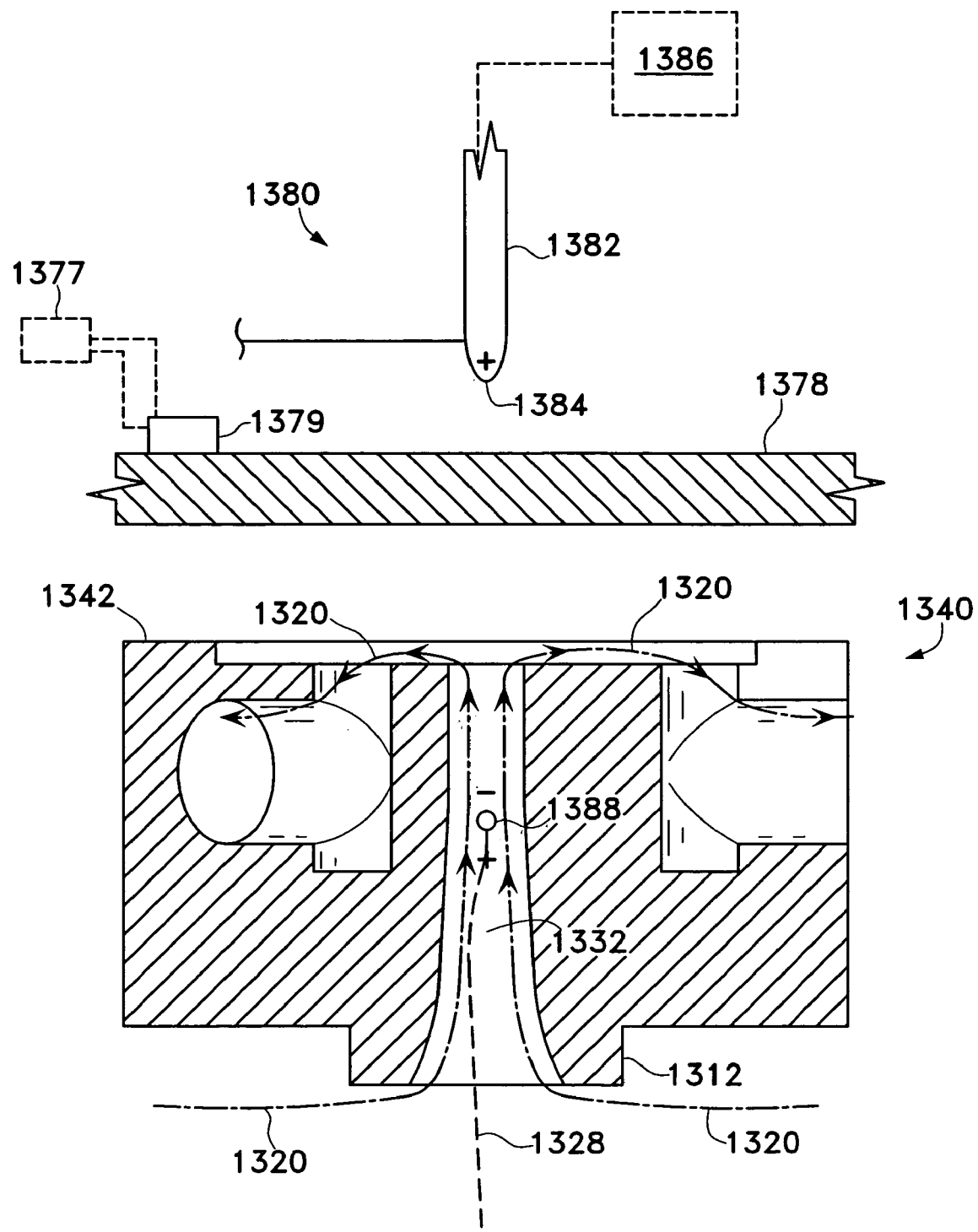
FIG. 13D shows another variation of the droplet steering mechanism with an electrically chargeable member positionable above the target device.

FIG. 13B shows a representative schematic of throated structure 1310 which illustrates, in part, the general operation of the droplet steering mechanism. Generally, throated structure 1310 may comprise a nozzle 1312 which defines throat 1314. Nozzle 1312 is preferably a converging nozzle, as described in greater detail below, having an inlet or entrance port 1316 and a preferably smaller outlet or exit port 1318. A vectored or directed gas stream, as shown by flow lines 1320, may be directed into inlet 1316 to be drawn through the structure 1310. As nozzle 1312 converges in diameter closer to outlet 1318, gas stream 1320 may increase in velocity and as stream 1320 approaches outlet 1318, it is preferably drawn away from the centerline 1317 of nozzle 1312 through deviated air flow channel 1322. Gas stream 1320 may be drawn away from throat 1314 at a right angle from the centerline 1317 of nozzle 1312 or at an acute angle, as currently shown. Gas stream 1320 may then continue to be drawn away from throat 1314 through outlet 1324 either for venting or recycling through inlet 1316 again. Gas stream 1320 may comprise any number of gases which are preferably inert, e.g., air, nitrogen, etc., or a mixture thereof. However, a reactive micro-droplet mist stream with a combined gas mixture containing micro-droplets may also be used as gas stream 1320. These micro-droplets in the mist stream are preferably about 100 times smaller than ejected droplet 1326 and may have specific properties that cause specified reactions to ejected droplet 1326.

As droplet 1326 is ejected from the surface of the liquid, it will have a first trajectory or path 1328. If the trajectory angle of droplet 1326 relative to a centerline 1317 of nozzle 1312 is relatively small, i.e., less than a few degrees off normal, droplet 1326 may pass through outlet 1318 and on towards target 1308 with some degree of accuracy. If the trajectory angle of droplet 1326 is relatively large, i.e., up to about ±22.5°, droplet 1326 may be considered as being off target. However, with gas stream 1320 flowing through structure 1310, a droplet 1326 may be ejected from a well located below structure 1310. As droplet 1326 enters inlet 1316 off target and as it advances further up into structure 1310, droplet 1326 is introduced to the high velocity gas stream 1320 at the perimeter of the interior walls of nozzle 1312, as seen at the point of capture 1330. Gas stream 1320 accordingly steers or redirects the momentum of droplet 1326 such that it obtains a second or corrected trajectory 1332 which is closer to about 0° off-axis. The gas stream 1320 at deviated channel 1322 is drawn away from the centerline 1317 of nozzle 1312 and although droplet 1326 may be subjected to the deviated vector of gas flow 1320, droplet 1326 has mass and velocity properties that constrain its ability to turn at right or acute angles while traveling at some velocity, thus droplet 1326 is allowed to emerge cleanly from outlet 1318 with high positional accuracy. Throated structure 1310 may correct for droplet 1326 angles of up to about ±22.5°, but more accurate trajectory or correction results may be obtained when droplet 1326 angles are between about 0°-15° off-axis for the given velocity, droplet size, and mass present in the current system. For example, a given droplet 1326 of water having a velocity of about 1-10 m/s, a diameter of about 10-300 microns with a volume of about 0.5-14,000 picoliters, and a mass of about 500 picograms (500×10-12 grams) to 14 micrograms (14× 10-6 grams) may have its trajectory correctable within the angles of ±22.5°, but the angles of correction are subject to variations depending upon the mass and velocity properties of the droplet 1326.

The use of such a system is not limited by the type of droplet ejection operation. For instance, droplets may be ejected with the acoustic emitter device 1309 in either pulsed or continuous motion. Pulsed motion may involve having a acoustic emitter device 1309 9 moved (relative to the source well plate) in discrete increments from one well, stopped long enough to emit acoustic energy into an individual well, and then moved again to another well to repeat the process (alternatively, the source well plate may move on top of a fixed acoustic emitter device). On the other hand, continuous motion generally involves moving acoustic emitter device 1309, and/or the well plate, in a constant motion while simultaneously emitting acoutic energy when positioned over a desired well to eject droplets. The droplet steering mechanism is not limited by the type of droplet ejection process but may be utilized in either, or any other type, of ejection process.

An example of droplet steering mechanism 1370 is shown in use in FIG. 13C. Main body 1340 is preferably located above the source liquid well plate 1372 which may contain a number of wells 1374 each having a pool of source liquid 1376, which may or may not be the same liquid contained in each well 1374. Target device 1378 preferably comprises a medium which is perpendicular to a longitudinal axis defined by the throated structure. Target device 1378 may comprise any medium, e.g., a glass slide, upon which droplets of liquid are desirably disposed and is preferably disposed above main body 1340, specifically above outlet 1318, for receiving the droplets ejected from source liquid 76.

Target device 1378 may comprise of a well plate as shown in FIG. 13C. Target well plate 1358 may be configured to have any number of individual target wells 59 for receiving droplets from different source liquid 1376 below. Moreover, target wells 1359 may be formed into various size wells which can correspond in size and relative spacing between wells 1359 to wells 1374 within the source well plate 1372, or they may alternatively be formed smaller or larger in size and relative spacing between wells 1359 depending upon the desired results.

In operation, droplet 1326 is ejected from source liquid 1376 by various methods, such as acoustic energy. Once ejected, droplet 1326 enters main body 1340 through inlet 1316 along a first trajectory or path 1328. The flow of gas, as shown by flow lines 1320, may be seen in this variation entering main body 1340 also through inlet 1316, although the gas may enter through separate gas inlets defined near the proximal end of nozzle 1312 in other variations. As the gas is directed through main body 1340, as shown by flow lines 1320, it may inundate droplet 1326 and transfer momentum to droplet 1326 to alter its flight path to a second or corrected trajectory 1332 such that droplet 1326 passes through outlet 1318 with the desired trajectory towards target 1378. Meanwhile, the gas is preferably diverted away from the centerline 1317 of the throat near outlet 1318 along air flow channel 1322, through routing outlet 1348, and out through gas outlet 1350. If droplet 1326 enters main body 1340 with a desirable first trajectory 1328, i.e., a trajectory traveling close to or coincident with the centerline 1317 of the throated structure, droplet 1326 may experience little influence from flow lines 1320 and accordingly little correction or steering, if any, may be imparted to droplet 1326. The gas may be pushed through mechanism 1370 through positive pressure via a pump (pump is not shown) that is connected to the main body 1340 or preferably the gas may be drawn through the system through negative pressure via a vacuum pump (vacuum pump is not shown) connected to the main body 1340 through gas outlet 1350.

During the droplet 1326 ejection process, if source liquids 1376 in wells 1374 are subjected to continuous or continual exposure to acoustic energy, the source liquids 1376 may be inadvertently heated as a result. Heating of the liquids 1376 may be an undesirable consequence since liquid properties may be altered. Therefore, the liquids 1376 may be maintained in each well 1374 at a constant predetermined temperature by controlling the overall temperature of source well plate 1372. This may be accomplished through various methods such as maintaining conductive thermal contact between a heat sink (not shown) and source well plate 1372. Alternatively or additionally, the coupling medium 1311 may be maintained at a constant temperature through various heating and cooling methods, e.g., compressors, Peltier junctions, etc. Maintaining coupling medium 1311 may help keep the contacting source well plate 1372 at a constant temperature through conductive thermal contact between the two. Moreover, to maintain constant temperatures (or to alter temperatures) the steering gas, as shown by flow lines 1320, may be heated or cooled appropriately by the use of, e.g., heat exchangers. Droplets 1326 which are ejected from source liquids 1376 may thus be heated or cooled by the steering gas as droplet 1326 traverses through nozzle 1312. Another alternative may include having target device 1378 or target well plate 1358 heated or cooled appropriately. For example, as seen in FIG. 13D, a heating or cooling unit 1379, e.g., a Peltier junction device which may be powered by a separate or common power supply 1377, may be in thermal contact with target device 1378 to provide the temperature control. Any one of these methods may be used independently or in combination with one another, depending upon the desired results.

For instance, examples of some of the possible combinations which may be utilized using any of the devices and methods as discussed above may include the following. One variation may include maintaining or altering the temperature of soruce well plate 1372 while also maintaining or altering one of the temperatures of coupling medium 1311, the steering gas, or target device 1378. Alternatively, coupling medium 1311 may have its temperature maintained or altered in addition to maintaining or altering one of the temperatures of the steering gas or target device 1378. Furthermore, the steering gas may have its temperature maintained or altered in addition to maintaining or altering the temperature of target device 1378. Alternatively, each of the temperatures of source liquid well plate 1372, coupling medium 1311, the steering gas, and target device 1378 may each be maintained or altered in combination with one another. These examples are merely illustrative of the possible combinations and are not intended to be limiting.

The main body 1340 may be further mounted or attached to a platform which is translatable in a plane independently from source well plate 1372 for use as a fine adjustment mechanism as droplets 1326 are ejected from the various source liquid 1376 in each of the different wells 1374. The translation preferably occurs in the plane which is parallel to the plane of source well plate 1372, as shown by the direction of arrows 1352 which denote the direction of possible movement. Although arrows 1352 denote possible translation to the left and right of FIG. 13C, movement may also be possible into and out of the figure. The degree of translation may be limited to a range of at least ±2 mm from a predetermined fixed neutral reference point initially defined by the system. Main body 1340 may also be rotatable, as shown by arrows 1354, about a point centrally defined within main body 1340 such that inlet 1316 is angularly disposed relative to the plane defined by source well plate 1372.

In operation, source well plate 1372 may be translated using, e.g., conventional linear motors and positioning systems, to selectively position individual wells 1374 beneath main body 1340 and inlet 1316. As source well plate 1372 is translated from well to well, time is required not only for the translation to occur, but time is also required for the source well plate 1372 to settle into position so that well 1374 is aligned properly beneath inlet 1316. To reduce the translation and settling time, main body 1340 may also be independently translated such that as source well plate 1372 settles into position, main body 1340 tracks the position of a well 1374 and aligns itself accordingly. Main body 1340 may be aligned by use of a tracking system such as an optical system, e.g., video camera 1356, which may be mounted in relation to main body 1340 and individual wells 1374. Video camera 1356 may be electrically connected to a computer (not shown) which may control the movement of the platform holding main body 1340 or main body 1340 itself to follow the movement of source well plate 1372 as it settles into position. Aside from the translation, main body 1340 may also rotate independently during the settling time of source well plate 1372 to angle inlet 1316 such that it faces the preselected well 1374 at an optimal position. The fine adjustment processes, i.e., translation either alone or with the rotation of main body 1340, may aid in reducing the time for ejecting droplets from multiple wells and may also aid in improving accuracy of droplets deposited onto target device 1378.

To further facilitate the droplet trajectory correction, another variation of droplet steering mechanism 1380 is shown in FIG. 13D, which shows the main body 1340 and target device of FIG. 13C with an additional electrically chargeable member 1382. Electrically chargeable member 1382 may comprise any electrically chargeable material, such as metal, and is preferably formed in an elongate shape, e.g., such as a pin. Member 1382 is preferably electrically connected to voltage generator 1386 which may charge member 1382 to a range of about 500-40,000 volts but is preferably charged to about 7500 volts. In operation, as member 1382 is electrically charged, the distal tip 1384 becomes positively charged. As droplet 1388 travels up to target device 1378, it becomes subjected to a high voltage static field and becomes polarized, as shown by the positive (+) and negative (−) charge on droplet 1388. The charge on distal tip 1384 and on droplet 1388 produces a dipole moment which acts to further influence the trajectory of droplet 1388 to travel towards the position of tip 1384. Thus, positioning of distal tip 1384 at a desired location above target 1378 allows for even more accuracy in depositing droplet 1388 in the desired position on target 1378 to within 10-50 µm. Droplet 1388 behaves as a dipole moving through an electric field in relation to distal tip 84 which preferably acts as a point charge.

[c] X/Y Linear Stage Assemblies

Various actuator and displacement device that can provide two-dimensional motions, which are well known to one skilled in the art, may be implemented here to provide movement to the handling device. In one variation, a X/Y linear stage along with its corresponding handling device is adapted for transporting well plates in and out of the process area above the acoustic emitter device and also to and from the well plate storage queue for load/unload. The X/Y linear stage may also provide sufficient freedom of movement within an X/Y plane so that each well on the well plate may be aligned with the acoustic emitter device.

One variation of an X/Y linear stage is described in detail below. The X/Y linear stage, as shown in FIG. 14, may be designed with a low profile and small footprint and could move a well plate in the X and Y direction with high running accuracy, high speed, and high acceleration. The X/Y linear stage may comprise two signal-axis linear stages assembled so that their line of action is at 90 degree to one another. Each single-axis stage is comprised of a base plate, a linear rail/carriage system, a moving coil/fix magnet linear motor, and limit and position sensors. A load arm is provide on one of the linear stage to which an holding device may be attached.

In this variation, the X-axis motion is provide by the line of action of the larger linear stage serving as the base of the linear stage assembly. The larger linear stage has a dual rail system 1402 with four linear bearings. The dual rail and four linear bearings may provide stability to the load arm 1404 when the load are is moved in the X direction. The Y-axis motion is provided by the line of action of the smaller single-axis stage attached to the larger linear stage 1408. The smaller linear stage has a one-rail 1410 system with two linear bearings. Aluminum may be used to fabricate some of the parts to minimize the weight of the system. The load arm 1404 may be fabricated from an aluminum thin wall rectangular tube.

In one particular variation, the X/Y linear stage has a maximum speed of 5 m/sec, acceleration of 2.5 g, stroke in the X direction of 340 mm, stroke in the Y direction of 100 mm, load on the Y direction linear motor is 3 kg, and load on the X direction linear motor is 10 kg. The X/Y linear stage has a base plate where the X-direction linear motor and X-direction rails are mounted. Two rails for the X-direction are mounted on a precision base block. Four linear bearings (two on each rail) are running over the two rails. These bearings are connected to each other and to the X-direction linear motor 1412 to make up the X-direction carriage. The X-direction carriage also works as the base for the Y-direction rail and linear motor. Two linear bearings are running over the Y-direction rail. These bearings are connected to each other and to the Y-direction linear motor to make up the Y-direction carriage. The handling device arm is mounted to the y-direction carriage.

Each carriage assembly (X and Y) may have limit sensors 1422 and hard stops 1424 on both ends to limit the stroke, an encoder 1426 to determine position of the carriage at any moment of the movement, and a home mark 1428 to establish a repeatable zero point (or reference position) when the machine is started up and during the process when needed.

There may be two cable tracks 1430 on the X/Y stage to provide safe cable routing. All cables and air tubes from handling device may be routed through handling device arm then joined with cables from the Y-direction linear motor and encoder and going through the top cable track. When they exit it they may join with cables from the Y-direction limit sensor, X-direction encoder and X-direction linear motor and enter the bottom cable track.

[d] Handling Device—Attached to the X/Y Stage Assembly

Various clamps, compression device, or non-compression holders or carriers may be implemented on the X-Y linear stage assembly for retrieving well plates from their storage queues. One variation of a handling device, a gripping assembly, is described in detail bellow.

Figure 15A:
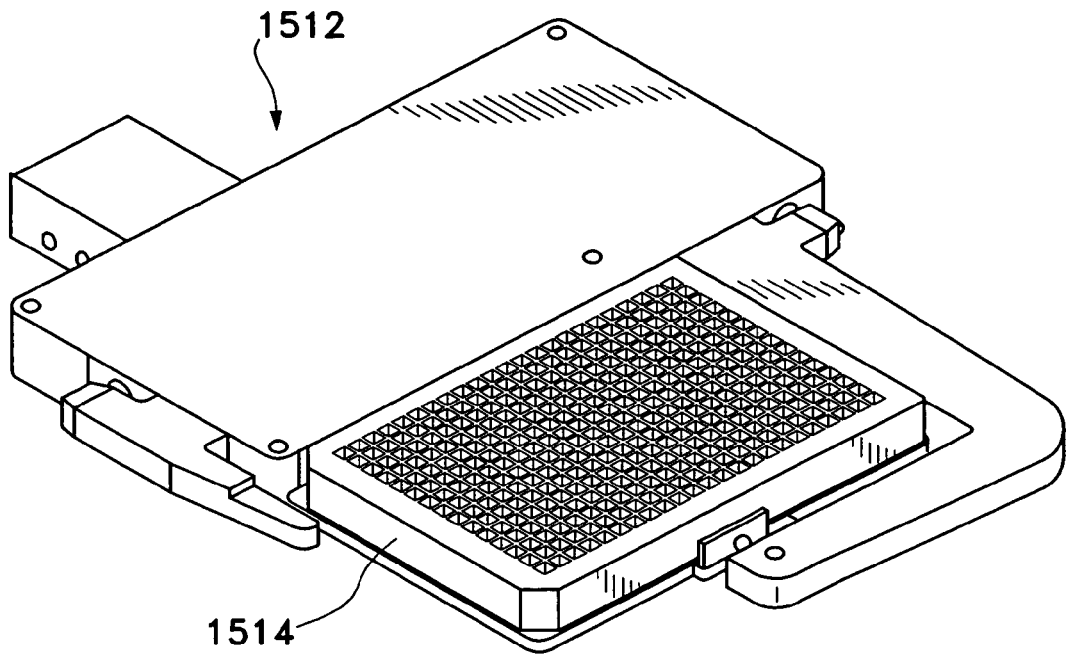
FIG. 15A illustrates one variation of a gripper assembly holding a well plate.
Figure 15B:
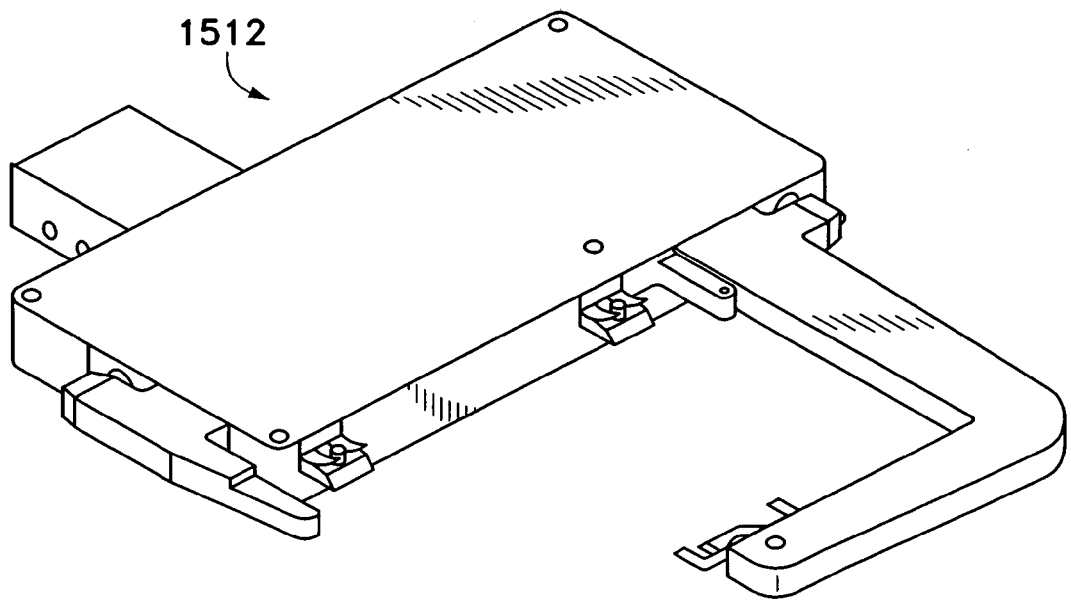
FIG. 15B illustrates the same a gripper assembly of FIG. 15A without a well plate.

The gripper assembly along with the X/Y linear stage performs the functions of retrieving/replacing well plates from/to the elevators (storage queues). The gripper assembly 1512, as shown in FIG. 15A, holds the well plate 1514 in a secure, predictable, and repeatable manner during transport of the well plate into and out of the central process area of the liquid transfer apparatus. FIG. 15B shows the gripper assembly 1502 without the well plate. In one variation, the liquid transfer apparatus has two grippers, a source gripper and a target gripper. The two gripper mechanisms may have similar design such that the two mechanisms comprise of approximately 80% common components. In one variation, the two gripper mechanisms may be identical. In another variation the target gripper is mounted inverted in liquid transfer apparatus in relation to the source gripper.

Figure 15C:
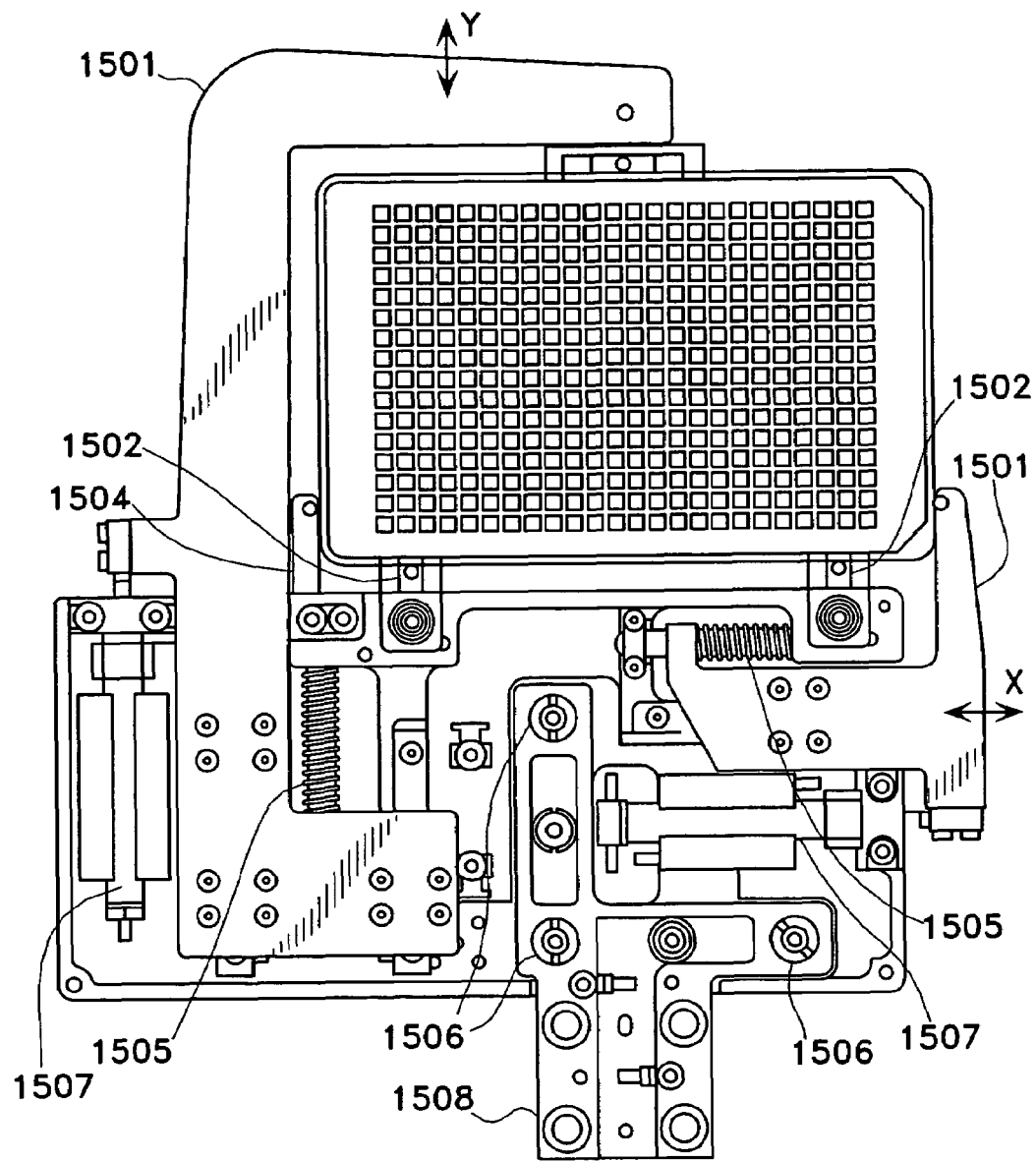
FIG. 15C illustrates the gripper assembly of FIG. 15A with its top cover opened showing various components within the gripper assembly.
Figure 15D:
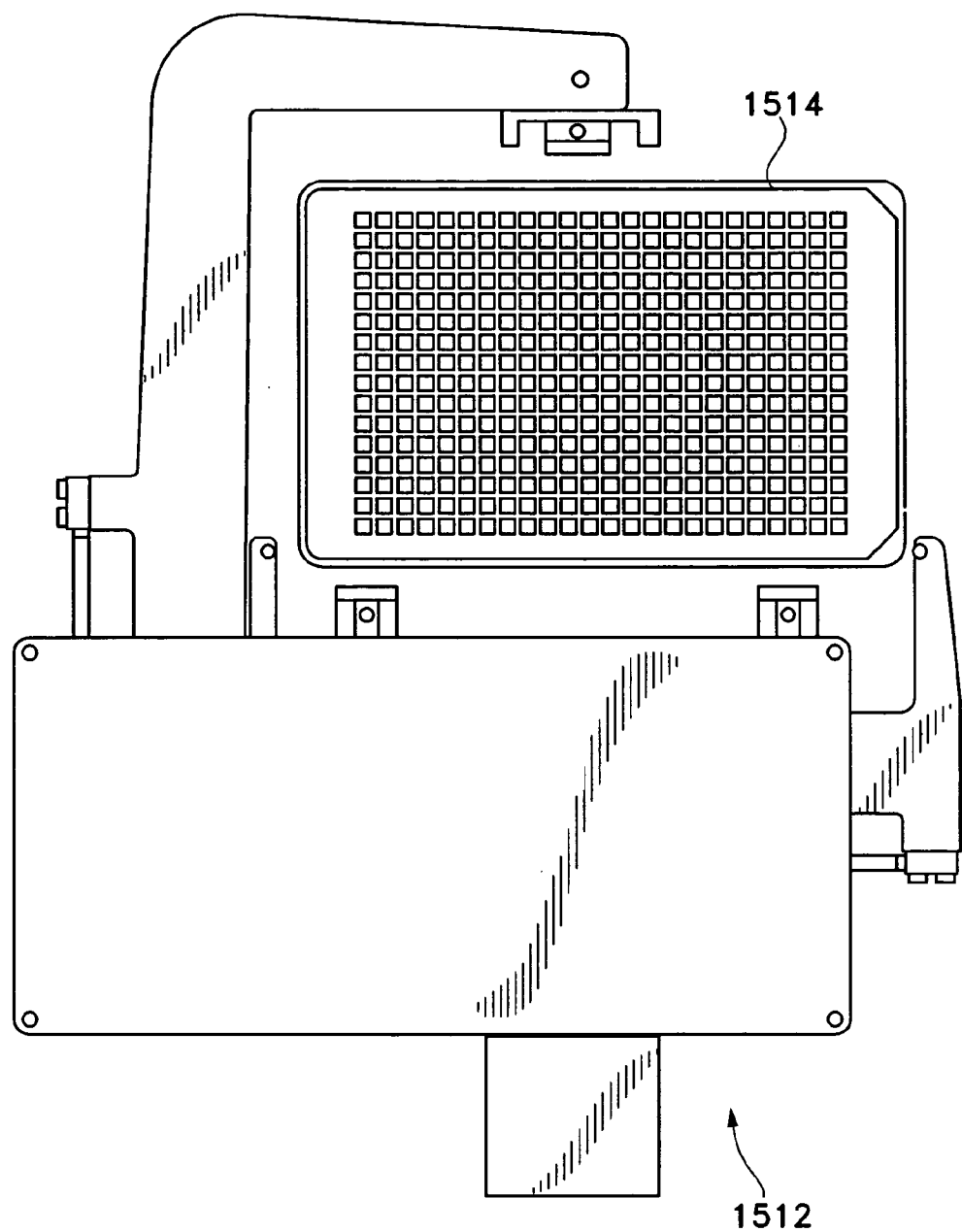
FIG. 15D illustrates the gripper assembly of FIG. 15A with the well plate up-gripped.
Figure 15E:
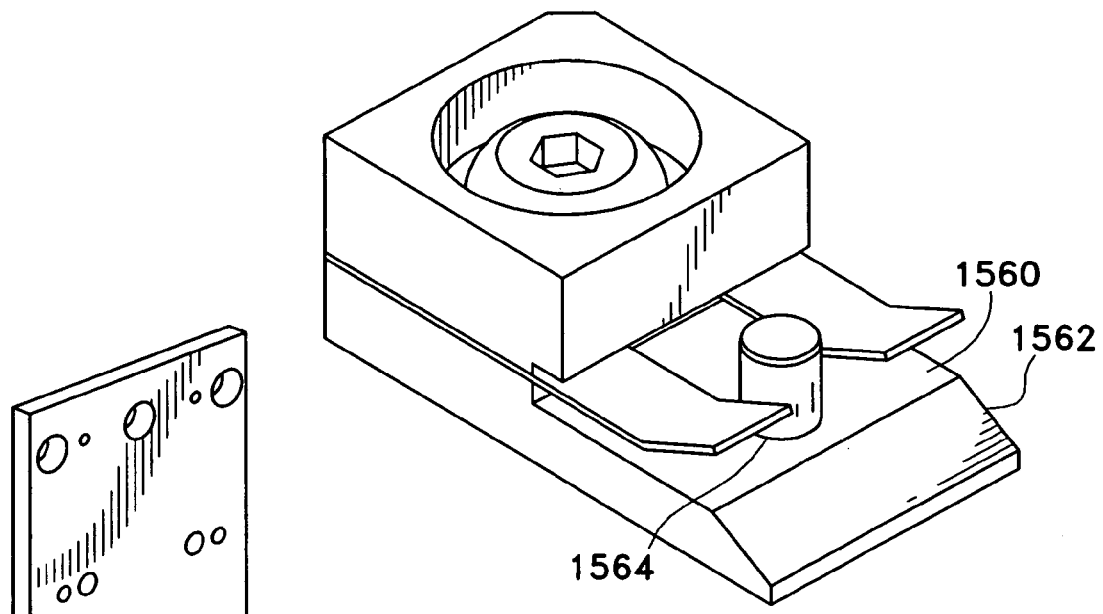
FIG. 15E illustrate one variation of an "finger" that may be attached to a gripper assembly to assist the gripper assembly to securely grip a well plate.
Figure 15F:
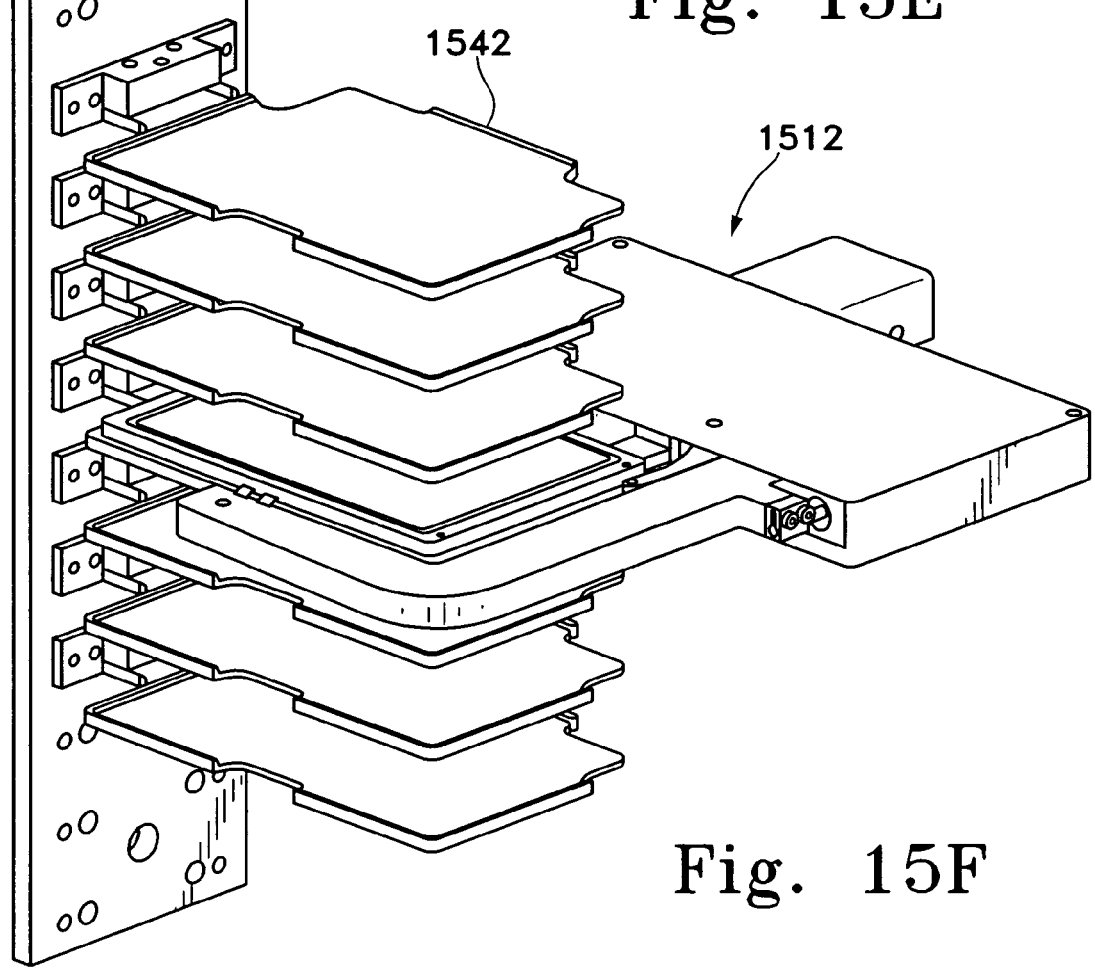
FIG. 15F illustrates the gripper assembly of FIG. 15A interacting with an elevator storage queue.
Figure 15G:
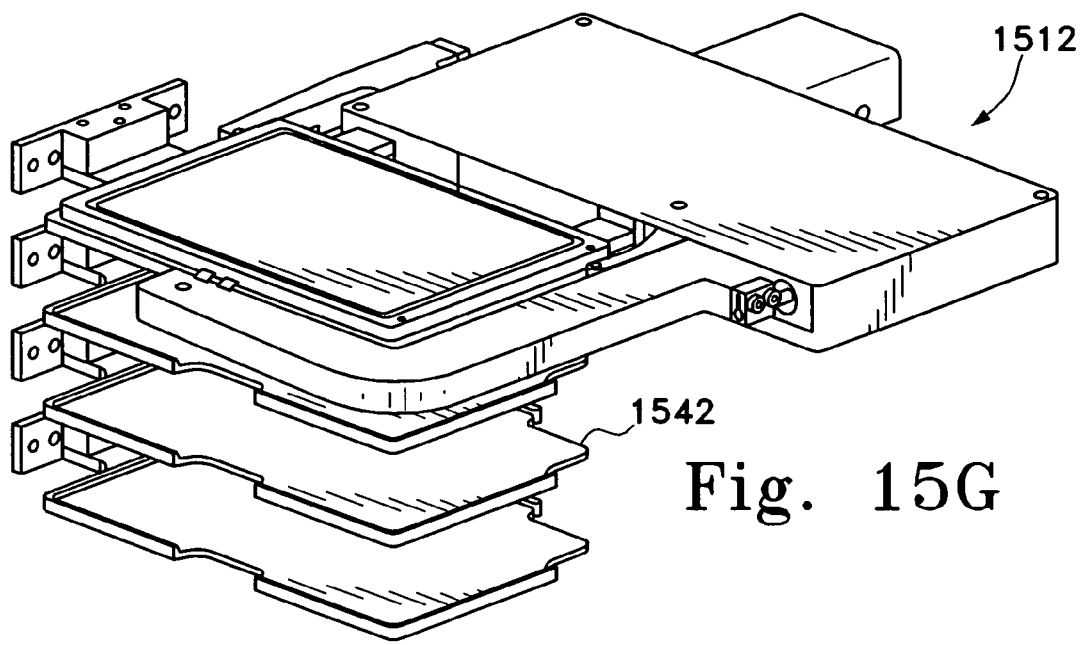
FIG. 15G illustrates the gripper assembly of FIG. 15A inter acting with an elevator assembly by gripping a well plate located within a slot on an elevator storage queue.

The gripper surfaces that come in close proximity to or contact with the well plate may have a slim vertical profile allowing them to fit into the elevator, between closely spaced shelves 1542, which hold the well plates, as seen in FIG. 15F. FIG. 15G illustrates a gripper 1512 interacting with an elevator and locking on to a well plate on one of the shelves 1542 to retrieve the well plate.

Figure 15H:
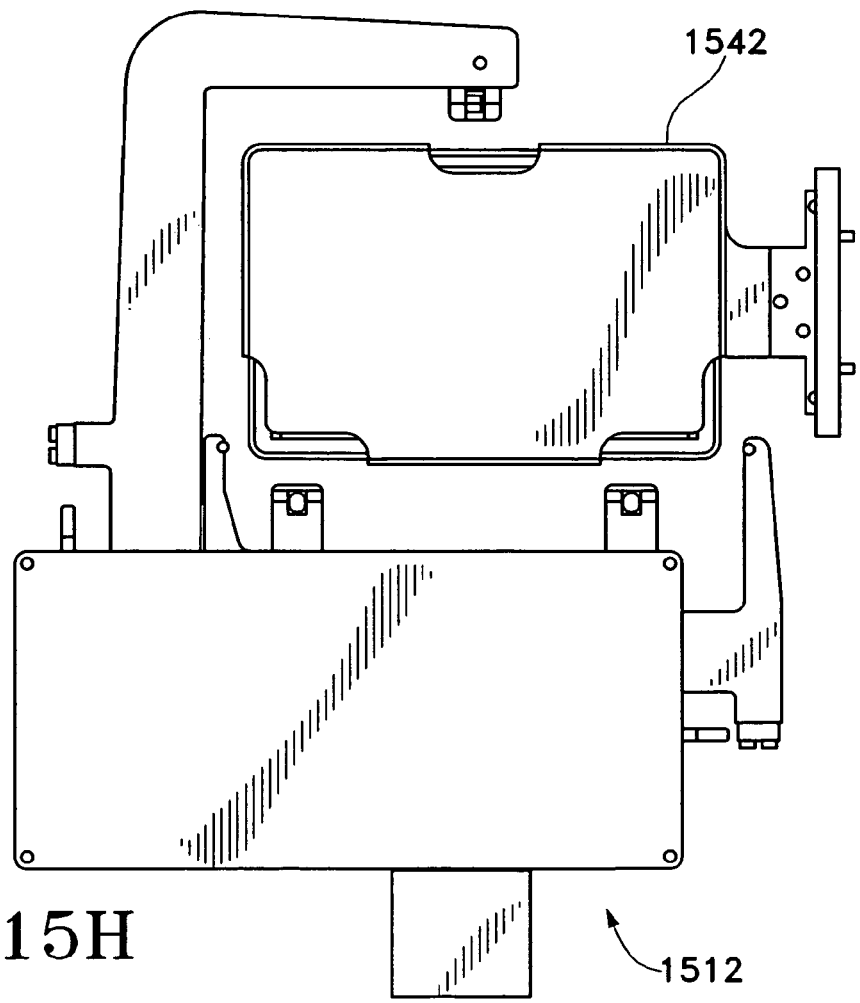
FIG. 15H is a bottom view of one combination of gripper assembly and elevator assembly, illustrating the elevator/gripper clearance. The gripper is shown in an un-gripped or expanded position.

Furthermore, in one particular design, the gripper 1512 in the open condition (well plate ungripped or released) clears all elevator components 1544 and well plates, as shown in FIG. 15H, allowing the elevator to move vertically without withdrawing the gripper out from within the elevator area. This design feature may speeds up the time to drop off one plate and then pick up another. The elevator does not have to wait for the gripper/stage to move and clear the area before it can move to another location on the elevator.

In another variation, the gripper grips a well plate with two linear moving axes 1501, an X-axis (transverse motion when viewed from the front of liquid transfer apparatus) and a Y-axis (longitudinal motion when viewed from the front of the liquid transfer apparatus). Each axis may be guided by linear bearings and driven by pneumatic cylinders with a spring return, as seen in FIG. 15C. The X-axis may press the well plate against a single fixed pin 1504, while the Y axis may press the well plate against two fixed pins 1502. These three fixed points (forming a wedge) may define the well plate position on a horizontal plane. By always biasing the plate against these stationary features, the "fixed points" being anchored on the gripper body, excellent position repeatability may be achieved within the gripper hold, each time the same well plate is garbed and secured in the gripper assembly. This design feature may also provide consistency in the position the gripper grabs different well plates having the same dimensional specification. For example, each well plate may be grabbed in the same way, in approximately the same location.

In one variation, the gripper's two axes are driven open by pneumatic air cylinder and closed by compression spring 1505. This configuration may provide fail-safe operation wherein a well plate remains securely gripped in the event of a system failure, power outage or loss of pneumatic pressure. Each pneumatic cylinder may have two position sensors attached: one sense fully open condition, the other fully closed position. The position in which a well plate is properly gripped is between open and closed and there for doesn't trigger either sensor. FIG. 15D shows the pneumatic air cylinder being activated to release a well plate.

The gripper assembly may also include a set of three fine-thread screw 1506 assemblies providing leveling and positioning functions for the gripper as an assembly. Mounted between the gripper body and the mounting interface, the tree assemblies can be adjusted uniformly or differentially. Uniform adjustment moves the X-Y plane of the gripper assembly up and down in the Z direction with respect to the liquid transferring apparatus. Differential adjustment tilts the X-Y plane of the gripper with respect to the X-Y plane of the liquid transfer apparatus. The mounting interface 1508 of the gripper may utilize precision locating pins to allow for simple yet precise removal and replacement of the gripper from the X/Y linear stage assembly.

Furthermore, three horizontal surfaces 1506, one on the moving Y arm and two at the Y fixed pins 1564, may define the horizontal plane X/Y for the well plate to be secured in the gripper. The horizontal surfaces may have lead-in ramps 1562, which allow a well plate to be picked up even if the well plate is poorly aligned with the gripper assembly.

In one variation, the three horizontal surfaces defining the X/Y plane for the well plate are located on three Y-axis fingers. Each of the three Y fingers have a flat surface, paralleled to the X/Y plane, on which a griped well plate rests, defining the Z position of the well plate. Since two of the surfaces, located on two fixed fingers 1502, are stationary, and the third moving surface, located on one moving finger 1503, is guided by precision linear bearing, the positional repeatability may be very good. The fixed and moving well plate contact features, or fingers, on each gripper assembly, may including ramp features 1562, as seen in FIG. 15E. The ramp 1562 or angled lead-in surface to guide the well plate as it is being gripped. With long X and Y strokes and generous finger lead-in surface, the gripper can grasp a well plate that is poorly aligned (e.g., tilted from the X-Y plane of the gripper) relative to the gripper. The three Y-axis finger sets may be removable and replaceable. This may allow the gripper to be adapted to various well pates and microtiter plates that are commonly used in the industry by simply replacing the figure set with an appropriate matching finger set.

[e] Storage Queues

In one variation the storage queues comprise of elevators located within the liquid transfer apparatus for holding the well plates. Computer and/or feedback control mechanisms maybe connected to the elevator's actuator or displacement mechanisms for queuing of well plates in an automated process system. Barcode scanner may be integrated within the elevator such that the bar code on each well plate may be scanned and the system control computer may track the location of each well plate within the storage queue. For example, bar code scanner may be positioned at the level where the gripper assembly retrieves the well plate. The system may scan the bar code on the well plate to verify the specific well plate being retrieved each time. The elevator may move vertically and transport specific well plate in the storage queue to a gripper presentation position for access by the gripper assembly. When the well plates within the elevator queue are not in use, the elevator may be lowered into a storage and/or climate cavity within the liquid transfer system. In one variation, there are two elevators, one for source well plates (left position from the front of the liquid transfer apparatus) and one for target well plates (right position from front of the liquid transfer apparatus). The two elevators may be constructed of the same mechanisms.

Figure 16:
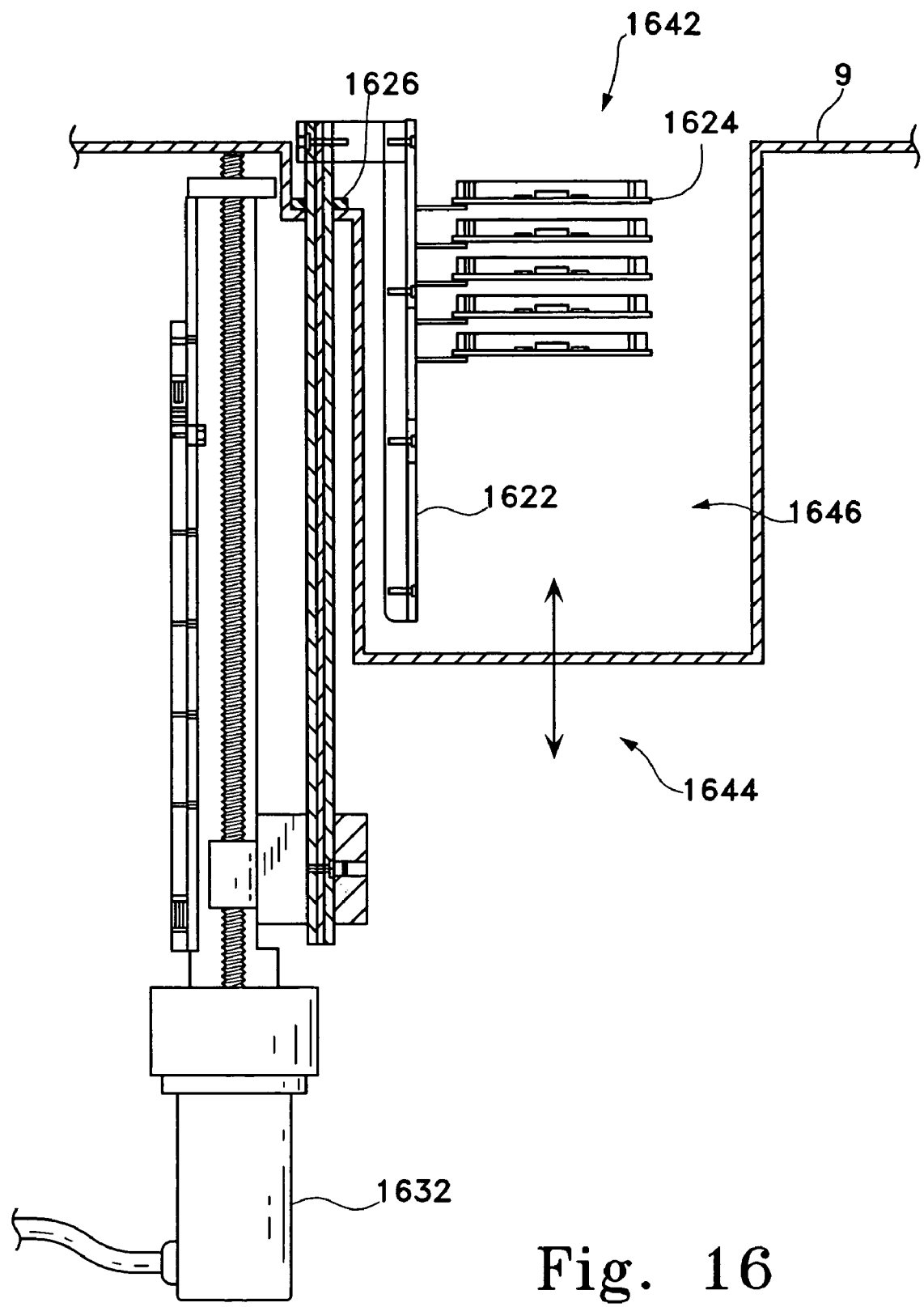
FIG. 16 illustrates one variation of an elevator storage queue.

The elevator may comprise of a vertically mounted, linear motion assembly, a well plate back plane 1622 with individual shelves 1624 for well plates, and a sliding seal assembly 1626, as shown in FIG. 16. The back plane is the plate at the back of the storage queue where each of the individual shelves 1624 mounts. The linear motion assembly may comprise of two linear beating units, a ball-screw drive, and a servomotor 1632 with an integral brake that provides load holding when the elevator is not in motion. In one variation, the well plate back plane 1622 may have as few as one shelf for a single well plate, or up to twelve shelves for twelve well plates. With an extended linear system and backplane, additional well plate capacity may be implemented in the elevator assembly, as one skilled in the art would appreciate. Different shelves may be interchanged on the elevator backplanes to store different varieties of well plates. A sliding seal 1626 assembly may be provide to maintain separation between the climate controlled area 1642 of the system where well plates reside, and the non-climate controlled area 1644 where the servomotors 1632, linear systems, and related components reside.

In one design variation, the elevator storage queue is normally positioned down in the lower storage area 1646 below the processing deck 9. The storage queue may be moved up so that each well plate within the storage queue may be scanned when it passes a barcode reader, which may be positioned just beneath the processing deck. Alternatively, the barcode scanner may be positioned above the processing deck. The storage queue may also move up above the processing deck to present a well plate to the gripper for entry into the process area. Barcode scanning may also take place while the storage queue is being raised for presentation of well pates for processing.

The elevators may also be completely raised above the processing deck to present all the shelves in the elevator for manual (operator) insertion, removal and/or replacement of well plates. In another variation, modularized rack may be provided such that a complete set of well plates (e.g., set of 8 or 12 well plates) may be inserted or removed from the elevator queue. In yet another variation, the elevator may receive one or more modularized queues or racks. For example, each elevator may be designed for receiving one 12-plate rack, or two 6-plate racks, or three 4-plate racks. In another design variation, access to the storage chamber below the processing deck is provided, such that operator may replace the well plates while the elevator queue is sitting in the storage chamber below the processing deck.

[f] Image Detection System

The image detection system may be used as an alignment device to precisely align the source and/or target well plates to the vertical axis of the acoustic emitter device. The image detection system may also be implemented for tracking the liquid ejection process and/or provide post ejection liquid transfer verification. Furthermore, the image detection system may also be used for monitoring and or measuring reactions within the wells by detecting and/or recording signal due to chemical reactions, fluorescent markers, or other reactions which emits light or changes transmission or absorption of lights in substances within the well. Other light sources may also be adapted within the system to enhance the capability of the image detection system. For example, IR beam may be position below the well plate, which is aligned with the imaging system, for measurement of IR abortion of materials within the wells. In another variation, UV light source (e.g., a xenon lamp) may be positioned above the well plate that is aligned with the imaging system, for exciting fluorescent markers. Other light source and/or corresponding chemical markers well known to one skilled in the art may also be adapted for used in the present invention.

Figure 17A:
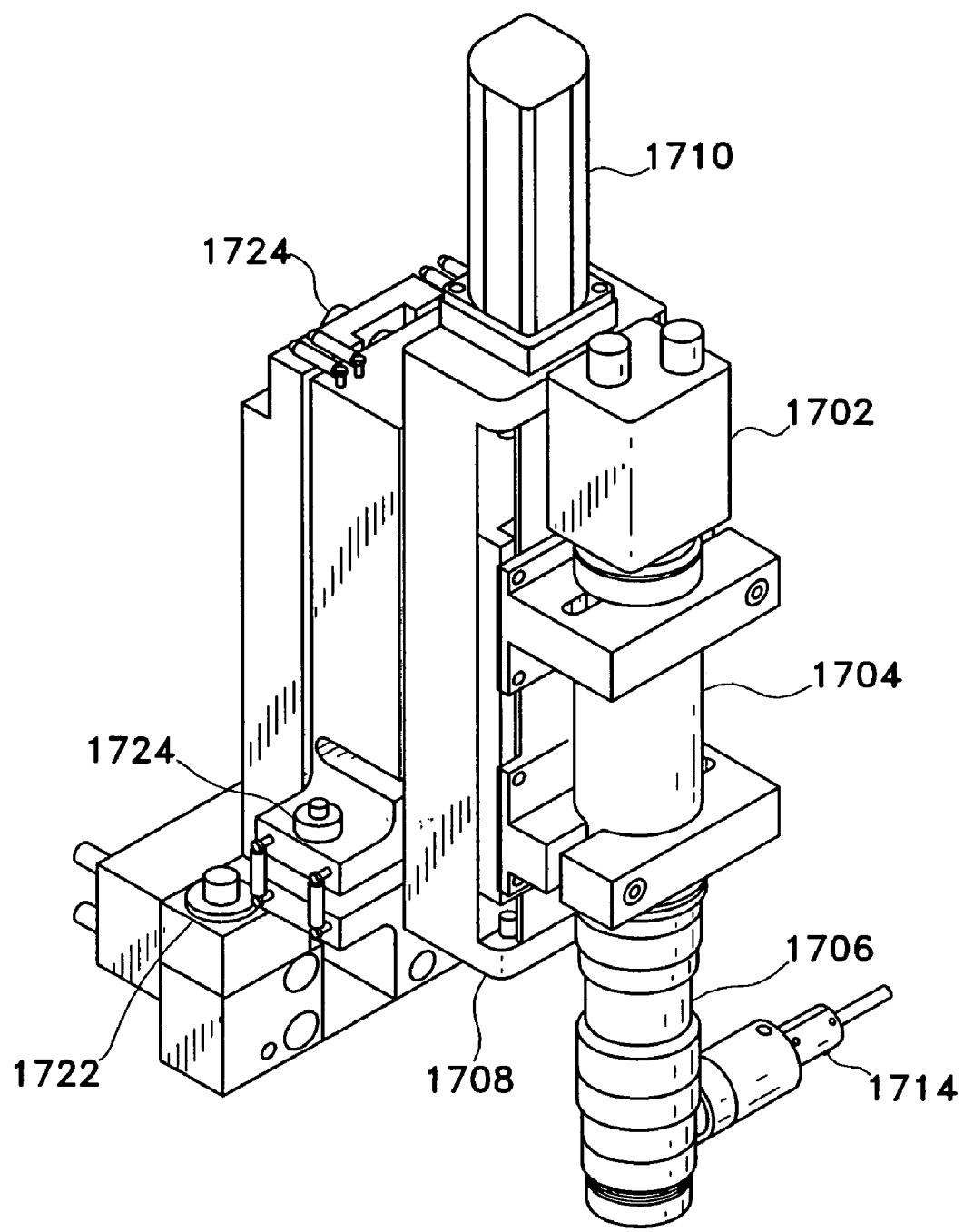
FIG. 17A illustrates one variation of an image detection system.

In one variation, the image detection assembly is comprised of a digital camera 1702 mounted on the end of an optical tube 1704; as seen in FIG. 17A. A lens assembly 1706 may be mounted on the opposite end of the optical tube 1704. The entire tube assembly may be mounted on a linear slide carriage 1708 with two clamps. The linear slide may be driven with a servomotor 1710 in the z-axis (in the vertical direction), so that the camera 1702 is able to focus on objects that are sitting on different levels/planes. A linear slide may be mounted on a block 1712 that has alignment features used to align the camera with the transporter. The lens assembly may have an LED light source 1714 in order to illuminate the object being viewed. Other light source (e.g., a halogen light bulb) may also be used to provide illumination. In one variation, an IR LED light source may be used to illuminate the object being viewed. Appropriate filters may be implemented to filter extraneous light, and thus, provide good contrast ratio in the image captured by the image detector. For example, IR light may be implemented to illuminate the fiducial marks on the source and target well plates. Corresponding high-pass and/or low-pass optical filter may be implemented to improve the signal-to-noise ratio for the illuminated fiducials. The filters may improve the contras ratio between the fiducial mark(s) and its surrounding area on the well plate. Other filters, both optical and digital, that are well known to one skilled in the art may also be implemented to enhance the edge detection capability of the image detection system.

Alternatively, a UV light source may be used to provide photo excitation. In one variation the fiducial marks are coated with UV excitable materials. In another variation the chemical in the source liquids are tagged with UV excitable chemical markers. Light splitting device (e.g., a light-splitting prism) may also be implemented to direct illuminating light source down the camera's focus path. A light splitting device may also be implemented to diver part of the light going toward the camera to a separate light/image detection/recording device. The camera axis of the image detection assembly may be mounted in such a way that it remains fixed to the center axis of the transporter assembly (waveguide/fluid basin unit).

In one variation, the image detection assembly attached to a precision angle alignment mount that sits on a X/Y alignment mount 1722. The X/Y alignment mount may provide a rough alignment in the X and Y direction, and precision angle alignment mount 1724 provides rotational freedom in the X/Z plane, so that operator may manually adjust the position of the image detection system to align it with the acoustic emitter device. Actuators may also be adapted to the adjustable mount so that the alignment of the image detection system may be corrected by a computer.

In another variation, the source or target well plate is moved under the camera to four taught (or predefined in the control system) positions, one at a time, so that fiducial at each of those four positions is in the camera's field of view. The vision system captures an image of each fiducial. Then the software calculates the fiducial's pixel location in the image, in pixel coordinates (or the systems reference coordinates). By using the camera calibration factor these pixel locations may be converted into X-Y coordinates (world coordinate systems). Software may then use these four fiducial locations to determine the orientation of the source and target. These source and target orientation data may then be implemented to calculated orientation angle to move to specified source and target locations, so that source and target locations are in line with the acoustic emitter device and the camera center.

In another variation, the fiducial marks are configured of materials with suitable contrast differential compared to the surrounding area (or background) of the fiducial marks. For example, white fiducial marks may be implemented on a black well plate. Alternatively, the marks may be black while the well plate is white. It is preferable that there is a high contras ration between the fiducial mark and its immediately surrounding area.

Figure 17B:
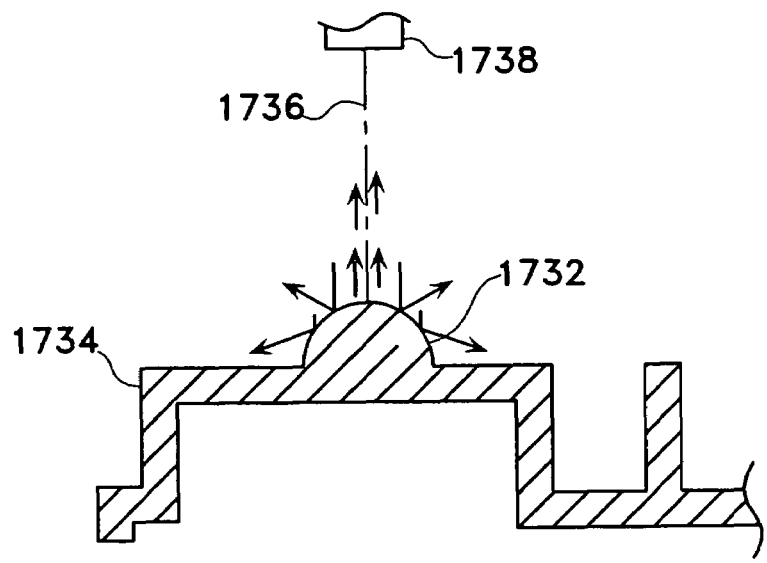
FIG. 17B illustrates the imaging detector capturing reflected from a spherical fiducial mark that are parallel to the image system axis.

In another variation, two-dimensional circular dots and/or three-dimensional spherical features 1732 may be placed at the corners of each well plate 1734 to serve as fiducial markers. Spherical features are particularly useful since only reflected light on the optical axis 1736 of the image system will be detected by the detector 1738. The center of the sphere provide good reflection while the peripheral area tend to reflect light at an angle from the image detector's axis 1736 and away from the image detector, as illustrated in FIG. 17B. This result in a sharp image of a fiducial mark created by the sphere which may be easily capture and processed by the image detection system. Comparing the spherical feature to a flat circular feature, a flat surface surrounding the circular feature tend reflect more light and may cause an edge-effect where the circular feature comes into contact with its surrounding area, and thus, causes a loss of resolution.

In one variation, the spherical features 1732 are reflective spheres (e.g. metallic spheres) position on or within a well plate. It may be beneficial to place the spherical features within the well plates since the reflective surface of the sphere will be protects from abrasion or other damages when well plates are handled or stacked for storage or transport.

Figure 17C:
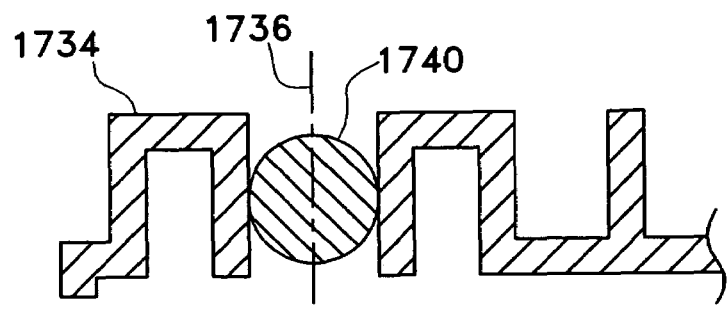
FIG. 17C illustrates one variation of a fiducial mark formed with a reflective sphere embedded in a well plate.
Figure 17D:
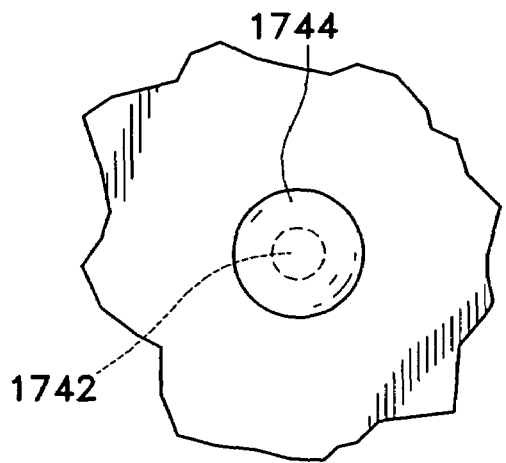
FIG. 17D is a plan view of a spherical fiducial mark.

In one example, holes are drilled in the four corners of a well plate 1734 and then stainless steel ball bearings 1740 are pressed into each of the four holes, as illustrated in FIG. 17C. When viewed by the image system, excellent contrast may be achieved between the well plate and the ball bearing. In addition, since the ball bearing is spherical, pin-point reflection of light is captured by the image detector, since the center region 1742 of the sphere produce good light reflection on the Y-axis and the peripheral region 1744 of the sphere reflects light way from the Y-axis, as seen in FIG. 17D. Thus, the image captured by the image detector may be smaller than the diameter of the ball itself. It is preferable that the fiducial is a highly reflective surface with a small area reflecting light back to the image detector to create a sharp image with high contras ration with the background.

As an alternative to fiducial marks, existing features on the well plate may be used as fiducial or registration marks. For instance, the image detection system may detect the edges of a selected well (e.g., the well in the first row and first column) and the software could calculate a point representing the center of the well. A second well (e.g., the well in the first row and in the last column) may also be detected and its center calculated. Base on the position of the center of the two wells the system may then map out the position of the well plate on the X-Y plane.

Although an image detection system is implemented in the above variations for detection of source and/or target plates' location, one skilled in the art would appreciate that other object detection approaches may also be implemented along with the image detection system or in place of the image detection system. For example, acoustic detection, optical/laser detection, capacitive, inductive or pressure sensing approaches that are well known to one skilled in the art may also be implemented independently or in combination to facilitate the alignment of source/target plates. Efficient and effective detection of source and target plates allows alignment of selected source well and selected target well with the acoustic emitter.

In one variation, arrays of laser sources and arrays of corresponding sensors are configured above the acoustic emitter for detection of source and target plate positions. The laser/sensor arrays may form a three dimensional matrix and capable of determining the specific locations within this matrix that are occupied by an object. The position and/or orientation information of the plates is collected by a computer for calculating the amount of misalignment. Base on the position information from the detectors, the computer may generate a coordinate system representing the source or target plate, and then, through comparison with a standard coordinate defined by the system be able to precisely position the plate within the standard coordinate. Thus, base on the coordinate information the computer will be able to control the X/Y linear stages and their corresponding handling devices to align a specific well on the well plate with the acoustic emitter.

In another variation, actuators are placed around an area above the acoustic emitter. When a plate is moved into the ejection area above the acoustic emitter, the edges of the plate will apply pressure to the actuators, thus allowing the computer connected to the actuators to detect the position of the plate. For example, the actuator may be place in a "L" shape configuration, and the source or target plate is place within this L shape boundary when the plate is slide into its pre-assigned position above the acoustic emitter. The pressure or displacement exerted on the actuators along the "L" shape boundary allows the computer to calculate the amount of misalignment on the X/Y plane and make necessary adjustments to ensure proper alignment between the source plate, the target plate and the acoustic emitter. As one skilled in the art would appreciate, the actuator and/or other sensors may be placed in various other configurations for detection of the source and target plates' position.

In yet another variation, electromagnetic waves, sound waves or light waves are propagated toward a source or target plate place above the acoustic emitter. The reflected sound or light wave is capture by sensors and used to calculate the position of the plate.

In one variation, the acoustic wave emitter for liquid ejected is also used for the detection of the source fluid containment structure's position. Acoustic waves are propagated from the acoustic wave emitter through the coupling medium toward the fluid containment structure. The reflected acoustic wave is captured by a sensor and processed by a computer to determine the position of the source fluid containment structure.

Makers, fiduciary markers, other energy reflective/absorptive targets, and/or other two or three-dimensional features may be place on or within the source and target plates to assist the corresponding sensors to detect the source and target plates during the alignment processes. For example, a prism or other refractive materials may be place on the corners of each well plate. When the well plate is position above the acoustic emitter, a laser beam is directed into one side of the refractive material and exits the other side. A sensor is position to detect the angle of the exiting laser, and base on this information the amount of misalignment may be calculated. The position of the well plate may then be adjusted so that proper alignment may be achieved.

[g] Machine Controls, Electronics and Software

A control system may be provided to provide overall control of various components and device in the liquid transfer apparatus. In one variation, the control system comprises a single board computer mounted on a computer rack mount chassis with a passive back plane. The computer board may have PCI and ISA bus where additional controller may be connected to the main control system. FIG. 18A illustrates one variation of a control system layout with centralized control for all the control components. A motion controller may be implemented to control the 8 axes of motion in the X/Y linear stages, storage queue elevators, camera focus, and acoustic emitter focus. All of the axes may have an encoder to provide precise location feedback, and home and over-travel sensors for setting a reference location and prevent over extension of the mechanisms, respectively. An RS 232 controller may be implemented to communicate with the barcode scanners, which scan barcodes on the target devices and the source vessels. A RS 485 controller may be implemented to send commands to controllers for controlling relative humidity, temperature and/or inner gas pressure in the process area. A signal synthesizer may be used to generate an electric signal, which is amplified by an amplifier to drive the acoustic emitter device. The signal synthesizer may be any signal generator, well known to one skilled in that are, that is able to generate a signal of desired frequency and amplitude. An amplifier may be provided to amplify the signal to appropriate amplitude to drive the acoustic emitter device if the signal coming out of the signal generator does not have enough strength. A high-speed analog to digital controller is used for reading signal back from the acoustic emitter device. Software may be implemented to process the feedback signal in order to determine the output signal for the signal synthesizer. There may be one high bandwidth analog-to-digital controller. There may be a digital I/O controller for monitoring and controlling all the digital I/O signals on the machine. There may also be an analog I/O controller for monitoring and controlling all the analog I/O signals on the machine. The analog I/O controller may be used for controlling devices that are controlled by analog voltage, and also used for reading low bandwidth analog signals. A vision controller may be implemented for garbing images from the camera system and feeding the digitized image to an image processing software for processing (e.g., feature extraction, image measurements, pattern recognition).

Figure 18B:
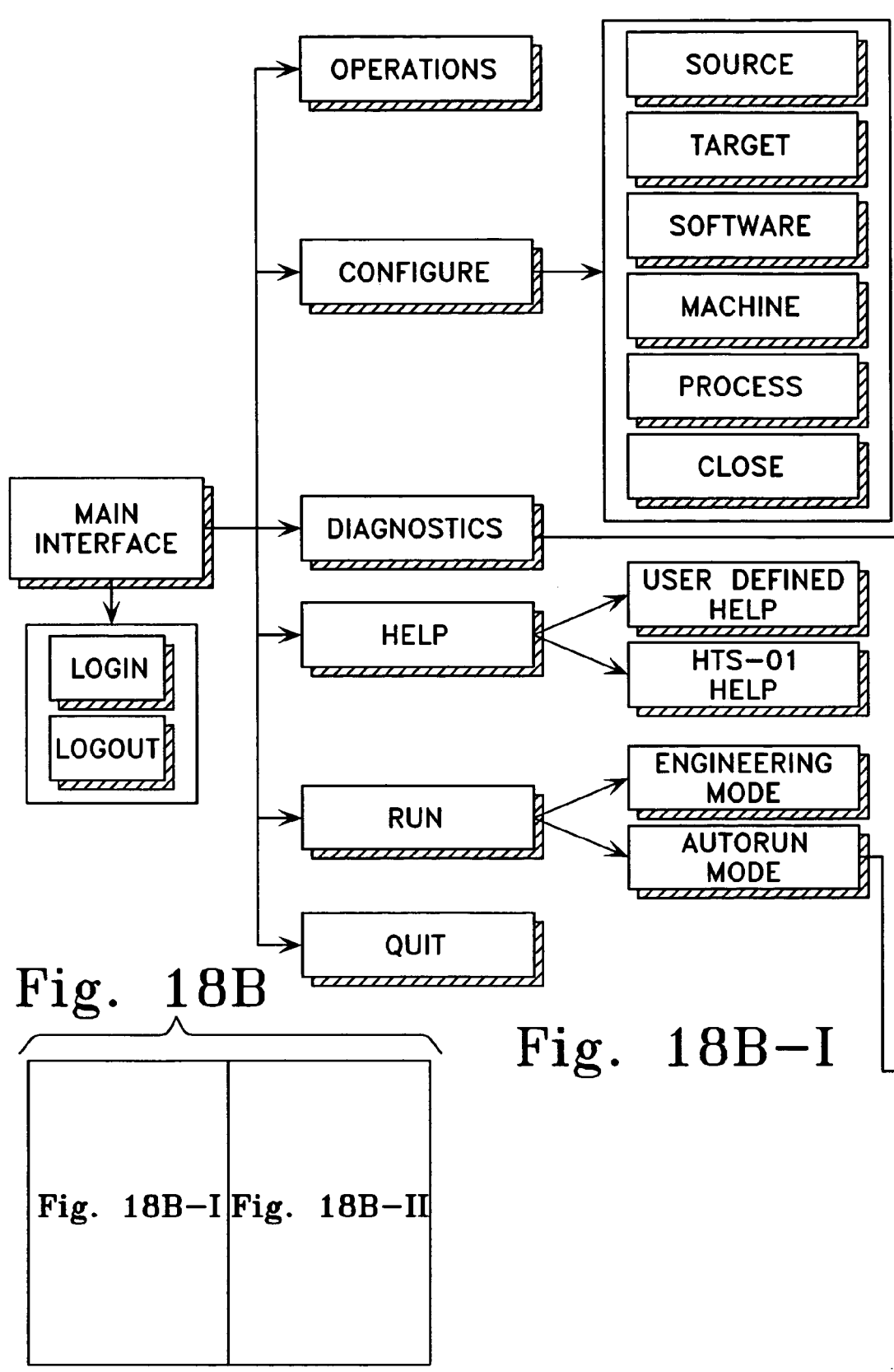
FIG. 18B shows one variation of a software block diagram.

Various software may be implement in the control system for controlling different components, and for processing signals received by the system. In one variation, a system control program is implemented on a computer within the control system. The software architecture for this particular variation of system control program is shown in FIG. 18B. Modular software design is implemented in this system program, which uses handshakes to communicate among the various modules within the system. This flexible architecture allows for relatively easy addition of new modules and relatively easy removal of existing module. Graphical users interface, with various menu options, gives the user access to various control parameters and allows the user to navigate through different options easily.

In this variation, the main interface, which is the highest level in the menu structure, allows user to login into the software. Once the user is logged in, user may have various level of access/control of the system depending upon the level of access that was prescribed to the particular user.

The Operation menu may allow the user to access different operations of the machine. For example if user wants to turn the coupling liquid On/Off or the user wants to change the flow rate of the coupling liquid, an option may be provide to control such parameters. In another variation, the user may be able to prescribe specific locations on the storage queues to retrieve source and target well plates.

The configuration menu allows the user to configure different part so the system. For example, it may allow user to provide source vessel and target device configurations. The user may be able to specify length, width, height, number of row and columns, acoustic parameter for material of the source vessel, etc. Software option may allow user to add, delete, and change user information, including defining user access level. Under machine and process menus, user may configure various hardware parameters and define variables for the operation process.

The diagnostic menu allows the user to access digital I/O's, analog I/O's, motion control, and vision system. By selecting the digital I/O panel, the user may control digital output, and monitor digital inputs. Analog I/O panel allows the user to read analog inputs and send an analog voltage out of an analog output port. The "setting" panel allows the user to specify the volume calibration factor and volume per drop in picoliter increments for the acoustic ejection of the liquid transfer apparatus. The "motion control" panel allows the user to change or teach a position specified in the position database. The user may provide calibration setting or operate the system to teach the system location parameters for specific operation to be stored in the position database. The position database may contain information defining a location for fiduciary marker alignment check, a location for retrieving a well plate from a storage queue, and the like.

User may go to a position where the system had already been taught by selecting the particular position button. The "modular test" panel provides operation for editing elevator sequence and for testing system functionality of the elevator. The "vision system" panel allows the user to monitor images being acquired by the vision system in real time. This panel may also allow user to access camera calibration and image measurement utilities. In one variation, by using parts measurement function, the user may measure a part or object that is placed on one of the x-y stage under the camera. This may be achieved, for example, by moving the x-y stage precisely so that the center location of the camera focus move from one edge to a second edge of a part or object being track by the image, while simultaneously recording the amount of displacement. Alternatively, object measurements may be achieved by pre-calibrating the image system and using image-processing software to calculate the object size base on the image captured by the image system.

The help menu provides access to basic help functions that are programmed into the system software, and allows user to defined specialized help functions that may be customized by individual user. The basic help function may additionally have access to on-line help, which may provides user with information on how to run, calibrate and maintain the machine. It may also provides access to specifications, images, drawings of the different parts of the machine The run menu provides different operation modes that may be selected by the user. Submenus are also provided for user to monitor and/or change control parameters for computer controlled operations.

Software or system program may provide automated and precision control for the liquid transfer apparatus to achieve high throughput operation and ensure synchronization between various components within the system. Various software architecture and codes well known to one skilled in the art may be implemented to provide the user interface and system controls describe above.

Software may also be implemented for selecting specific wells on the source vessel and ejecting the selected source liquid in to predetermined target locations on the target device or target well plate. User may also program the software with specific ejection sequence to transfer a series of liquids out of their corresponding wells into a series of receiving target wells.

In one aspect of the invention, an algorithm implemented in a computer program may be used to optimize motion profile for the ejection sequence, so that liquid may be transferred in an efficient manner from a plurality of source well to target wells. For example, the user may provide a list of predefined sources and their corresponding target locations. The list of source and target locations may be described as a multidimensional array. Each coordinate describes the position of the Source X, Source Y. Target X and Target Y. An additional dimension (e.g., source or target plate ID) may be added if multiple well plates are used for either source or target. A computer program may calculate the optimal ejection sequence to optimize the performance of the system. In one variation, the computer may calculate the optimal ejection sequence to minimize the amount of time needed to transfer all the liquids from their sources to their corresponding targets. In another variation, the algorithm may sort the list in such a way that the total motion required is the shortest total path for the axis that moves the longest total distant. This may be calculated by adding the distances of each move for each axis. For example, assume a coordinate system in which the origin of the coordinate system is in the lower left-hand corner of each well plate. Consider four points for simplification: (0,0,0,0), (15,15,0, 1), (0,1,0,2), and (15,18,0,3). The total distance moved for each axis by doing these in the given order is [45, 46, 0, 3]. However, by sorting them to the following order: (0,0,0,0), (0,1,0,2), (15,15,0,1), and (15,18,0,3), we have a total distance of [15, 18, 0, 5]. Many other sorting techniques, which are well known to one skill in the art, may also be applied in this system.

One particular approach, which requires minimal amount of computing time, is described below. Based on the list of source and target locations provided by the user, the computer first sorts the source positions so the ejection sequence moves from left to right and then right to left on the next row on each well plate; and from the top source well plate down to the bottom source well plate in the corresponding sequence in the elevator queue, if the sources reside on more than one well plate. Once the source sequence is selected, the corresponding target sequence is determined based on the source target relationship defined by the list of source and target locations provided by the user. Since the computer determines the ejection sequence, the user may provide multiple pairs of source and matching targets in any order and let the computer sort out the optimal sequence for processing.

In another variation, where more than one source liquid is to be delivered into each target well, and a particular delivery sequence is desired, the user may prescribe the specific sequence of ejection by entering it into the system directly for processing. Alternatively, more elaborate sorting/optimizing algorithm may also be implemented to determine the desired ejection sequence.

[h] Database

One of the applications of the liquid transfer apparatus is to take liquids contained in one or more source liquid containment structures and transfer them to one or more target devices, and being able to define the precise location to transfer each liquid droplets and at the same time track the liquid transfer process with a database(s). The database(s) allow the user to determine precisely the individual liquid pools that are generated on the target and may also allow the user to go back and verify the liquid transfer process.

The source liquid containment structure(s) may have an associated database comprised of a plurality of data inputs, e.g., fluid type, fluid surface tension, fluid viscosity, fluid location (within the containment structure), age of fluid (when it was created), where it was created, how often it has been used, first time and/or last time used, amount of fluid, etc. The database may allow the user to tie whatever information that may be useful to the individual liquid pool on the liquid containment structure. Information regarding each liquid containment structure, such as bar code for each structure, may also be tied to the other entries in the database.

A "mapping profile/database" may be provided to instruct the liquid transfer apparatus as to which source liquid it is to transfer to what target device/target location. The apparatus' internal software may take this mapping profile and formulate a preferred optimized sequence for fluid transfer to minimize the time to complete the total number of transfers.

In addition, a similar target device or output database may be loaded onto the apparatus. The output database may have similar data regarding liquids on the target device. In some cases, the output database might be "empty" because the user is using new/empty target devices. In other cases, the user may utilize target devices containing liquid(s), and information regarding each liquid pool and its location on the target devices may be provided in a database. In cases where new/empty targets devices are used, the system may generate a new output database as needed. Identification or registration information may be provided to link individual entries in the database to individual target device or a set of target devices.

After liquids are transferred, both the source and target databases may be updated with new information. In one variation, at the end of the liquid transfer process the liquid transfer apparatus provides the following information to a database: the source liquid containment structures (with less liquid in them), the target devices with added liquid, and corresponding database (s) with information corresponding to each pool of liquid on the source and target plates. One database may be provided and contain both the source and target information. Alternatively, a source database is provided with information regarding all the liquids in all the source plates, and a separate target database is provided with all the information regarding all the liquids in all the target plates. It is also feasible to provide individual databases for each source and each target plate.

In one aspect of the invention, a database is provided to manage various input and output data. The database may also be used to track change in the source liquid library and provide reference information for the output target liquid library. The system controller may collect and store data during real-time operation of the machine to track resource distribution and/or for future analysis.

Figures 19, 19A:
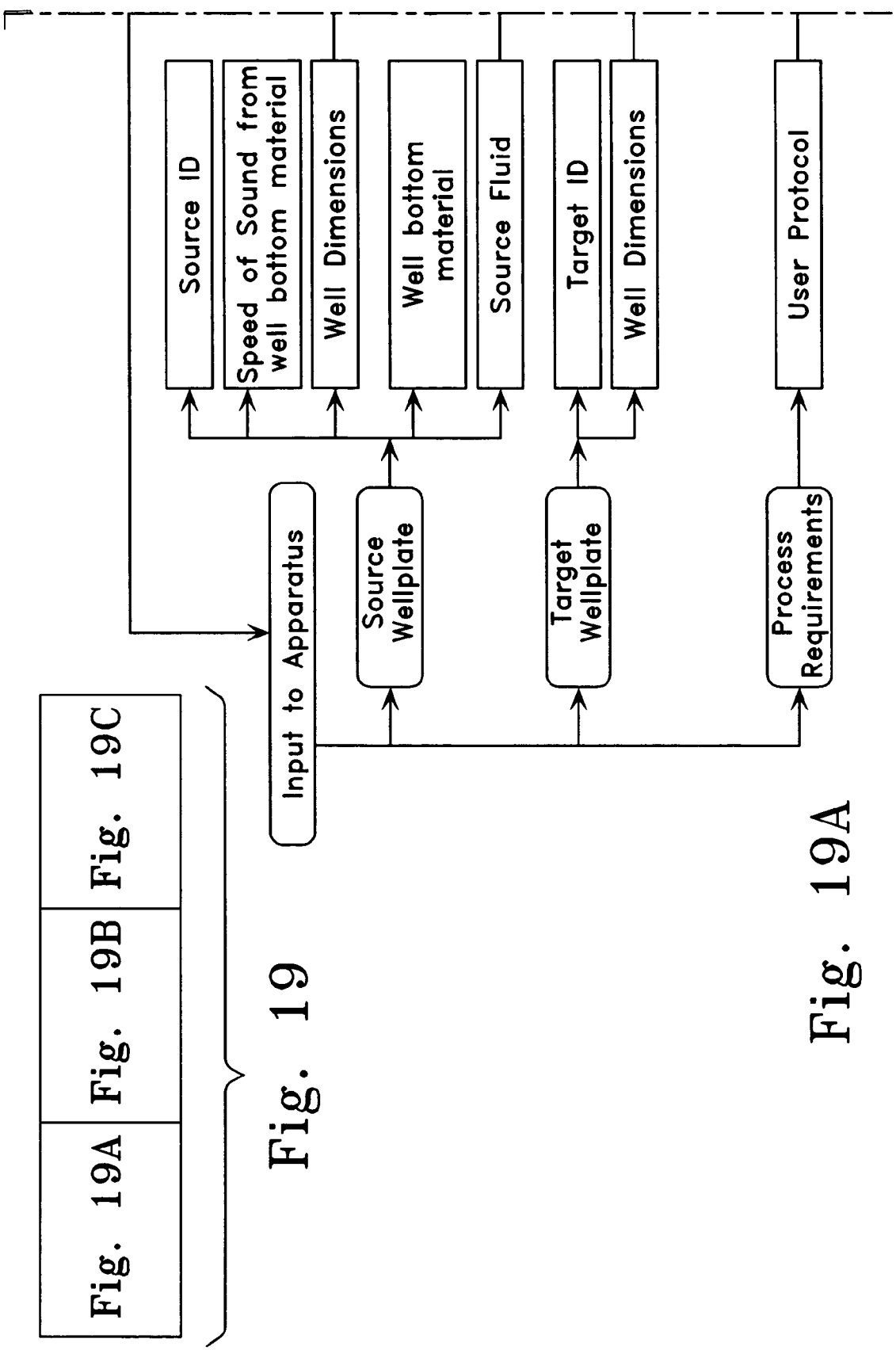
FIG. 19 shows one variation of a database management system block diagram.
Figure 19B:
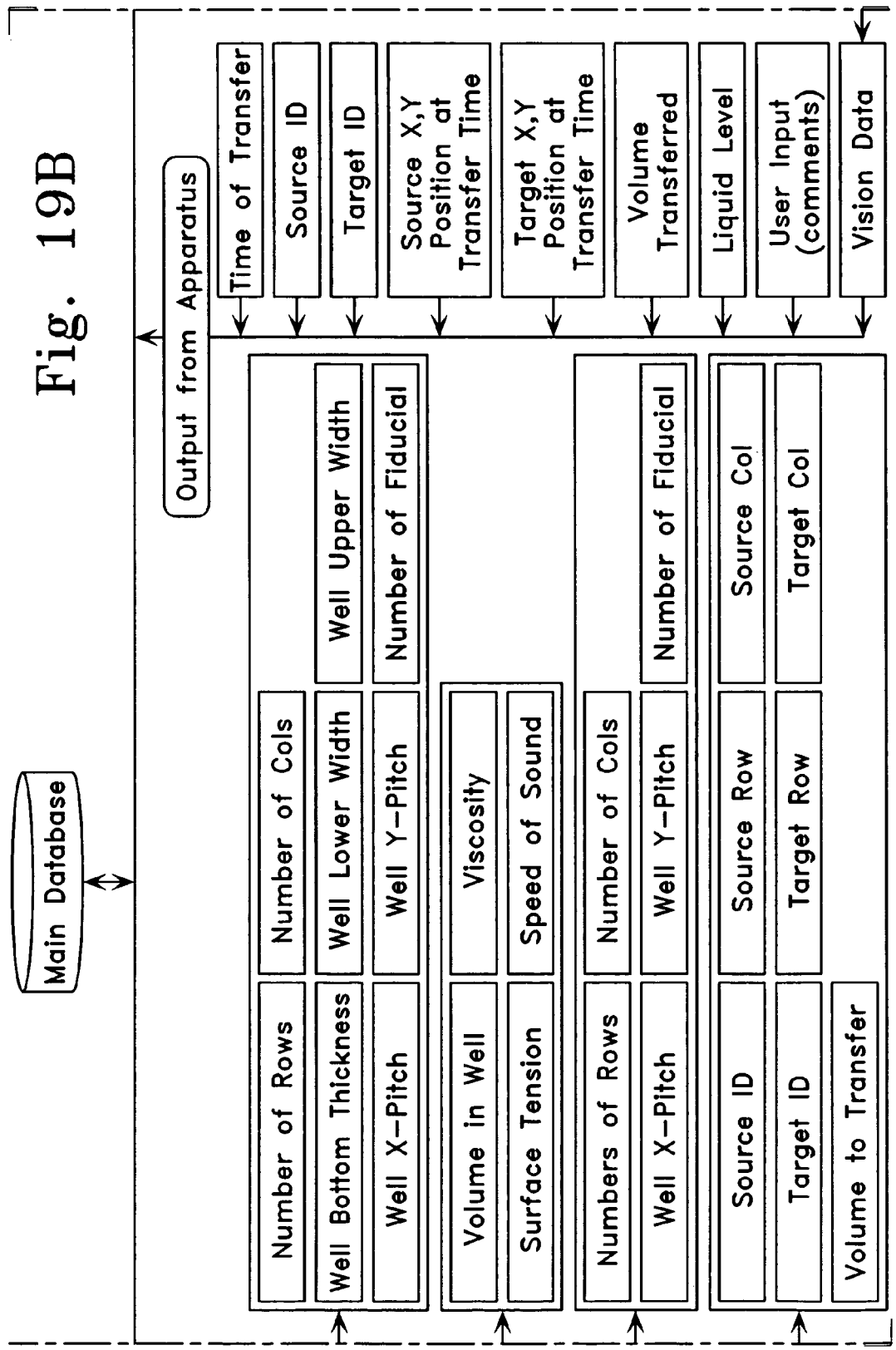
Figure 19C:
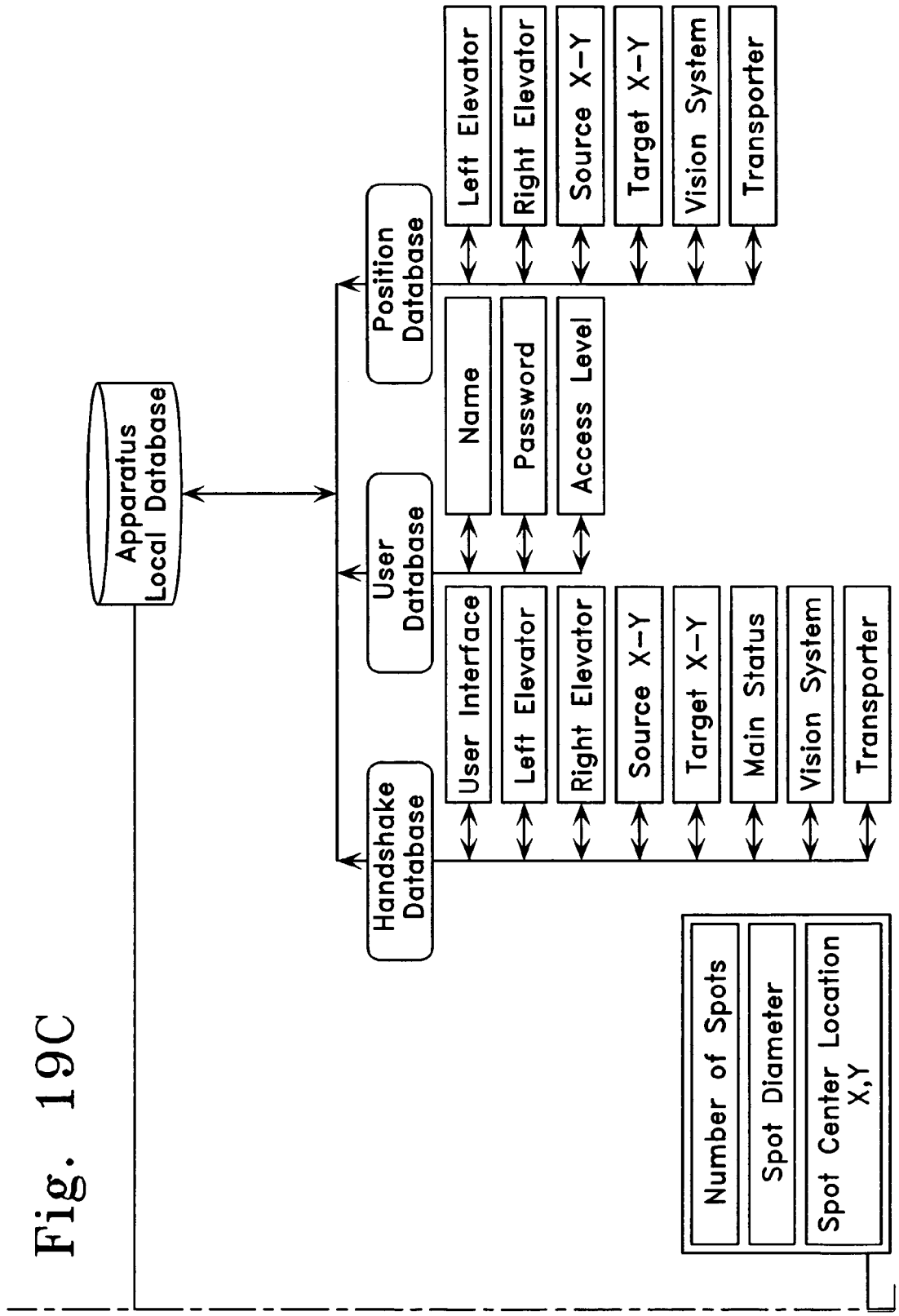

In another variation, the database management system comprises a main database and a local database. The main database may contain all the information that is required by the control system and store the data collected in real time. As seen in FIG. 19, one variation of a database is illustrated. The main database provides various information to the system controller to support the operation of the system, as seen in "Input to Apparatus" in FIG. 19. In this variation, the main database reside on a central system, which is separate from the local computer that controls the liquid transfer apparatus, and provides the liquid transfer apparatus with source/target well plate information and process requirements such as a mapping profile. The main database also received output information from the liquid transfer apparatus, as shown in "Output from Apparatus" in FIG. 19.

The computer controlling liquid transfer apparatus may maintain a local database. The local database maintains information that is unique to the liquid transfer apparatus, which it supports. The local database may include information such as handshake information, which supports communication between different mechanisms and devices within the liquid transfer apparatus, user information, which provides user access information, and position information, which provides operation parameters for the different mechanisms and devices that makes up the liquid transfer apparatus.

Various information may be provided by the main database to support the operation of the liquid transfer apparatus. For example, information regarding the source well plate are provided so the system may properly identify specific source wells for liquid ejection. Physical and material characteristics of the plate, dimension of the well, pitch of the well in X and Y direction (distance between the wells), thickness of the plate at the bottom of each well, characteristic of the source liquid including volume, depth of the liquid and physical and characteristics of the liquid may also be provided, so that acoustic waves may be appropriately directed to achieve ejection of a portion of the source liquid. Information regarding the plate(s), the well(s) and the liquid(s) contained within each well, may allow the control system to calculate the proper placement of the acoustic wave focus and the desirable amount of energy to generate for each ejection. Information regarding the target well plates may be provided so that the system may properly identify the specific target location that will receive each ejected droplet or droplets. Physical and material characteristic of the target well plate, such as material characteristic and dimension and of each well may also be provided to assist in the placement and alignment of the target. Information regarding fiducial marks or other feature on the target/source plates may also be provided. The fiducial marker information may assist the image detection system to locate the marks and facilitate the alignment process. For example, information regarding the number of fiducial marks on each well plate and the location of each mark may be provided so that the system may position each mark within the focus of the image detector without searching for them.

In addition, information that is required in the liquid transfer process may also be extracted from the main database, as shown under "process requirements" in FIG. 19.

The user may load a "mapping profile/database" from the main database in the system, which provides the system the proper instructions as to which fluid it is to transfer to what target device/target location. The system's onboard software may execute this profile directly or take this mapping profile and determine a specific sequence to process the liquid transfer based on algorithms provided by the user. In one example, the fluid transfer sequence is optimized to take minimum amounts of time to complete the fluid transfer. The optimized process sequence may be saved in the database and then executed by the system controller.

In one variation, the mapping profile provided to the liquid transfer apparatus includes the following information (for each intended transfer of liquid between a designated source well to a designated target well): target ID (which identifies a particular target plate where the target well is located), target row number, target column number (which identifies the location of the target well), source ID (which identifies a particular source plate where the source liquid is located), source row number, source column number (which identifies the location of the corresponding source well where liquid are to be transferred from), volume (the amounts of liquid to be transferred). For example, if 100 transfers are called for, the mapping profile may be provided in a spreadsheet with 100 rows and 7 columns, with corresponding variable that are listed above in each column. Furthermore, additional columns may be added to provide information regarding the physical properties of the source liquid in each well.

In one example, the liquid transfer apparatus processes the mapping profile as described below. The apparatus first scans the barcodes on all the source plates and all the target plates in the storage queues to determine which well plates are located in the storage queue and their location in the storage queue. Then the apparatus starts the liquid transfer process by determining the location of the corresponding source well for the first target well on the first target plate in the storage queue by referring to the mapping profile supplied to the apparatus or the optimized process sequence generated by the computer. Once the corresponding source well has been determined, the apparatus retrieves the appropriate source and target well from the storage queue and effectuate the liquid transfer. The apparatus then goes to determine the corresponding source well for the second target well on the first target plate and then completes the liquid transfer. The apparatus goes on iteratively to process all the target wells on the first well plate, then goes on to process the next well plate, until all the targets has been processed. If a particular target well is to be left empty the system controller would skip that well and go onto the next well.

After each ejection, the system may generate a series of data entries that may be stored in a database. A collection of these entries for all the ejection completed for a given set of source and target plates may form the basis for an output database. Some of the variables that may be recorded includes, time of transfer, which is the time of volume transfer for each well; the source and target IDs, which are recorded to reference/analyze the collected data. If the user selects to perform volume measurements, the volume data will then be recorded. If the protocol includes spot measurement, then the liquid transfer apparatus will measure the spot diameter and the location of the liquid that was transferred onto the target plate, and record the information in the database for position accuracy and spot size analysis, which may be performed later.

In one variation, the following variables are saved in the database after each ejection: Time Stamp—Time at which data is collected or volume is transferred; Machine Name—Name of the machine, as there can be multiple machine on the same shop floor; Transporter#—Number of the transporter used in that machine; Z for LL—Height (or position) of the wave-guide/transporter (acoustic wave ejection unit), at the time of liquid level measurement; Freq—Spotting frequency; Amp—Spotting amplitude; Return Status—Status return by liquid level function, that tells if the process for finding liquid level was successful; Mode—There are different conditions that can be set for finding liquid level, mode is the number that defines those conditions; ErrRec-Mode—There are multiple error recovery modes, which can be used depending upon the feedback from different devices in the liquid transfer apparatus; Result—Actual liquid level measured; Z to Spot—Height of the wave-guide, when spotting took place (calculated); Current Z—Height of the wave-guide, when spotting took place (actual);

SrcWell-X—Current source location or the column number of the well; SrcWell-Y—Current source location or the row number of the well; TrgWell-X—Current Target location or the column number of the well; TrgWell-Y—Current Target location or the row number of the well; SrcWPateSNo—Current Source well plate serial number; SrcWplateType—This is type of source well plate for which the liquid transfer apparatus is configured, which can be 96, 384, 1536, etc.; TrgWPateSno—Current Target well plate serial number; TrgWplateType—This is type of Target well plate for which liquid transfer apparatus is configured, which can be 96, 384, 1536, etc.; FluidLevel—Fluid level in the current source well, as entered by the user; Well File—Name of the file that user have selected to be used for well plate physical characteristics; Auto Correct—After detecting the liquid level, if liquid transfer apparatus should auto correct the position of the transporter; User—Name of the user; CorrRatio—This is the factor which tells the user the confidence level of liquid level detection process, higher the number the better it is; Focus—A number that is for the wave-guide and defines its focal point in mm; #of burst—The number of spotting bursts used during spotting process for current transfer of volume; Spot Amp—Measured voltage, during spotting process; Spot Delay(us)—This define the user settable delay, between each spot; Spot Intended—This is defined by the user for total volume needed to be transferred (# of spots); Spot Counted—Number spots ejected by the HTS-01(actual); Comment—Comment inserted by user to keep track of collected data; Spot IDX—Number of spots counted by vision system, for each transfer; Src X pos (mm)—Actual Position of the Source X axis during current transfer; Src Y pos(mm)—Actual Position of the Source Y axis during current transfer; Trg X pos(mm)—Actual Position of the Target X axis during current transfer; Trg X pos(mm)—Actual Position of the Target Y axis during current transfer; Center X(mm)—Center of the resulting target spot detected by vision system, in world coordinates system (a standard coordinate defined by the system), in the X direction (mm); Center Y(mm)—Center of the spot detected by vision system, in world coordinates system, in the Y direction (mm); Dia(mm)—Diameter of the spot, detected by the vision system; Special—This field is used for recording observation by the vision system. As one skilled in the art would appreciate, the user may designate one or more of the variables in the above list to be recorded by the control system in the liquid transfer apparatus. Additional information that the user finds useful may also be associated with each liquid ejection and recorded in the database along with the variables listed above.

The liquid transfer apparatus may have a local database that is associated with each liquid transfer apparatus. The local database may contain information that are unique to the individual apparatus and/or information that are useful during the operation of the apparatus. In one variation shown in FIG. 19, the local database comprises three sub-components: Handshake Database, User Database, and Position Database. The three sub-components provide information that supports the operation of the apparatus to perform the liquid transfer. The Handshake Database specifies software handshakes between subsystems of the liquid transfer apparatus. The User Database includes information about user name, password and access level to the liquid transfer apparatus' computer controller. The Position Database provides the operation parameters for the various mechanisms in the apparatus.

For each moving mechanism, such as the X-Y linear stage, the user may program the system with parameters controlling movement of the mechanism. For example, in the program or setup mode, the user may move the X-Y linear stage to the storage queue access position and allow the computer to register that position. The X-Y linear stage may then be move to the liquid ejection position where the well plate would be above the acoustic emitter and the computer system may register the position. The user may also program the system to define the speed and acceleration for the movement of each individual mechanical part for each movement between a predefined staring position and the predefined destination position. For example, the X-Y linear stage may be programmed to move from the storage queue access position to the liquid ejection position at a predefined speed and acceleration. Different mechanisms (e.g., left elevator, right elevator, source plate X-Y linear stage, target plate X-Y linear stage, vision system, transporter (wave-guide and associated unit)) within the apparatus may have their own movement parameters defining where and how fast to move each part of the device for a particular operation. The position database stores these functional parameters, which may include position, speed, their positive and negative directional limits, and acceleration information, for all the mechanisms and their associated functional operation. When a particular mechanism is to be moved to a predefined location (e.g. a position that was taught to the system), the stored functional parameters are retrieved from the database and executed by the system.

The position database may be programmed with a default set of parameters. The user may then reprogram and/or teach the system with refined position information to improve the operation of the system. The program may have predefined upper and/or lower programming limitation that prevents the user from operating the system beyond its mechanical limitations. The local database may also record performance or equipment operation information so that system performance of the apparatus may be evaluated later. The information stored locally can also be uploaded and downloaded to and from the main database.

Although in the above example the main database and the local database reside on separate computers, it may also be possible to implement a system where both the main database and the local database resides on the same computer. The two database may both reside on the system control computer which is part of the liquid transfer apparatus, or they may both reside on a separate computer remotely and communicate with the system control computer through a computer network (e.g., Ethernet, wireless network). Alternatively, the main database and the local database may also be integrated into a single database.

One skilled in the art would appreciate that various other database structures are also possible. A production line of liquid transfer apparatuses may be configured with a centralized system that controls the various liquid transfer apparatuses. All the database may be provided by the centralized database management system, and information generated by the local liquid transfer apparatus are transferred back the central system. In an alternate design, each liquid transfer apparatus may function independently with its own main database and its own local database. In another variation, the main database reside on a centralized computer system that connects to all the associated liquid transfer apparatuses and each liquid transfer apparatus maintains its own local database. Database may be provided to the computer system (either the central computer or the system control computer resided on each liquid transfer apparatus) through various portable memory storage device (e.g., magnetic disk, flash memory disk, CD-ROM, CD-RW, DVD disk, USB portable memory storage device) or it may be transferred directly to the system through various electronic connections or network (e.g., computer network, wireless network, IR port, Ethernet, USB connections). As one skilled in the art would appreciate, the output database may also be provided through various portable memory storage devices or it may be transferred directly to a remote system through various electronic connections or networks. Alternatively, the output database may be stored in the local system for future access.

In another aspect, an error recovery protocol may be implemented to assist in the operation of the liquid transfer apparatus. The error recovery protocol may allow the liquid transfer apparatus to reduce throughput time (increase efficiency) and also to minimize the overall errors found in the product (quality control). In one example of a liquid transfer process, the apparatus ejects a desired amount of fluid from each source well to a corresponding location on the target in a predetermined order. In the event that a transfer did not successfully occur (e.g., droplet did not eject, ejected droplet did not reach its intended destination) during the process run, this error recovery protocol then commences. First, the location of the "missed" well is stored into a database. The apparatus does not attempt to retry the drop ejection from the missed well at that point in time. The process continues to the next source well according to the original run order. If another failed drop ejection is detected, the location of that next missed well is also simply stored into a database. The process continues again. No attempt to retry drop ejection from the missed well is made until the entire original run order is completed. Upon which, the apparatus will perform a series of re-tries on the missed wells listed in the database.

Alternatively, the apparatus may also support one or more recovery modes. The recovery mode may be delayed,(retry after completion of the original run order, as mentioned above), or real time (immediate retry after detection of a missed well or missed transfer). For example, in one variation, the apparatus supports both the delayed and real-time recovery modes. In this variation, immediately after the detection of a missed well the apparatus will retry the missed well. After one retry (or more than one retry, depending on the system setting), if the liquid transfer is still not completed in that well, the apparatus will record the well as a missed well and move onto the next well. After the entire original run order has been completed, the system controller will retrieve the "missed well" information from the database and retry the missed well.

However, in the event that the number of wells that fails to eject a drop (or fails to complete the transfer of liquid into the intended target well) exceeds a statistically significant number during the original run order, the apparatus may be determined that a machine system error is warranted. In that event, one or more procedures may be performed in an attempt to restore the physical parameters of the apparatus back to an operational state. If unsuccessful, the machine may stop and signal the need for maintenance. But if successful, the missed wells recorded will be re-tried immediately after the machine system error is addressed by the system. Once these specific missed wells are restored, the process run will resume according to the original run order. If after the original run is completed and missed wells still remain in the database, then those wells will then be re-tried at this time. If recovery is still not successful, then those wells are recorded in the database for informational purpose, which may be applied in the analysis and/or utilization when the target plate is utilized in future processing or procedure. For example, if the target plate is being analyzed for chemical reactions after completion of liquid transfer, the missed well will be accounted for in the analysis procedure.

Other criteria that may be considered in determining the path of the error recovery system includes, but is not limited to, spot detection, drop detection, liquid level detection, wave reflection, and drop trajectory, drop speed, drop morphology, spot morphology, and spot location.

[i] Frame and Support Structure

Figure 20:
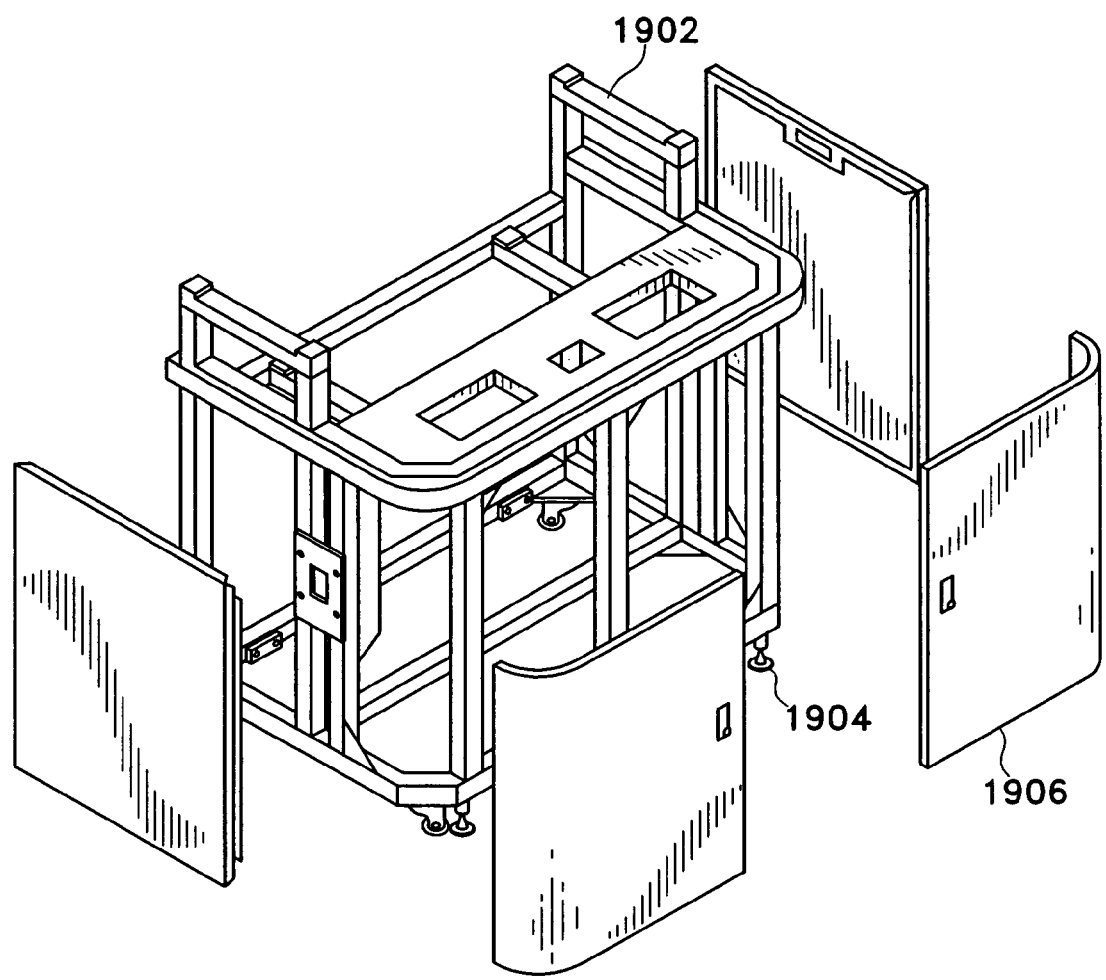
FIG. 20 illustrates one variation of a skeleton-like framework with corresponding panels.

In one variation, the liquid transfer apparatus is built upon an internal skeleton-like framework 1902, as shown in FIG. 20. This framework may provide a rigid structure for which to attach all of the devices and the sub-assemblies. The frame may have additional features such as adjustable feet 1904 for leveling the entire system, casters for easy placement, and/or floor anchors to securely hold the device in place.

Panels may be provided to completely enclose the framework. Panels 1906 may be either hinged or removable to ease access to the apparatus' sub-assemblies for maintenance and/or repair. All panels may be secured by a locking mechanism to prevent unauthorized access and to provide protection to the operator from various hazards, such as electrical voltages and the moving mechanisms of the system.

[j] Environment and Safety Enclosure

An environmental enclosure 1 may be mounted directly to the frame of the liquid transfer system, as seen in FIG. 1. In one variation, it is comprised of a cabinet, a top cover, and front panels/doors.

The environmental enclosure may be configured to maintain temperature and humidity inside the processing chamber. Alternatively, it may be configured to maintain an environment of an anhydrous gas, such as argon or nitrogen. In one variation, the environmental chamber is configured to maintain temperature, humidity, and an environment of oxygen and carbon dioxide gas for cell or tissue incubation. It may also be equipped with a gas inlet device (rotometer) to meter the supplied gas and maintain it at the desired level. An exhaust damper may be adapted in conjunction with the rotometer to control the gas exchange rate and the enclosure pressure. A small amount of gas may be continuously vented out of the system to the exhaust duct. The exhaust duct may be connected to a separate exhaust system. In one variation, the magnehelic gauge may be configured to maintain the pressure inside the chamber at a level below the ambient pressure to minimize the amount of gas escaping out of the chamber. The temperature and humidity control package may include a dehumidification chiller, a heater, a water injection valve, two additional dampers, and/or a relative humidity and temperature sensor. A chiller may be used to remove excess water from the circulating air (or gas) by cooling it below the dew point. Water and/or frost collected by the chiller may be removed periodically by a heater built into the chiller. A series of dampers may be adapted to direct the circulating air to bypass the chiller during the water removal cycle. A heater may be utilized to warm the chilled, dehumidified air after it is re-mixed with the main air flow and before the re-circulating air is returned to the operations chamber. If humidity need to be increased, the system controller may open a water injection valve to release water into a pan above the heater. Evaporated water from the pan may increases the humidity of the air or gas returning to the operations chamber. A relative humidity and temperature sensor may be implemented to control the temperature of the heater, the chiller, the dehumidification chiller, and/or the electric heater, to maintain the environment at a preset temperature and relative humidity.

APPLICATIONS OF THE INVENTION

The liquid transfer apparatus described above may be utilized in various high throughput biological, chemical, and biochemical processes that require efficient transfer of small quantities of liquid. Selective examples of biochemical synthesis and screening applications are described below for illustration purpose only. It is understood that these examples are not intend to be limiting and the present invention may be applicable in various biological, chemical, and biochemical applications, as one skilled in the art would appreciate.

Source fluids contemplated for use in the practice of the present invention may comprise one or more source materials. Source materials may include both biological and chemical compounds, agents and life forms (e.g., plant cells, eukaryotic or prokaryotic cells).

As used herein, "biological compounds" may comprise nucleic acids (e.g., polynucleotides), peptides and polypeptides (including antibodies and fragments of antibodies), carbohydrates (e.g., oligosaccharides), and combinations thereof. In some variations, cells (e.g., eukaryotic or prokaryotic) may be contained in the fluid. Such an arrangement may allow for the transfer of organisms from one source fluid to another fluid or target during cell culturing or sorting.

The term "polynucleotides" and "oligonucleotides" include two or more nucleotide bases (e.g., deoxyribonucleic acids or ribonucleic acids) linked by a phosphodiester bond. Accordingly, such polynucleotides and oligonucleotides include DNA, cDNA and RNA sequences. Polynucleotides and oligonucleotides may comprise nucleotide analogs, substituted nucleotides, and the like. Nucleic acids contemplated for use in the practice of the present invention include naked DNA, naked RNA, naked plasmid DNA, either supercoiled or linear, and encapsulated DNA or RNA (e.g., in liposomes, microspheres, or the like). As will be understood by those of skill in the art, particles mixed with plasmid so as to "condense" the DNA molecule may also be employed.

Polypeptides contemplated for use in the practice of the present invention include two or more amino acids joined to one another by peptide bonds. Thus, polypeptides include proteins (e.g., enzymes (e.g., DNA polymerase), structural proteins (e.g., keratin), antibodies, fragments thereof, and the like), prions, and the like.

"Chemical compounds" contemplated for use in the practice of the present invention may comprise any compound that does not fall under the definition of biological compounds as used herein. Specific chemical compounds contemplated for use in the practice of the present invention includes dyes, detectable labels, non-enzyme chemical reagents, diluents, and the like.

As used herein, the terms "detectable label", "indicating group", "indicating label" and grammatical variations thereof refer to single atoms and molecules that are either directly or indirectly involved in the production of a detectable signal. Any label or indicating agent can be linked to or incorporated in a nucleic acid, a polypeptide, polypeptide fragment, antibody molecule or fragment thereof and the like. These atoms or molecules can be used alone or in conjunction with additional reagents. Such labels are themselves well known in the art.

The detectable label can be a fluorescent-labeling agent that chemically binds to proteins without denaturation to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalene-sulfonylchloride (DANSC), tetramethylrhodamine isothiocyanate (TRITC), lissamine, rhodamine 8200 sulphonyl chloride (RB-200-SC), and the like. A description of immunofluorescence analytic techniques is found in DeLuca, "Immunofluorescence Analysis", in Antibody as a Tool, Marchalonis et al., eds., John Wiley & Sons, Ltd., pp. 189-231 (1982), which is incorporated herein by reference.

The detectable label may be an enzyme, such as horseradish peroxidase (HRP), glucose oxidase, and the like. In such cases where the principal indicating label is an enzyme, additional reagents are required for the production of a visible signal. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

In another variation, radioactive elements are employed as labeling agents. An exemplary radiolabeling agent is a radioactive element that produces gamma ray emissions, positron emissions, or beta emissions. Elements that emit gamma rays, such as 124I, 125I, 126I, 131I and 51Cr, represent one class of radioactive element indicating groups. Beta emitters include 32P, 111Indium, 3H and the like.

The linking of a label to a substrate (e.g., labeling of nucleic acids, antibodies, polypeptides, proteins, and the like), is well known in the art. For instance, antibody molecules can be labeled by metabolic incorporation of radiolabeled amino acids provided in the culture medium. See, for example, Galfre et al., Methods of Enzymology, 73:3-46 (1981). Conventional means of protein conjugation or coupling by activated functional groups are particularly applicable. See, for example, Aurameas et al., Scandinavia Journal of Immunology. Vol. 8, Suppl. 7:7-23 (1978), Rodwell et al., Biotech., 3:889-894 (1984), and U.S. Pat. No. 4,493,795.

In one variation, the methods of the present invention may be used to pair certain ligands (i.e., a molecular group that binds to another entity to form a larger more complex entity) and binding partners for such ligands. For example, certain biological molecules are known to interact and bind to other molecules in a very specific manner. Essentially molecules having a high binding specificity or affinity for each other can be considered a ligand/binding partner pair, e.g., a vitamin binding to a protein, a hormone binding to a cell-surface receptor, a drug binding to a cell-surface receptor, a glycoprotein serving to identify a particular cell to its neighbors, an antibody (e.g., IgG-class) binding to an antigenic determinant, an oligonucleotide sequence binding to its complementary fragment of RNA or DNA, and the like.

Such pairings are useful in screening techniques, synthesis techniques, and the like. Accordingly, in one embodiment of the present invention, screening assays may be performed in which the binding specificity of one compound for another is sought to be determined. For example, multiple test compounds (i.e., putative ligands, optionally having detectable labels attached) may be screened for specific interaction with a selected binding partner. Such assays may be carried out by positioning one of a plurality of putative ligands in each pool of an array of source fluids. The target may comprise, for example, an array of target zones, each zone having affixed to it a sample of the binding partner for which specific binding is sought to be identified. Employing the methods of the invention, a droplet of each putative ligand can be ejected to a target zone and the target thereafter washed under defined conditions. Afterwards, each of the target zones is inspected to determine whether binding of the putative ligand has occurred. Binding of a putative ligand serves to identify that compound as a ligand for the binding partner. Binding can easily be identified by any method known to those of skill in the art. By employing detectable labeled test compounds, binding can readily be determined by identifying a labeled compound bound to the target. Of course, such assays may be reversed, i.e., the selected binding partner may be used as a labeled source compound, while putative ligands are arrayed onto the target.

In another variation, the methods of the invention may also be applied to the identification of peptides or peptide mimetics that bind biologically important receptors. In this variation, a plurality of peptides of known sequence can be applied to a target to form an array using methods described herein. The resulting array of peptides can then be used in binding assays with selected receptors (or other binding partners) to screen for peptide mimetics of receptor agonists and antagonists. Thus, the invention provides a method for producing peptide arrays on a target, and methods of using such peptide arrays to screen for peptide mimetics of receptor agonists and antagonists.

The specific binding properties of binding partners to ligands have implications for many fields. For example, the strong binding affinity of antibodies for specific antigenic determinants is critical to the field of immunodiagnostics. Additionally, pharmaceutical drug discovery, in many cases, involves discovering novel drugs having desirable patterns of specificity for naturally occurring receptors or other biologically important binding partners. Many other areas of research exist in which the selective interaction of binding partners for ligands is important and are readily apparent to those skilled in the art.

The invention may also be employed in synthesis reactions. For example, in another embodiment of the present invention, employing monomeric and/or multimeric nucleotides as source compounds can be employed to synthesize oligonucleotides (useful as probes, labels, primers, antisense molecules, and the like). Such source compounds may be present in a fluid medium (i.e., source fluid) and each source fluid placed in a defined position of an array on the source containment structure. By ejecting source nucleotides from the source containment structure onto a defined target zone of the target, defined nucleotides can be added to a growing product oligonucleotide chain in an additive manner that serves to define the nucleotide sequence of the growing product oligonucleotide.

The particular chemical reactions necessary to perform oligonucleotide synthesis are well known to those of skill in the art. Such reactions, or others, which may become known, can be performed in situ on the target by, for example, contacting the growing oligonucleotide with the necessary reagents between each iterative addition of further nucleotide(s). Flowing the reagents across the target, by passing the target through a reagent bath, or the like can perform reagent contacting. By employing a target with a suitable coating or having suitable surface properties, the growing oligonucleotide can be bound to the target with sufficient strength to undergo the necessary chemical reactions, after which the mature oligonucleotide can be released from the target. For example, methods for attaching oligonucleotides to glass plates in a manner suitable for oligonucleotide synthesis are known in the art. Southern, Chem. abst. 113; 152979r (1990), incorporated by reference herein in its entirety, describes a stable phosphate ester linkage for permanent attachment of oligonucleotides to a glass surface. Mandenius et al., Anal. Biochem. 157; 283 (1986), incorporated by reference herein in its entirety, teaches that the hydroxyalkyl group resembles the 5'-hydroxyl of oligonucleotides and provides a stable anchor on which to initiate solid phase synthesis. Other such binding/release technologies are also known or may become available and are thus contemplated for use in the practice of the present invention.

All publications and patent applications cited in this specification are herein incorporated by reference in their entirety as if each individual publication or patent application were specifically and individually put forth in the text below.

This invention has been described and specific examples of the invention have been portrayed. The use of those specifics is not intended to limit the invention in anyway. Additionally, to the extent there are variations of the invention, which are within the spirit of the disclosure or equivalent to the inventions found in the claims, it is our intent that this patent will cover those variations as well.

I claim the following:

1. A method of isolating a coupling liquid at a tip of an acoustic wave-guide comprising the steps of:
    supplying a volume of the coupling liquid for coupling the acoustic wave-guide with a fluid containment structure; and
    localizing the coupling liquid to a distal end of said acoustic wave-guide;
    wherein localizing the coupling liquid comprises maintaining a suction in an area surrounding the distal end of said acoustic wave-guide, the suction capturing and removing excess coupling liquid; and
    wherein the supplying step comprises supplying a continuous flow of coupling liquid to the distal end of said wave-guide.

2. The method of claim 1 further comprising:
    compensating for a vertical motion of said wave-guide by adjusting the volume of the coupling liquid simultaneously with movement of the wave-guide.

3. The method of claim 1 further comprising the step of:
    positioning the fluid containment structure above said wave-guide such that said coupling liquid is positioned between said wave-guide and said fluid containment structure, and said coupling liquid contacts said wave-guide and said fluid containment structure, wherein said fluid containment structure has a source fluid contained within said structure.

4. The method of claim 3 further comprising the step of:
    propagating an acoustic wave through said wave-guide, said coupling liquid, said source fluid containment structure and into said source fluid.

5. The method of claim 1 wherein the localizing step comprises maintaining the suction as a continuous suction in the area surrounding the distal end of said wave-guide.

6. The method of claim 4 wherein the fluid containment structure comprises a structure having a plurality of wells, and at least two of the wells contain source fluids.

7. The method of claim 4 wherein the propagating step further comprises:
    adjusting the position of the wave-guide in a vertical direction;
    adjusting the volume of the coupling liquid between said wave-guide and said fluid containment structure such that the coupling liquid maintains contact with both the wave-guide and the bottom surface of said fluid containment structure; and
    propagating an acoustic wave through said wave-guide, said coupling liquid, said fluid containment structure and into said source fluid.

8. The method of claim 7 wherein the steps of adjusting the position of the wave-guide and adjusting the volume of the coupling liquid occurs simultaneously.

9. The method of claim 6 further comprising the steps of:
    moving the position of the source fluid containment structure laterally so that a second well is positioned above the wave-guide, said second well having a second source fluid; and
    propagating an acoustic wave through said wave-guide, said coupling liquid, said fluid containment structure and into said second source fluid.

10. The method of claim 1 further comprising:
    adjusting the position of the wave-guide in a vertical direction; and
    adjusting the volume of the coupling liquid between said wave-guide and said fluid containment structure such that the coupling liquid maintains contact with both the wave-guide and the fluid containment structure.

11. The method of claim 10 wherein the steps of adjusting the position of the wave-guide and adjusting the volume of the coupling liquid occurs simultaneously.

12. The method of claim 4, wherein the acoustic wave is of sufficient intensity and strength to eject a portion of said source fluid.

* * * * *